US011955232B2

(12) United States Patent
Douglas et al.

(10) Patent No.: US 11,955,232 B2
(45) Date of Patent: Apr. 9, 2024

(54) IMMERSIVE MEDICINE TRANSLATIONAL ENGINE FOR DEVELOPMENT AND REPURPOSING OF NON-VERIFIED AND VALIDATED CODE

(71) Applicant: DEEPWELL DTX, Las Vegas, NV (US)

(72) Inventors: Ryan J. Douglas, Seattle, WA (US); Matthew J. Douglas, Seattle, WA (US); Parker J. Douglas, Victoria (CA); Jalen S. Douglas, Victoria (CA); Michael S. Wilson, Seattle, WA (US)

(73) Assignee: DEEPWELL DTX, Las Vegas, NV (US)

( * ) Notice: Subject to any disclaimer, the term of this patent is extended or adjusted under 35 U.S.C. 154(b) by 0 days.

(21) Appl. No.: 18/172,111

(22) Filed: Feb. 21, 2023

(65) Prior Publication Data
US 2023/0197261 A1 Jun. 22, 2023

Related U.S. Application Data

(63) Continuation of application No. PCT/US2021/071585, filed on Sep. 24, 2021.
(Continued)

(51) Int. Cl.
*G16H 40/40* (2018.01)
*G16H 50/30* (2018.01)

(52) U.S. Cl.
CPC ............. *G16H 40/40* (2018.01); *G16H 50/30* (2018.01)

(58) Field of Classification Search
CPC ............................... G16H 40/40; G16H 50/30
See application file for complete search history.

(56) References Cited

U.S. PATENT DOCUMENTS 7,440,905 B2 10/2008 Ellis et al.
7,698,148 B2 4/2010 Lavu et al.
(Continued)

FOREIGN PATENT DOCUMENTS

WO 2017127818 A1 7/2017

OTHER PUBLICATIONS

D. McPheron, "Video gaming accessibility," 2015 Computer Games: AI, Animation, Mobile, Multimedia, Educational and Serious Games (CGAMES), Louisville, KY, USA, 2015, pp. 107-111, doi: 10.1109/CGames.2015.7272966. (Year: 2015).*
(Continued)

*Primary Examiner* — Evangeline Barr
(74) *Attorney, Agent, or Firm* — Thompson Patent Law Offices

(57) ABSTRACT

Apparatus and associated methods relate to management of therapeutic digital assets in a non-medical environment. In an illustrative example, non-medical digital asset(s) (NM-DAs) may be evaluated relative to one or more therapeutic modalities. A corresponding therapeutic digital asset (TDA) may, for example, be generated for each therapeutically associated NMDA. The TDA may, for example, be traceably associated with corresponding risks and/or risk mitigations. Each TDA may be associated, for example, with a test profile corresponding to a risk and/or risk mitigation. A TDA may be released into a non-medical digital content delivery environment (DCDE), for example. The TDA may, for example, be monitored in the DCDE to maintain verification and/or validation (VV). A change in the DCDE affecting VV of the TDA may, for example, result in deactivation of the TDA in the DCDE. Various embodiments may advantageously permit VV of selected digital assets in a non-medical environment.

22 Claims, 16 Drawing Sheets

Related U.S. Application Data

(60) Provisional application No. 63/260,128, filed on Aug. 10, 2021, provisional application No. 63/203,673, filed on Jul. 27, 2021, provisional application No. 63/203,058, filed on Jul. 6, 2021, provisional application No. 63/202,881, filed on Jun. 28, 2021, provisional application No. 63/181,213, filed on Apr. 28, 2021, provisional application No. 63/172,379, filed on Apr. 8, 2021, provisional application No. 63/090,000, filed on Oct. 9, 2020, provisional application No. 63/198,030, filed on Sep. 24, 2020.

(56) References Cited

U.S. PATENT DOCUMENTS

| | | | |
|---|---|---|---|
| 11,295,261 | B2 | 4/2022 | Douglas |
| 2004/0098300 | A1 | 5/2004 | Karwatowski et al. |
| 2008/0275533 | A1 | 11/2008 | Powell |
| 2012/0254710 | A1 | 10/2012 | Flanagan et al. |
| 2013/0006701 | A1 | 1/2013 | Guven et al. |
| 2014/0081700 | A1 | 3/2014 | Mehta |
| 2014/0128745 | A1 | 5/2014 | Willis |
| 2015/0032643 | A1 | 1/2015 | Loewen et al. |
| 2015/0037771 | A1* | 2/2015 | Kaleal, III ............ G16H 50/30 434/257 |
| 2015/0134398 | A1 | 5/2015 | Xiao |
| 2015/0157938 | A1* | 6/2015 | Domansky ........... A61B 5/4848 463/7 |
| 2015/0356477 | A1 | 12/2015 | Milkman et al. |
| 2018/0032639 | A1 | 2/2018 | Nakagawa et al. |
| 2019/0026675 | A1 | 1/2019 | McKibbin et al. |
| 2019/0189259 | A1* | 6/2019 | Clark .................... G16H 10/60 |
| 2019/0243944 | A1* | 8/2019 | Jain ....................... G16H 80/00 |
| 2019/0362279 | A1 | 11/2019 | Douglas |
| 2020/0129728 | A1 | 4/2020 | Pinkerton et al. |

OTHER PUBLICATIONS

Capon, F, Record numbers of children need specialist mental health care in Covid pandemic, Times Newspapers, Feb. 4, 2022, 4 pages, https://www.thetimes.co.uk/article/record-numbers-of-children-need-specialist-mental-health-care-in-covid-pandemic-rmj25rkdx.

Hill, M, Teens aren't built for quarantine, Insider, Feb. 4, 2022, 7 pages, https://www.insider.com/covid-isolation-is-affecting-my-teenagers-mental-health-2022-1.

International Preliminary Report on Patentability of the International Searching Authority in related International Application No. PCT/US2021/071585, dated Dec. 14, 2022, 14 pages.

International Search Report and Written Opinion of the International Searching Authority in related International Application No. PCT/US2021/071585, dated Jan. 17, 2022, 14 pages.

Krus, D, et al., A Step Toward Risk Mitigation During Conceptual Product Design: Component Selection for Risk Reduction, Journal of Failure Analysist and Prevention, 11(4), 432-445, 2011, 14 pages.

Petersen, A, What Parents Can Do When Kids Have Suicidal Thoughts, The Wallstreet Journal, Feb. 3, 2022, 4 pages, https://www.wsj.com/articles/amid-pandemic-more-u-s-adults-say-they-considered-suicide-11597362131.

Thomas et al., Death of former Miss USA puts spotlight on 'high functioning depression' and it's impact, WPVI-TV Philadelphia, Feb. 4, 2022, 8 pages, https://apple.news/AX9AsuvB1Q5uFqYZIZIbUow.

Ward, F, This is what it's like to have panic disorder (and no, it's not the same as generalised anxiety disorder), Glamour, Feb. 5, 2022, 10 pages, https://www.glamourmagazine.co.uk/article/panic-disorder.

* cited by examiner

IMMERSIVE MEDICINE TRANSLATIONAL ENGINE FOR DEVELOPMENT AND REPURPOSING OF NON-VERIFIED AND VALIDATED CODE

CROSS-REFERENCE TO RELATED APPLICATIONS

This application is a Continuation application and claims the benefit of PCT Application Serial No. PCT/US21/71585 (the "'585 PCT application"), titled "IMMERSIVE MEDICINE TRANSLATIONAL ENGINE FOR DEVELOPMENT AND REPURPOSING OF NON-VERIFIED AND VALIDATED CODE," filed by Ryan J. Douglas, et al., on Sep. 24, 2021. The '585 PCT application claims the benefit of U.S. Provisional Application Ser. No. 63/090,000, titled "IMMERSIVE MEDICINE PLATFORM AND MEDIA FOR EFFICIENT DELIVERY OF THERAPEUTIC LIGHT," filed by Ryan J. Douglas, et al., on Oct. 9, 2020.

The '585 PCT application claims the benefit of U.S. Provisional Application Ser. No. 63/172,379, titled "DEEPWELL DIGITAL THERAPEUTIC CONCEPT," filed by Ryan J. Douglas, et al., on Apr. 8, 2021.

The '585 PCT application claims the benefit of U.S. Provisional Application Ser. No. 63/260,128, titled "Patient Compliance-Inducing Digital Therapeutic Game Mechanics," filed by Ryan J. Douglas, et al., on Aug. 10, 2021.

The '585 PCT application claims the benefit of U.S. Provisional Application Ser. No. 63/181,213, titled "WEARABLE AUDIO BIOFEEDBACK RESPIRATORY DETERMINATION FOR HYPERTENSION THERAPY," filed by Ryan J. Douglas on Apr. 28, 2021.

The '585 PCT application claims the benefit of U.S. Provisional Application Ser. No. 63/202,881, titled "Immersive Digital Therapy," filed by Ryan J. Douglas on Jun. 28, 2021.

The '585 PCT application claims the benefit of U.S. Provisional Application Ser. No. 63/203,058, titled "Management and Validation of Distributed Implementation of Treatment Modules," filed by Ryan J. Douglas, et al., on Jul. 6, 2021.

The '585 PCT application claims the benefit of U.S. Provisional Application Ser. No. 63/198,030, titled "IMMERSIVE MEDICINE TRANSLATIONAL ENGINE FOR THE DEVELOPMENT AND REPURPOSING OF NON-VERIFIED AND VALIDATED CODE," filed by Ryan J. Douglas on Sep. 24, 2020.

The '585 PCT application claims the benefit of U.S. Provisional Application Ser. No. 63/203,673, titled "Deepwell Immersive Therapeutic Digital Media," filed by Ryan J. Douglas, et al., on Jul. 27, 2021.

This application incorporates the entire contents of the foregoing application(s) herein by reference.

The subject matter of this application may have common inventorship with and/or may be related to the subject matter of the following:
U.S. application Ser. No. 16/423,981, titled "Quality Management Systems," filed by Ryan J. Douglas on May 28, 2019.

This application incorporates the entire contents of the foregoing application(s) herein by reference.

TECHNICAL FIELD

Various embodiments relate to delivering treatment modalities for diseases and/or enhancement through augmentation and/or adaptation of digital media.

BACKGROUND

Medical therapy may include various exercise and/or equipment. Patients may undergo medical therapy under the supervision of a caretaker (e.g., physician, therapist). Medical therapy may, for example, be performed at a medical facility (e.g., hospital, clinic) and/or in a home-based environment.

Medical devices may, for example, include software components. Software components may be regulated by one or more regulatory bodies, such as the Food and Drug Administration in the United States of America. Medical device software components may be required to be tested according to regulatory standards before release.

SUMMARY

Apparatus and associated methods relate to management of therapeutic digital assets in a non-medical environment. In an illustrative example, non-medical digital asset(s) (NMDAs) may be evaluated relative to one or more therapeutic modalities. A corresponding therapeutic digital asset (TDA) may, for example, be generated for each therapeutically associated NMDA. The TDA may, for example, be traceably associated with corresponding risks and/or risk mitigations. Each TDA may be associated, for example, with a test profile corresponding to a risk and/or risk mitigation. A TDA may be released into a non-medical digital content delivery environment (DCDE), for example. The TDA may, for example, be monitored in the DCDE to maintain verification and/or validation (VV). A change in the DCDE affecting VV of the TDA may, for example, result in deactivation of the TDA in the DCDE. Various embodiments may advantageously permit VV of selected digital assets in a non-medical environment.

Various embodiments may achieve one or more advantages. For example, some embodiments may advantageously selectively verify and/or validate TDAs deployed among non-therapeutic NMDAs 105. Some embodiments may advantageously reduce regulatory burden. Various embodiments may, for example, advantageously enable use of conventional code in an environment requiring validation testing, such as regulated medical uses.

Various embodiments may, for example, advantageously implement digital therapeutics to reduce patient compliance issues. For example, various embodiments may stimulate physiological responses (e.g., dopamine, oxytocin, endorphins and/or serotonin production, hormone(s), neurotransmitter(s)). Such embodiments may, for example, advantageously enable delivery of proven treatment modalities for acute and/or chronic diseases. Immersive stimulus may advantageously provide an efficient mechanism for neurological reprogramming for positive mental and/or physiological functioning. Various embodiments may advantageously achieve subconscious neurological entrainment with a wildly effective positive reinforcement feedback loop. Some embodiments may advantageously provide patient-desired therapy that does not require a patient's willpower to force themselves to undertake.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, to help introduce discussion of various embodiments, an exemplary therapeutic digital asset management (TDAM) system is introduced with reference to FIG. 1. Second, that introduction leads into a description with reference to FIG. 2 of some exemplary embodiments of immersive therapy using digital assets. Third, with reference to FIGS. 3-4, an exemplary therapeutic digital asset (TDA) management engine is described in application to exemplary digital content delivery environments (DCDEs) including game engines. Fourth, with reference to FIGS. 5-6, the discussion turns to exemplary embodiments that illustrate methods of managing creation, identification, development, and/or deployment off TDAs. Fifth, and with reference to FIG. 7-13, this document describes exemplary apparatus and methods useful, for example, for management of TDAs during development and/or deployment. Sixth, this disclosure turns to discussion of exemplary TDAM embodiments in the context of light delivery with reference to FIGS. 14-16. Finally, the document discusses further embodiments, exemplary applications and aspects relating to immersive medicine delivery and TDAM systems.

Figure 1:
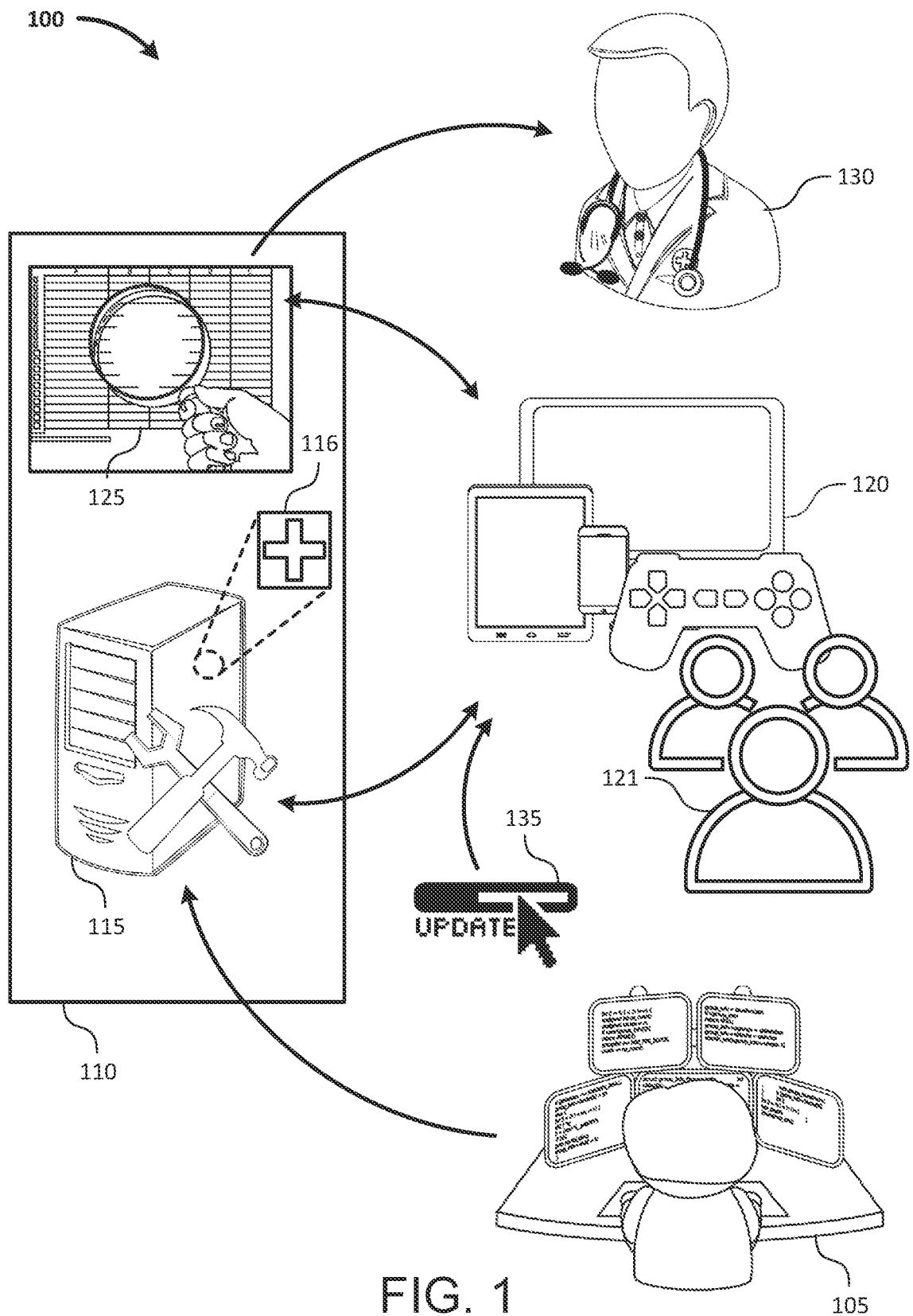
FIG. 1 depicts an exemplary therapeutic digital asset management (TDAM) system in an exemplary use case for validation of digital assets for medical use.

FIG. 1 depicts an exemplary therapeutic digital asset management (TDAM) system in an exemplary use case for validation of digital assets for medical use. In a depicted use-case scenario 100, nonmedical digital assets (NMDAs 105) are generated and/or retrieved and passed to a TDAM system 110. The TDAM system 110 includes a TDA management engine 115 and a testing engine (TE 125).

In some embodiments the NMDAs 105 may include software code. For example, software code may include software libraries, frameworks, code modules, or some combination thereof. Software code may, for example, include configuration files. In some example software code may include, for example, code files, precompiled code, code snippets, code modules, or some combination thereof. Some embodiments may include NMDAs 105 in the form of metadata.

In some embodiments the NMDAs 105 may, for example, include media assets. For example, media assets may include audio files. In some embodiments, media assets may include video files. In some embodiments media assets may include image files. In some embodiments the NMDAs 105 may, for example, include text. In various embodiments, the NMDAs 105 may include animations. In some embodiments the NMDAs 105 may, for example, include vector files.

In various embodiments, by way of example and not limitation, the NMDAs 105 may be received individually. For example, an individual NMDA may be retrieved and/or uploaded.

In some embodiments the NMDAs 105 may, for example, be received as a group. In some examples, a group of NMDAs may be received in a group transfer. A single group of NMDAs may, for example, be unrelated. In some embodiments a group of NMDAs may be received as a related group. For example, the NMDAs may be at least part of an order combination and/or structure. For example, the NMDAs may be part of pre-existing digital content. As an illustrative example the NMDAs 105 may be a digital feature film. As an illustrative example the NMDAs 105 may include a digital book. As an illustrative example the NMDAs 105 may include an existing videogame.

In the depicted example, the TDA management engine 115 identifies (one or more) TDAs 116 of the NMDAs 105. The TDAs 116 may, for example, include components of the NMDAs 105 that affect therapy. The TDAs 116 may, for example, include components with a health effect. The TDAs 116 may, for example, include components of the NMDAs 105 subject to regulatory oversight (e.g., FDA regulation).

In some embodiments the TDAs 116 may, for example, be automatically identified. The NMDAs 105 may, for example, be identified by the TDA management engine 115 by application of one or more therapeutic profiles. The therapeutic profiles may, for example, contain criteria associated with (potential) TDAs 116. The therapeutic profiles may, by way of example and not limitation, define physiological effects and/or code attributes associated with physiological effects. As an illustrative example, a therapeutic profile may, by way of example and not limitation, define criteria related to speed in a running game. The criteria may be associated with a therapeutic application corresponding, for example, to cardio-related therapy and/or pulmonary-related therapy. The criteria may, for example, be applied by the TDA management engine 115 to identify components of the NMDAs 105 (which may be) related to therapeutic aspects (e.g., heart rate, breath rate).

In some embodiments the TDAs 116 may, for example, be manually identified. For example, a reviewer may compare a (predetermined) therapeutic profile to the NMDAs 105 and identify (potential) TDAs 116. In response to the reviewer's input, the TDA management engine 115 may generate and/or update at least one metadata file, for example, identifying the TDAs 116 in the NMDAs 105. The metadata file may, for example, be associated with the NMDAs 105.

In some embodiments, potential therapeutic components of the NMDAs 105 may, for example, be automatically identified (e.g., by application of at least one therapeutic profile). At least one corresponding (metadata) file may, for example, be generated and associated with the NMDAs 105. A display including the identified potential therapeutic components may be generated based on the corresponding file. The display may include at least one of the identified potential therapeutic components. The display may include at least one corresponding attribute and/or criterion of the therapeutic profile. The display may include at least one portion of the NMDAs 105 associated with the identified potential therapeutic component(s). For example, speed control code may be identified as a therapeutic component. The therapeutic profile may, for example, include speed parameters. Code from the NMDAs 105 associated with the speed control code (e.g., code interacting with the potential therapeutic component) may be presented. The display may, for example, be presented to a user (e.g., a reviewer). The display may, for example, prompt a user for input corresponding to whether the potential therapeutic component is determined to be a TDA.

In some embodiments the TDAs 116 may, for example, include at least one treatment asset (TA). The TDAs 116 may, for example, include software code (e.g., at least a portion of a program of instructions configured to be executed by at least one processor). The TDAs 116 may, for example, include one or more parameters. A parameter(s) may, for example, be embodied as a digital file (e.g., metadata file). The TDAs 116 may, for example, include digital media. Digital media may, for example, include audio media. Digital media may, for example, include video media. Digital media may, for example, include visual media (e.g., still pictures). Digital media may, for example, include vector media. Digital media may, for example, include visual animation(s).

The TDA management engine 115 establishes risk analysis and/or risk mitigation related to the TDAs 116 of the NMDAs 105. Accordingly, the NMDAs 105 may be transformed into verifiable and/or validatable code. In some embodiments the TDAs 116 may be associated with risks. The TDAs 116 may be associated with risk mitigations corresponding to the risks. Test profiles may, for example, be associated with the TDAs 116. For example, the test profiles may establish test approved test results corresponding to the risks and/or risk mitigations. Various embodiments may, for example, generate one or more metadata structures defining the association(s). The metadata structures may, for example, be associated with the corresponding TDAs 116. For example, the metadata structures may be attached to, stored with, transmitted with, and/or incorporated into the corresponding TDAs 116.

In some embodiments, test profiles may only be associated with the TDAs 116 of the NMDAs 105. Such embodiments may, for example, verify and/or validate only the TDAs 116. Components of the NMDAs 105 which are not identified as (potentially) therapeutic may, for example, not be verified and/or verified and/or validated. Such components may, for example, not be provided with test points. Accordingly, various embodiments may advantageously selectively verify and/or validate only the TDAs 116 of the NMDAs 105. Such embodiments may advantageously reduce regulatory burden. For example, non-therapeutic components may be left free to be updated. Accordingly, cost may be decreased for maintaining, updating, creating, and/or enhancing non-therapeutic code components even when applied in the context of potentially therapeutic uses. Creativity, choice, and/or speed of enhancement may, for example, be increased by selectively isolating only the TDAs 116 of the NMDAs 105 for verification and/or validation.

The verifiable and/or validatable digital content is then provided to digital content delivery device(s) (DCDDs 120) (e.g., general purpose computing devices, computers, tablets, smartphones, gaming devices). At least some of the DCDDs 120 may, for example, be running general-purpose operating systems (GPOSs). The DCDDs 120 may, for example, deliver the content to one or more users 121.

For example, the TDAs 116 associated with the test profiles, risks, and/or risk mitigations may be recompiled with the remainder of the NMDAs 105. Accordingly, verified and/or verifiable and/or validatable digital content may be provided. The verifiable and/or validatable code (e.g., only the TDAs 116) may be verified and/or validated in combination with the DCDDs 120 running GPOSs by the TE 125. Once the combination of verifiable and/or validatable code and DCDDs 120 passes testing of the TE 125, the combination may be released to users 130 for medical use.

When an update 135 is made, for example, to the DCDDs 120 (e.g., an operating system update), the test profile(s) associated with the TDAs 116 may be performed by the TE 125 before releasing the new combination of the DCDD environment (e.g., GPOS) and verifiable and/or validatable code to users 130. The medical use may, for example, include use by physicians, self-use (e.g., therapeutic gaming), or some combination thereof. Various embodiments may, for example, advantageously enable use of conventional code in an environment requiring validation testing, such as regulated medical uses.

Figure 2:
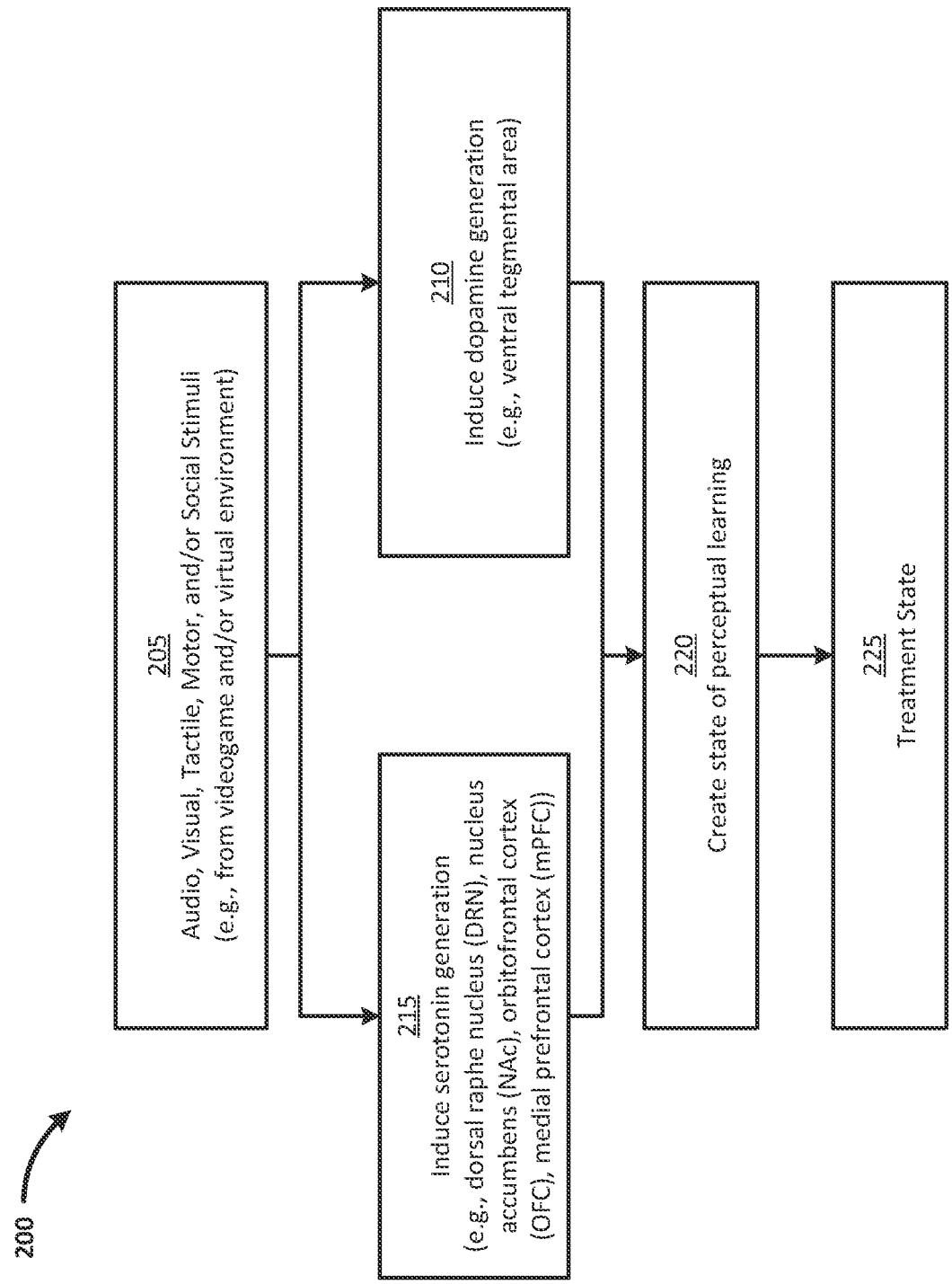
FIG. 2 depicts an exemplary therapeutic delivery method using therapeutic digital assets (TDAs).

FIG. 2 depicts an exemplary therapeutic delivery method using therapeutic digital assets (TDAs). A method 200 includes applying stimuli in a step 205. The stimuli may include, by way of example and not limitation, audio stimuli, visual stimuli, tactile stimuli, motor stimuli, social stimuli, or some combination thereof, as depicted in FIG. 2.

Treatment modalities may provide one or more (predetermined and/or dynamic) stimuli profile configured to stimulate one or more areas of a user's brain. The stimuli may, for example, be configured to induce at least one treatment state. The treatment state may, for example, induce (endogenous) generation of one or more chemical compounds (e.g., dopamine, oxytocin, endorphins, serotonin). In the depicted example, stimuli are applied in a step 210 to induce dopamine generation. For example, the stimuli may be configured to stimulate at least a ventral tegmental area of a user's brain. The stimulation may, for example, correspond to altered (e.g., increased) dopamine generation.

In the depicted example, stimuli are applied in a step 215 to induce serotonin generation. For example, the stimuli may be configured to stimulate a dorsal raphe nucleus (DRN), a nucleus accumbens (NAc), an orbitofrontal cortex (OFC), a medial prefrontal cortex (mPFC), or some combination thereof, of a user's brain. The stimulation may, for example, correspond to altered (e.g., increased) serotonin generation.

The stimuli may, for example, be controlled, in a step 220 such that the dopamine oxytocin, endorphins, and/or serotonin generation induces a state of perceptual learning. Perceptual learning may, for example, correspond to induction of learning of a (therapeutic) modality via sensory perception without conscious thought to learn the modality. The method may control the perceptual learning, for example, such that the perceptual learning induces, in a step 225, at least one treatment state.

In a first treatment state, by way of example and not limitation, dopamine production may be used for therapy (e.g., acute treatment). For example, in various embodiments the first treatment state may be used, by way of example and not limitation, for (acute) treatment of a disease state, such as depression, Parkinson's and certain speech disorders, which may be responsive to (endogenous) dopamine production. For some diseases, delivery of at least one chemical compound (e.g., dopamine) may be at least some portion of a desired therapy. Externally produced compounds may, for example, not reach a desired efficacy level or be ineffective for therapy. Accordingly, in some embodiments therapy may stimulate endogenous generation of one or more therapeutic compounds including, by way of example and not limitation, dopamine.

In a second treatment state, dopamine production may act as therapy delivery (e.g., a distraction/induction state) for neuroplasticity-based training and/or retraining of subconscious behavior. This state may, for example, be a therapy delivery state. The therapy delivery state may induce perceptual learning in a user (e.g., patient, athlete). The perceptual learning may, for example, distract the user with an interactive digital carrier (e.g., gaming, music, guided dancing) away from a perception of conscious learning and/or an undesired state (e.g., depressed, anxious, angry). Therapy may be delivered during this 'distracted' state of neural plasticity. This state may, for example, be used to provide additional learning to induce acute and/or chronic physiological and/or behavior changes. Accordingly, various such embodiments may provide sub-conscious training of therapeutic modalities. Therapeutic modalities may, for example, include physiological, mentation, endogenous chemical compound generation, or some combination thereof. Subconscious training of therapeutic modalities may achieve a desired (physiological) result. Such embodiments may, for example, induce neural plasticity and/or suspend disbelief to achieve subconscious learning of a desired therapeutic modality. Various embodiments may, for example, be configured to use the second treatment state for long-term (e.g., chronic) therapy.

Various embodiments may involve digital therapeutics, including, for example, (digital) media. In various embodiments digital therapeutics may advantageously reduce patient compliance issues. For example, digital therapeutics may create states of perceptual learning as a therapy delivery and direct therapeutic mechanisms through the therapeutic augmentation and/or adaptation of media as an (interactive) digital carrier of the therapy. For example, digital carrier(s) shown to stimulate the bodies pleasure centers of the brain may be selected. By way of example and not limitation, digital carrier(s) may be selected based on stimulation of the nucleus accumbens (e.g., serotonin production) in the limbic system near the center of the brain, the ventral tegmental area (VTA) (e.g., a prime location for dopamine production), or some combination thereof. Stimulation of such regions, for example, may advantageously allow delivery of proven treatment modalities for acute and/or chronic diseases.

The medical device and pharmaceutical industry spend billions of dollars each year developing and releasing treatments for common ailments that are both preventable and treatable. Insurance payers and individuals in turn spend billions on monthly insurance payments, doctor visit co-pays and out-of-pocket deductibles for medical device and drug purchases. However, access to trained medical professionals, proven treatments and patient education have yet to overcome the greatest issue in providing effective treatment—patient compliance.

In contrast, the media, social media, and video-gaming industry enjoys a history of easily compelling users to repeat behaviors and can be so compelling as to suffer from an issue of addiction, similar to drugs and other activities that stimulate the brain's reward areas. Video games may, for example, regulate emotion and motivation towards a specific activity.

Traits, habits, and/or behaviors required for self-regulation and treatment may be largely acquired and/or effected subconsciously. For example, such modalities may be acquired and/or effected through heightened state(s) of unconscious learning, including but not limited to perceptual learning, neuroplasticity, and/or (ultimately) reprogramming of the sympathetic and parasympathetic nervous systems and/or sensory and motor functions of the body. Therefore, instruction and practice on the conscious level may not result in translation to subconscious mastery (e.g., 'automatic' implementation by a patient without consciously purposing to use the instruction and/or practice). Achieving subconscious (e.g., 'reflexive') mastery of a treatment modality (e.g., regulated breathing) via instruction and practice solely at a conscious level may, for example, require durations of instruction and/or levels of concentration multiples of that required for delivery of the treatment modality subconsciously while the user's conscious focus is on another (e.g., desired) goal and/or object.

Various embodiments may provide confluence between gaming and effective treatment mechanisms. By way of example and not limitation, such implementations may directly provide instruction on a subconscious level of a participant's (e.g., patient) brain. Instruction may, for example, be delivered by embedding training of a treatment regime in a gaming mechanism. For example, various embodiments may provide augmentation of a gaming mechanism with a treatment modality such that user engagement of the gaming mechanism induces subconscious learning with the treatment modality and/or direct treatment via the release of neurochemicals into the body from the game play, social and/or other game-related activities, immediate and/or long-term interactions, or some combination thereof.

In various embodiments, a compelling nature of the game play must be primary. The gaming itself may act as a treatment and/or a training mechanism for the technique, biofeedback mechanism, motor, sensory or processing skill that must be learned to induced to create the desired treatment outcome. Accordingly, various embodiments may seamlessly integrate into compelling game play. For example, in various embodiments an existing game with known compelling and/or 'addictive' aspects of play may be augmented (e.g., 'enriched') with therapeutic behaviors such as physiological mechanics and/or practices. Specific physiological mechanics and/or practices may, for example, be integrated into the game environment such that a user may learn the physiological behaviors to (better) play the game.

Accordingly, various embodiments may implement immersive medicine. Immersive medicine overcomes the single greatest challenge to human treatment, reconditioning and enhancement: patient compliance. Various embodiments may implement immersive medicine by providing medically beneficial conditioning through socially supported and/or biologically compelling thoughts and behaviors.

Various embodiments may, for example, provide a patient a believably reconstructed reality whereby a desired (e.g., self-directed) treatment condition is achieved through thematically appropriate, adaptively increasing challenges or conditions linking a critically important and socially supported game mechanic or function to a learned treatment mechanism or behavior facilitating neural plasticity through subconscious conditioning in an unconscious state. For example, such a state may be induced when conscious thought is directed to game play and not the treatment condition. The game play may, for example, induce dopamine production. The dopamine production may, for example, allow the player to enter a state where their subconscious is available for retraining, programming, and/or other alterations without consciously registering the work being done to facilitate the shift in thought and resulting behavioral patterns. Immersive medicine may allow the patient to develop and/or regain a vitally important biological function. Accordingly, various embodiments may provide a patient with enduring access to the biological function through conscious choice and/or subconsciously directed autonomic functioning. At peak levels of immersive medical conditioning, the body and mind may, for example, be capable of subconsciously adapting and/or applying a learned mechanism(s) of action (e.g., learned in the context of the game environment) to any appropriate challenge condition the patient encounters (e.g., even outside of a game environment). Such conditioning may, for example, allow the immersive treatment to facilitate adaptive chronic self-care. Accordingly, various embodiments may (ultimately) drive enduring enhancement of mind and body function through entrainment. Entrainment may, for example, include improved/enhanced neurological processing and resulting body system functioning.

In some examples, mechanics (e.g., motions) and/or practices (e.g., rhythmic breathing) learned during game play may be instilled into a patient as a (purposeful) 'side-effect' of play such that use of the skill or reflexive action in a treatment regime may be accessed easily using familiar sensory and motor feedback mechanisms.

Various embodiments may implement immersive medicine using sensory and/or social stimulus to access a user's subconscious during physiological and/or mental training, challenges, and/or treatment. The immersive stimulus may, for example, distract the patient. Accordingly, the immersive stimulus may advantageously provide an efficient mechanism for neurological reprogramming, developing new neural pathways for positive mental and/or physiological functioning. The effects may include, by way of example and not limitation, reduction of acute symptoms and treatment of chronic conditions through subconscious reprogramming.

In various embodiments such reprogramming may be evident, for example, as entrainment. The 'reprogramming' may extend, for example, to the patient's general improved functioning outside the game (training/treatment) environment. In some such embodiments the patient may not even notice the entrainment affect. For example, the patient may be (substantially entirely) distracted by the immersive environment in pursuit of intrinsically motivated goals built through the theme and culture of the gaming environment.

Immersive medicine may, for example, be effective in embodiments when the game theme, culture, mechanics, and challenges align with the treatment protocol allowing a flow-state to be achieved with immediate and longer-term suspension of disbelief and engagement with the training/treatment environment. The flow-state may, for example, be facilitated by neurochemical production and/or resulting availability for such neurochemicals as a therapeutic or therapeutic delivery mechanism. This production and/or availability may, for example, be being produced in an environment designed to keep the patient engaged in gaming play. For example, the delivery of the treatment protocol may be configured such that the patient may be able to readily identify the treatment mechanism. Accordingly, various embodiments may advantageously promote an ongoing unconscious learning state.

Various embodiments may work at a confluence of strong storytelling with integrated game mechanics and/or treatment mechanisms that unconsciously changes behavior and physiology through neurologic plasticity arriving at entrainment. For example, such embodiments may advantageously achieve subconscious neurological entrainment with a wildly effective positive reinforcement feedback loop.

Dopamine generation may, for example, correspond to a user's desire to repeat a therapy. Serotonin generation may, for example, correspond to a user's (positive) perception about having performed the therapy. Various embodiments may identify, generate, and/or deliver medicinal media according to (predetermined) criteria corresponding, for example, to dopamine oxytocin, endorphins, and/or serotonin generation. Accordingly, various embodiments may provide therapy using medicinal media that induces a positive perception of the therapy in the user and/or a desire to repeat the therapy. Accordingly, various embodiments may advantageously (drastically) improve patient compliance. Various embodiments may, for example, advantageously provide patient-desired therapy as opposed to therapy which the patient must force themselves to undertake.

Figure 3:
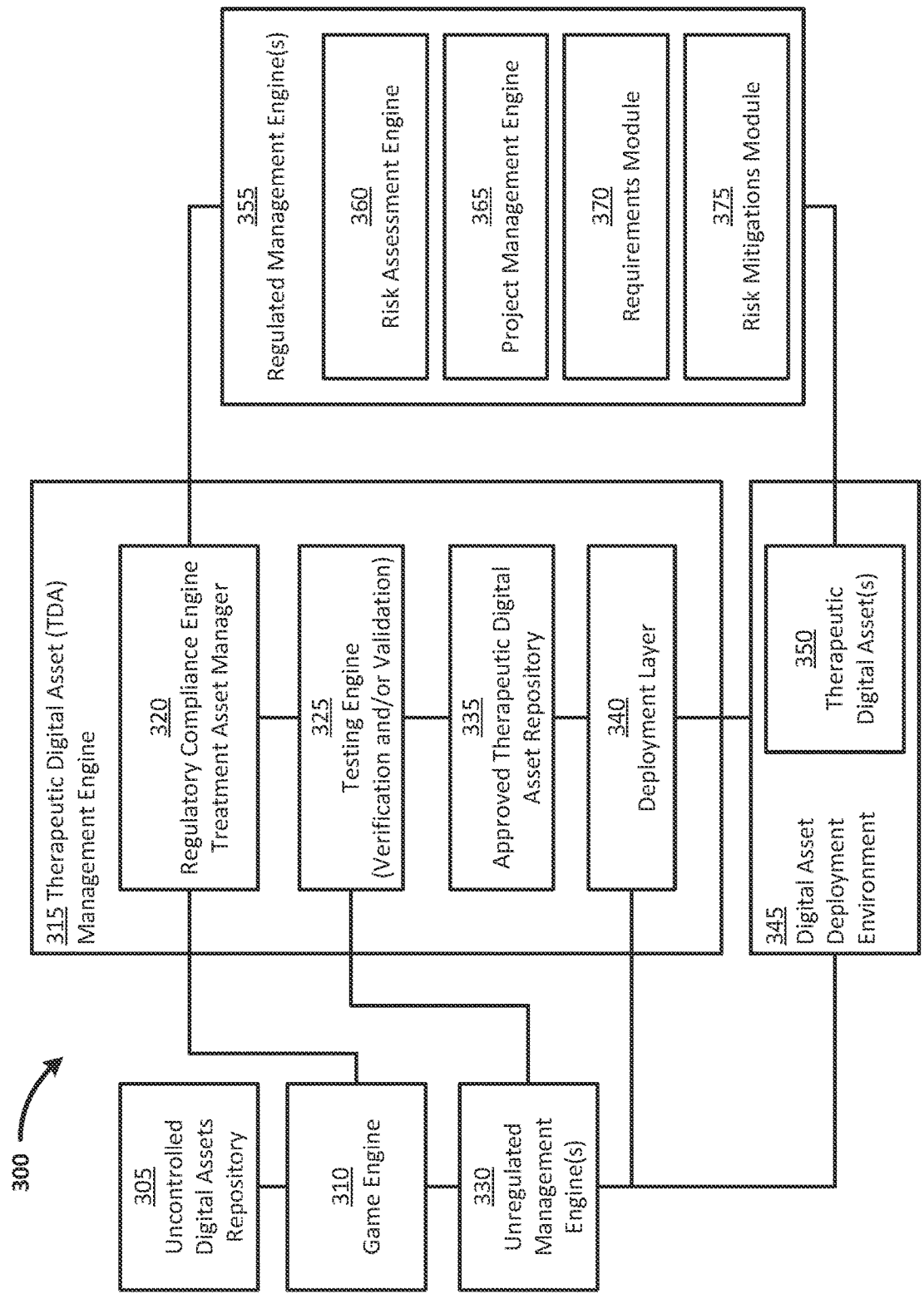
FIG. 3 depicts a block diagram of an exemplary TDA management engine in an exemplary use case for use with a game engine.

FIG. 3 depicts a block diagram of an exemplary TDA management engine in an exemplary use case for use with a game engine. In the depicted example, a therapeutic digital content management and delivery system 300 includes a repository 305 of uncontrolled digital assets. The repository 305 may include, by way of example and not limitation, software modules, digital media, or some combination thereof. For example, the repository 305 may include at least some components of a digital videogame. In some embodiments, the NMDAs in the repository 305 may, by way of example and not limitation, include physics engines (e.g., light engine, particle engine, motion engine), rendering engines, modelling engines, or some combination thereof. In some embodiments, the NMDAs in the repository 305 may, for example, include media (e.g., backgrounds, images, music, themes). In some embodiments the NMDAs in the repository 305 may, for example, include characters.

The repository 305 is operatively coupled to a game engine 310. The game engine 310 may, for example, provide a framework deploying NMDAs from the repository 305 into one or more games. The game engine 310 is operatively coupled to a therapeutic digital asset (TDA) management engine (TDAME 315). The TDAME 315 includes a regulatory compliance engine treatment asset manager (therapeutic asset manager 320). The therapeutic asset manager 320 is operably coupled to the game engine 310. For example, the therapeutic asset manager 320 may manage development and/or deployment of TDAs via the game engine 310. The therapeutic asset manager 320 may, for example, receive NMDAs from the repository 305 the game engine 310. The therapeutic asset manager 320 may, for example, evaluate NMDAs from the repository 305 to identify TDAs. The therapeutic asset manager 320 may, for example, generate TDAs. The therapeutic asset manager 320 may, for example, receive TDAs from an external source(s) (e.g., third-party therapeutic asset developers).

The TDAME 315 further includes a testing engine 325. The testing engine 325 is operably coupled to the therapeutic asset manager 320. The testing engine 325 may, for example, generate and/or apply testing profiles to the TDAs managed by the therapeutic asset manager 320.

The testing engine 325 is operably coupled to an unregulated management engine 330. The unregulated management engine 330 may, for example, include project management software. The unregulated management engine 330 may include, by way of example and not limitation, game development modules. For example, the unregulated management engine 330 may include a game development environment (GDE). The unregulated management engine 330 is operably coupled to the game engine 310. For example, the unregulated management engine 330 may be configured to manage development and/or deployment of a videogame using NMDAs from the repository 305 via the game engine 310.

The TDAME 315 further includes an approved therapeutic digital asset repository (TDA repository 335). The TDA repository 335 is operatively coupled to the testing engine 325. For example, the TDA repository 335 may receive TDAs from the testing engine 325 which have been approved after verification and/or validation testing.

The TDAME 315 further includes a deployment layer 340. The deployment layer 340 is operably coupled to the TDA repository 335. The deployment layer 340 is further operably coupled to the unregulated management engine 330. For example, the unregulated management engine 330 may include TDAs from the TDA repository 335 via the deployment layer 340. TDAs being used (e.g., in development, pre-deployment, after deployment) in the unregulated management engine 330 (e.g., being incorporated via the game engine 310 and/or unregulated management engine 330 with NMDAs from the repository 305) may be retrieved from the TDA repository 335 via the deployment layer 340. The deployment layer 340 may, for example, associate and/or monitor metadata structures of the TDAs when the TDAs are deployed outside of the TDAME 315. Accordingly, the TDAs may be advantageously verified and/or validated in a non-medical environment (e.g., non-regulated, non-verified, non-validated) environment.

The unregulated management engine 330 and the deployment layer 340 are operably coupled to a digital asset deployment environment (DADE 345). The DADE 345 may, for example, include a videogame. The DADE 345 may, for example, include a videogame delivery network and/or device(s). The DADE 345 may, for example, include therapeutic digital assets (TDAs 350) deployed in the DADE 345. The TDAs 350 may, for example, be managed, from a development aspect, by the unregulated management engine 330 (e.g., integration with NMDAs from the repository 305, association with the game engine 310). The TDAs 350 may, for example, be managed, from a risk analysis and mitigation aspect, by the deployment layer 340 of the TDAME 315.

For example, the deployment layer 340 may maintain (ultimate) control of an activation state of the TDAs 350. The deployment layer 340 may monitor for changes in the DADE 345. In response to changes, the deployment layer 340 may cause testing (e.g., by the testing engine 325) to be performed on the TDAs 350 and/or the DADE 345. The deployment layer 340 may deactivate the TDAs 350 until testing can be performed and/or upon unsatisfactory test results. In some embodiments, the deployment layer 340 may advantageously enable the TDAs 350 to be controlled such that verification and/or validation of the TDAs 350 are maintained in an uncontrolled DADE 345.

The therapeutic asset manager 320 is operably coupled to a regulated management engine 355. The regulated management engine 355 includes, in the depicted example, a risk assessment engine 360. The risk assessment engine 360 may, for example, assess risks of an NMDA being evaluated by the therapeutic asset manager 320. In some embodiments, the risk assessment engine 360 may, for example, apply a machine learning model(s) to the TDAs to determine corresponding risks. The risk assessment engine 360 may, for example, generate risk associated with the TDA. The risk assessment engine 360 may, for example, associate predetermined risks having a confidence interval within a (predetermined) range with the TDA. The risk assessment engine 360 may, for example, apply the model(s) to the TDAs based on historical associations between TDAs and risks. The risk assessment engine 360 may, for example, generate one or more displays to present the (generated, associated, potential) risks to a user for review, modification, rejection, and/or approval. The risk assessment engine 360 may, for example, generate associations (e.g., via metadata structures) between the TDAs and risks (e.g., in response to the user input received).

The regulated management engine 355 includes a project management engine 365. The project management engine 365 may manage documents, deliverables, timelines, or some combination thereof related to TDAs.

The regulated management engine 355 includes a requirements module 370. The requirements module 370 may receive, maintain, apply, and/or generate files (e.g., metadata structures) corresponding to regulated requirements. For example, the requirements module 370 may include risk requirements. The requirements module 370 may associate risk requirements (e.g., risk analysis, risk mitigation, reporting) corresponding to TDAs.

The TDA repository 335 includes a risk mitigation module 375. The risk mitigation module 375 may include associations between TDAs, risks, and corresponding risk mitigations. The risk mitigation module 375 may, for example, receive risk mitigations from a user (e.g., quality engineer). The risk mitigation module 375 may, for example, generate risk mitigations associated with a risk corresponding to a TDA. The risk mitigation module 375 may, for example, automatically associate existing risk mitigations with risks associated with the TDA. For example, the risk mitigation module 375 may apply a machine learning model(s) to associate risk mitigations having a confidence interval within a predetermined range with a TDA based on (predetermined) risks. The risk mitigation module 375 may, for example, apply the model to generate risk mitigation associations based on historic associations between TDAs, risks, and/or risk mitigations. The risk mitigation module 375 may, for example, generate one or more displays to present the (generated, associated, potential) risk mitigations to a user for review, modification, rejection, and/or approval. The risk mitigation module 375 may generate associations (e.g., via metadata structures) between the TDAs, risks, and/or (approved) risk mitigations (e.g., in response to the user input received).

Figure 4:
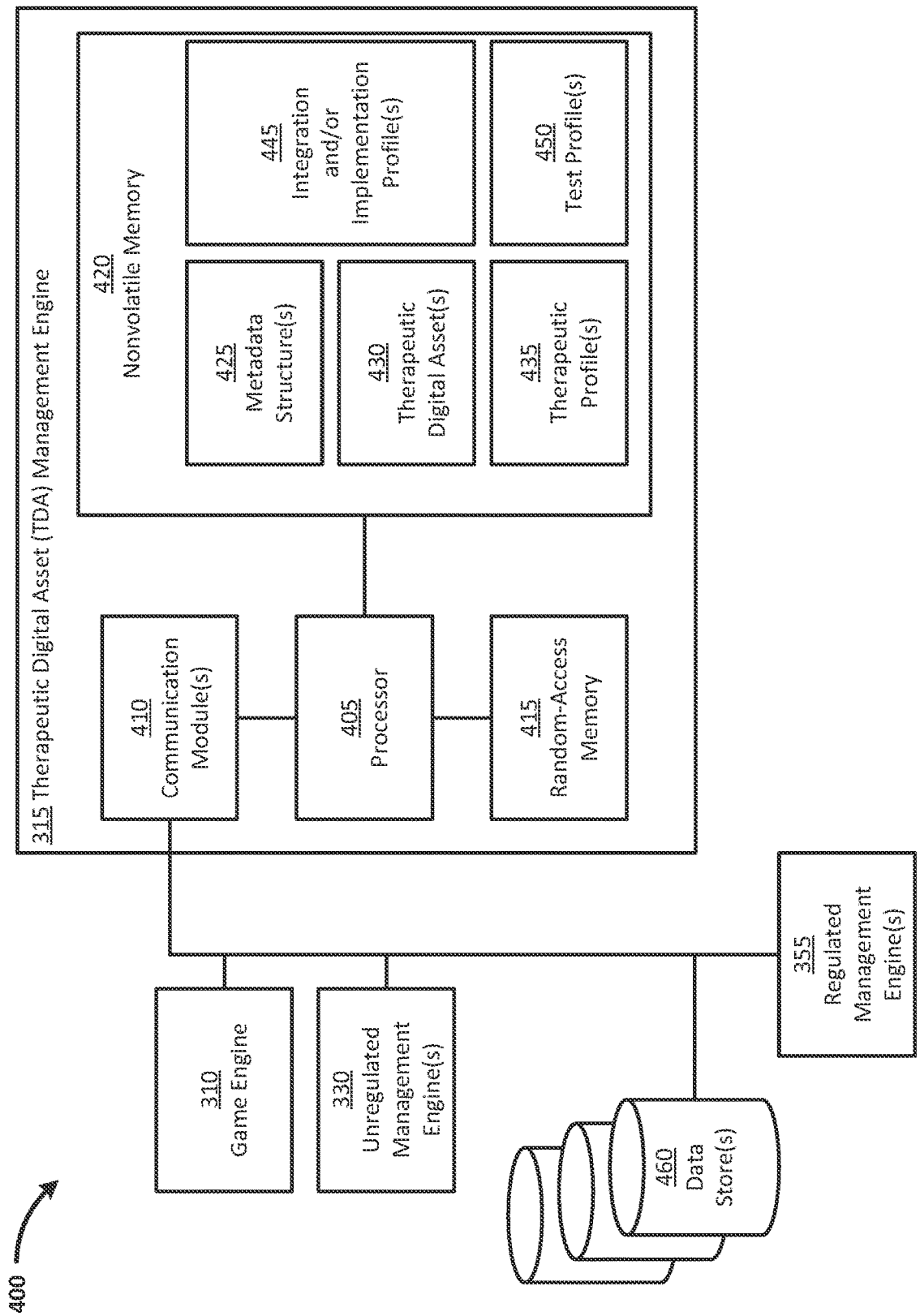
FIG. 4 depicts a block diagram of the exemplary TDA management engine.

FIG. 4 depicts a block diagram of the exemplary TDA management engine. In an exemplary TDAM system 400, the TDAME 315 includes a processor 405. The processor 405 may, for example, include one or more processors. The processor 405 is operably coupled to a communication module 410. In the depicted example, the communication module 410 is operably coupled to the game engine 310, the unregulated management engine 330, and the regulated management engine 355. The The processor 405 is operably coupled to a random-access memory module 415. The random-access memory module 415 may, for example, include one or more random-access memory (RAM) modules.

The processor 405 is operably coupled to a nonvolatile memory module 420. The nonvolatile memory module 420 may, for example, include one or more nonvolatile memory (NVM) modules. The nonvolatile memory module 420 may, for example, include one or more programs of instructions configured to be executed by the processor 405. At least one program of instructions may, for example, be configured such that, when executed by the processor 405, the processor 405 performs quality management operations to manage TDAs in a non-medical environment.

The nonvolatile memory module 420 includes, in the depicted example, at least one metadata structure module 425. The at least one metadata structure module 425 may, by way of example and not limitation, include metadata structures associated with one or more TDAs, such as, for example, disclosed at least with reference to FIG. 3.

The nonvolatile memory module 420 includes, in the depicted example, at least one therapeutic digital asset module 430. The at least one therapeutic digital asset module 430 may, for example, include one or more TDAs (e.g., the TDAs 350, TDAs associated with the TDA repository 335).

The nonvolatile memory module 420 includes, in the depicted example, at least one therapeutic profile module 435. The at least one therapeutic profile module 435 may, by way of example and not limitation, include one or more therapeutic profiles. A therapeutic profile may, for example, associate at least one therapeutic modality and/or therapeutic mechanic with at least one corresponding attribute(s). In various embodiments, a therapeutic profile may, for example, include at least one criterion (e.g., parameter, threshold, range, physiological metric) associated with a therapeutic mechanic and/or modality. For example, a therapeutic profile may include attributes and/or values configured to identify a TDA. A therapeutic profile may, for example, include attributes and/or values configured to generate a TDA. In some embodiments a therapeutic profile may include attributes and/or values configured to evaluate a TDA.

The nonvolatile memory module 420 includes, in the depicted example, at least one integration profile module 445. The at least one integration profile module 445 may, by way of example and not limitation, include one or more integration and/or implementation profiles.

In various embodiments integration profiles may include game integration profiles (GIPs). GIPs may, for example, include parameters and/or other criteria and/or instructions configured to control integration of a TDA within a game. The TDA may, for example, be associated with one or more therapeutic mechanics and/or modalities.

In various embodiments, integration profiles may include asset integration profiles. An asset integration profile (AIP) may, for example, include parameters, criteria, and/or instructions configured to deliver one or more digital assets via a digital carrier. An AIP in the at least one integration profile module 445 may, for example, be associated with a TDA.

In various embodiments, integration profiles may include carrier integration profiles (CIPs). For example, a CIP may include parameters, criteria, and/or instructions configured to deliver a therapeutic mechanic and/or modality via a digital carrier. A digital carrier may include at least one digital asset (e.g., TDA).

The nonvolatile memory module 420 includes, in the depicted example, at least one test profile module 450. The at least one test profile module 450 may, for example, include one or more test profiles. For example, the test profiles may be generated, retrieved, stored, or some combination thereof, by the testing engine 325.

The processor 405 is operably coupled to at least one data store 460 by the communication module 410. The at least one data store 460 may, for example, include local and/or remote data storage devices. In various embodiments the at least one data store 460 may, for example, receive, transmit, and/or store data from the nonvolatile memory module 420. For example, the TDAME 315 may transmit data to the at least one data store 460 from the random-access memory module 415 and/or the nonvolatile memory module 420 via the communication module 410 and the processor 405. The TDAME 315 may, for example, receive data from the at least one data store 460 to the random-access memory module 415 and/or the nonvolatile memory module 420 via the communication module 410 and the processor 405.

In some embodiments the at least one data store 460 may, for example, include tangible media. The tangible media may, for example, include standalone media (e.g., compact disk, USB drive). The tangible media may, for example, be embodied in a computing device. The computing device may, for example, include a server. The computing device may, for example, include a personal computing device (e.g., general-purpose computer). The personal computing device may, for example, include a gaming device. The personal computing device may, for example, include a mobile computing device (e.g., smartphone, tablet, laptop, smart watch, smart glasses). In some embodiments the computing device may, for example, include an Internet of things (IoT) device. In some embodiments the commuting device may, for example, include a medical device.

Figure 5:
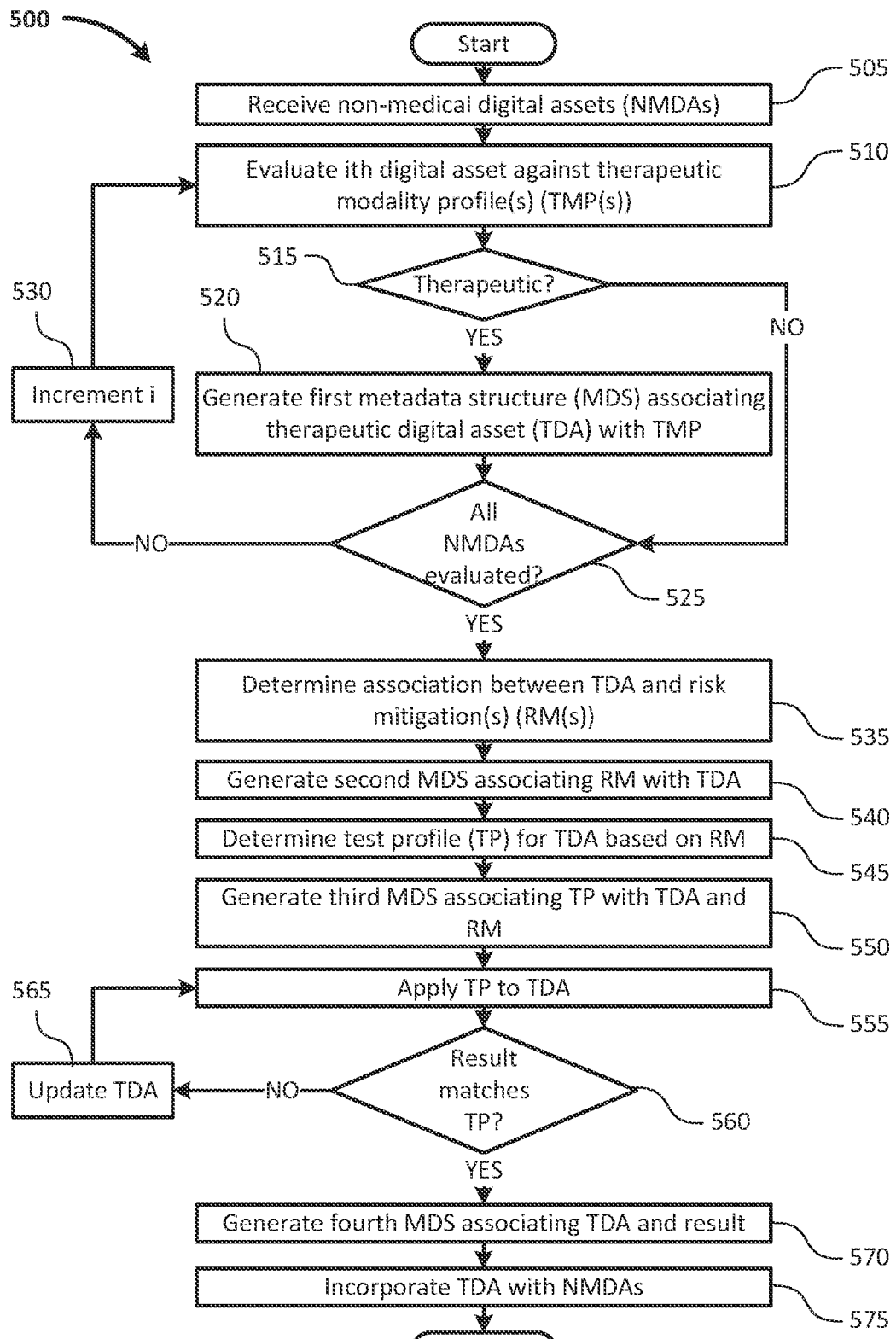
FIG. 5 depicts an exemplary method of generating TDAs from non-medical digital assets.

FIG. 5 depicts an exemplary method of generating TDAs from non-medical digital assets. A method 500 begins with a step 505 of receiving nonmedical digital assets (NMDAs). The method 500 may, for example, be performed by the TDAME 315 (e.g., at least partially be the processor 405 based on a program(s) of instructions tangible embodied on the nonvolatile memory module 420). For example, the NMDAs may be retrieved, by way of example and not limitation, from the repository 305.

In a step 510, an ith NMDA (where i is an index variable) is evaluated against one or more therapeutic modality profiles (TMPs). The NMDA may, for example, be evaluated by the therapeutic asset manager 320 and/or the testing engine 325.

In some embodiments the therapeutic asset manager 320 and/or testing engine 325 may cause display(s) to be generated and presented to a user for evaluation of the NMDA. In some embodiments, a TMP may be retrieved and presented to a user with a corresponding NMDA. In some embodiments, the display may include attributes of the NMDA associated with the TMP. In some embodiments, a machine learning model may, for example, be applied to automatically identify associated TMPs with an NMDA based at least on historical associations between TMPs and NMDAs. In some such embodiments, the resulting (proposed) associations may be presented to a user by generating one or more displays with, for example, the TMP, the NMDA, and an indication of confidence and/or associated attributes.

If, in a decision point 515, it is determined that the NMDA is therapeutic (or associated with a therapeutic modality), then a first metadata structure (MDS) is generated in a step 520. The MDS may associate the NMDA with the corresponding TMP. The NMDA may, for example, be considered a TDA based on the association. The NMDA may, for example, be considered a TDA when associated with the first MDS (e.g., linked, integrated with). In some embodiments the metadata structure may be inserted into the NMDA to generate the corresponding TDA. In some embodiments the metadata structure may be stored in a separate structure and linked with the NMDA to generate the corresponding TDA.

If it is determined in the decision point 515 that the NMDA is not therapeutic and/or associated with a therapeutic modality, then the method 500 moves to a decision point 525 to move on to a next NMDA.

If it is determined in the decision point 525 that all NMDAs have not been evaluated, then the index variable (i) is incremented in a step 530 and the method 500 returns to the step 510. Once it is determined that all the NMDAs have been evaluated (in the decision point 525), then an association is determined between the TDA and at least one risk mitigation, in a step 535. The risk mitigation may, for example, be determined using the regulated management engine 355. In some embodiments, the risk mitigation may be determined manually. In some embodiments, the risk mitigation may be determined automatically.

Once the association(s) is determined, a second MDS is generated, in a step 540, associating the TDA with the corresponding risk mitigation. In some embodiments the second MDS may be a separate structure from the first MDS. In some embodiments the second MDS may be generated by updating the first MDS.

At least one test profile is determined for the TDA corresponding to the risk mitigation, in a step 545. The test profile may include at least one predetermined test input. The test profile may include at least one predetermined test operation. The test profile may include at least one predetermined approved test result (e.g., corresponding to application of the at least one test operation, corresponding to the at least one test input). For example, in an illustrative example corresponding to an exemplary TDA related to a breathing therapeutic modality, the test input may include a breathing input (e.g., breathing into a microphone at a certain rate). The operation may, for example, include detecting a breathing rate. The approved result may, for example, include a (detected) breathing rate within a (predetermined) approved range.

In some embodiments the test profile may, for example, be determined using the regulated management engine 355, the therapeutic asset manager 320, the testing engine 325, or some combination thereof. The test profile may, for example, be determined based on manual input. In some embodiments the test profile may, for example, be determined automatically. The test profile may, by way of example and not limitation, be generated to satisfy the risk mitigation for the TDA. The test profile may, for example, be selected from existing test profiles. The test profile may, for example, be stored in the at least one test profile module 450.

A third MDS is generated, in a step 550, associating the TDA with the test profile and the risk mitigation. In some embodiments the third MDS may be a separate structure from the first MDS and/or the second MDS. In some embodiments the third MDS may be generated by updating the second MDS.

The test profile is applied, in a step 555, to the TDA. For example, the test profile may be applied by the testing engine 325. In some embodiments application may be performed at least partially manually (as related to the illustrative breathing example, e.g., manually breathing into a test microphone). In some embodiments application may be performed at least partially automatically (as related to the illustrative breathing example, e.g., generating a predetermined breathing sound, automatically analyzing a detection signal for breathing rate, automatically comparing a breathing rate determined from a detection signal to an approved breathing rate).

If a result from applying the test profile to the TDA is determined, in a decision point 560, not to match the approved result defined by the test profile, then the TDA may be updated in a step 565. Updating the TDA may, for example, include generating an indication that the TDA has failed to meet the approved test results. Indication may, for example, be presented to a user on a generated display including an indication of at least one attribute and/or component of the TDA associated with the failure. In some embodiments updating the TDA may, for example, include automatically adjusting attributes and/or components of the TDA (e.g., based on the test results and/or the approved test results) to bring the TDA and the compliance.

Once it is determined in the decision point 560 that the TDA test result(s) from the step 555 matches the approved test result(s) of the test profile, then a fourth MDS is generated in a step 570. The fourth MDS associates the TDA with the test result. In some embodiments the fourth MDS may further associate the TDA with the test profile. The fourth MDS may, for example, be generated by updating the third MDA. In some embodiments the fourth MDS may, for example, be independent of the first MDS, the second MDS, and/or the third MDS.

In a step 575, the TDA is incorporated with the NMDAs (e.g., from the step 505). For example, the TDA may be deployed via the deployment layer 340. In some embodiments the TDA may be included in the TDA repository 335. In some embodiments the TDA may, for example, be released into an unregulated management engine 330 (e.g., a game development environment). In some embodiments the TDA may, for example, be incorporated into a DADE 345.

Accordingly, various embodiments may advantageously permit digital assets to be created and/or converted into TDAs. The TDAs may, for example, be verified and/or validated. In some embodiments the method 500 may be applied to NMDAs in a development environment (e.g., during development of a videogame, such as in a GDE). In some embodiments the method 500 may, for example, be applied to NMDAs in a deployment environment (e.g., to identify TDAs in an existing videogame). Accordingly, various embodiments may advantageously allow only therapeutic components to be isolated in a non-medical environment. The therapeutic components may be configured to be managed according to regulatory verification and/or validation (VV) protocols, while releasing non-therapeutic components to be managed in a nonregulated (e.g., non-medical) environment.

In some embodiments the step 505 may, for example, receive only one NMDA. For example, an NMDA may include a proposed TDA. A therapeutic developer may, for example, create a new (proposed) TDA. The proposed TDA may be evaluated according to the method 500 to VV the proposed TDA as a verified and/or validated TDA.

Figure 6:
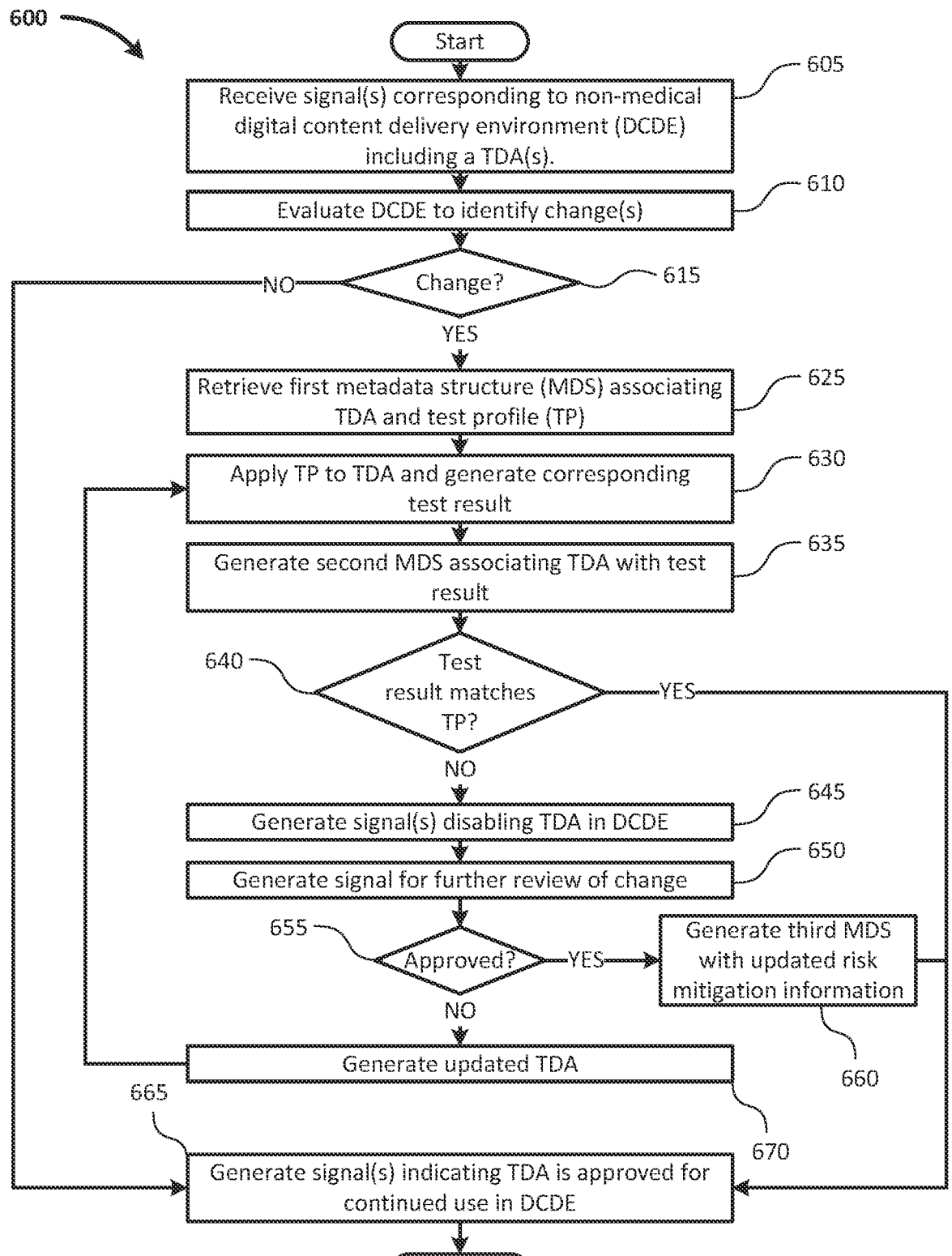
FIG. 6 depicts an exemplary method of managing TDAs in a non-medical digital content delivery environment (DCDE).

FIG. 6 depicts an exemplary method of managing TDAs in a non-medical digital content delivery environment (DCDE). A method 600 may, for example, be performed by the TDAME 315 (e.g., at least partially be the processor 405 based on a program(s) of instructions tangible embodied on the nonvolatile memory module 420). In some embodiments various operations may, by way of example and not limitation, be performed by the therapeutic asset manager 320, the testing engine 325, the deployment layer 340, the regulated management engine 355, or some combination thereof.

In the method 600, a signal(s) received in the step 605. The signal corresponds to at least one nonmedical digital content delivery environment (DCDE) including at least one TDA. The DCDE may, for example, correspond to a GPOS. The DCDE may, for example, correspond to a videogame. For example, the DCDE may include at least some portion of the DADE 345.

In various embodiments the signal may be received in the step 605 based on manual input (e.g., a proposed change). In some embodiments the signal may be received automatically. For example, the signal may be received in response to a user attempting to deploy and/or activate the DCDE in a therapeutic context. In some embodiments the signal may be received by virtue of being automatically generated. For example, the signal may be generated in response to automatic monitoring of the DCDE (e.g., according to one or more predetermined triggers, such as schedule, operation system version, test points).

The DCDE is evaluated to identify a change(s) in a step 610. For example, the DCDE may be evaluated based on the signal received. In some embodiments the DCDE may be evaluated in response to receiving the signal. For example, a DCDE may be at least partially manually evaluated in response to receiving the signal. In some embodiments the DCDE may be at least partially automatically evaluated (e.g., determining one or more predetermined attributes, comparing the predetermined parameters to previously stored (approved) historical attributes). In some embodiments at least one display may be generated (e.g., by review by a human) containing historic and current (predetermined) attributes of the DCDE. In some embodiments the display may further include one or more risk mitigations and/or risks associated with the TDA(s) (e.g., retrieved based on associated MDS(s)).

If a change is determined to be identified in a decision point 615, then a first MDS is retrieved in a step 625. The first MDS may associate the TDA with at least one test profile. The test profile is applied to the TDA (e.g., independently, in the context of the DCDE) in a step 630. In some embodiments the test profile may be applied at least partially manually. For example, a display may be generated prompting a user to apply the test profile to the TDA and/or the DCDE. The display may, for example, include one or more test inputs, test operations, and/or (approved) test results associated with (e.g., defined by) the test profile. The display may, for example, from the user to provide one or more inputs associated with a result of application of the test profile to the TDA and/or the DCDE.

In some embodiments the test profile may be applied at least partially automatically. For example, the test operations may be applied to the TDA and/or the DCDE using the test input(s). A test result(s) may be automatically determined. Corresponding test results based on the application may be automatically compared to (approved) test results.

A second MDS is generated in a step 635. The second MDS is generated based on the result(s) of the application of the test profile to the TDA in the step 630. The second MDS may associated the TDA with the test result(s) from the step 630. In some embodiments the second MDS may, for example, be generated by updating an existing MDS. For example, the second MDS may be generated by updating the first MDS. In some embodiments the second MDS may be generated as a separate structure (e.g., from the first MDS).

If it is determined, in a decision point 640, that the test result(s) generated in the step 630 does not match the test profile (e.g., does not correspond to at least one predetermined approved test result(s)), and the signal is generated in a step 645. The signal may be configured to induce disablement of the TDA in the DCDE. For example, the signal may deactivate the TDA. In some embodiments the signal may cause the TDA to be disabled for therapeutic use but remain active for non-therapeutic purposes. In some such embodiments, the TDA may be converted to an NMDA while disabled/deactivated. In some embodiments at least one therapeutic component of the TDA may be disabled, but at least one non-therapeutic component may remain available for use.

In some embodiments the signal may be automatically generated (e.g., in response to the test results, in response to a signal from a human indicating that the test results do not match the test profile). In some embodiments the signal may be manually generated (e.g., in response to input from a human indicating that the TDA should be disabled, at least in the context of the DCDE).

The signal is generated in the step 650 for further review of the change. For example, the signal may cause a display to be generated and presented to a user (e.g., a reviewer, quality engineer). The display may, for example, include the test result(s), the approved test result(s), the change, or some combination thereof.

If it is determined, in a decision point 655, that the change is approved, then a third MDS is generated in a step 660. The change may, for example, be approved by a human reviewer. The change may, for example, be approved based on further (automatic, manual) testing. The third MDS may, for example, include an updated risk(s). The third MDS may, for example, include an updated risk mitigation(s). In some embodiments the third MDS may include an updated test profile(s). The third MDS may, for example, include multiple MDSs. In some embodiments the third MDS may be separated of the first MDS and/or the second MDS. In some embodiments the third MDS may be generated, for example, by updating the first MDS. In some embodiments the third MDS may be generated, for example, by updating the second MDS.

A signal is then generated, in a step 665, indicating that the TDA is approved (e.g., verified, validated) for (continued) use in the DCDE. The TDA may, for example, be re-activated and/or re-enabled in response to the signal.

If, in the decision point 655, it is determined that the TDA is not approved (e.g., the change has violated a risk, a risk mitigation is no longer applicable, a therapeutic modality is no longer functional and/or safe), then an updated TDA is generated in a step 670. In some embodiments the TDA may be updated manually. For example, a display may be generated including an indication of the TDA, the change, and/or the (failed) test results (e.g., compared to the test profile). In some embodiments the display may further include an indication(s) of the risk(s) and/or risk mitigation(s) associated with the TDA (e.g., also associated with the change and/or DCDE). The display may prompt a user (e.g., developer, reviewer, engineer) to provide input on an updated TDA. The prompt for input may include prompt(s) to associate the change(s) to the TDA with the change to the DCDE, the risk(s), the risk mitigation(s), the test profile, the test result(s), or some combination thereof.

In some embodiments the updated TDA may, by way of example and not limitation, be at least partially automatically generated. For example, (previously approved) alterations may be applied based on the change, risk(s), risk mitigation(s), test profile, second MDS, or some combination thereof. In some embodiments alterations to the TDA may be automatically generated and provided as suggestions (e.g., in one or more display) to a user.

Once the updated TDA is generated, the method 600 returns to the step 630 to test the updated TDA. Once result(s) of applying the test profile to the (updated) TDA is determined to match the test profile (in the decision point 640), and the signal(s) indicating the TDA is approved for use in the DCDE (when applicable) in the step 665, the method ends.

Various embodiments may advantageously monitor a TDA in a non-therapeutic (e.g., non-regulated) environment. In some embodiments the method 600 may, for example, be applied to validate a (proposed) TDA. In some embodiments the method 600 may, for example, be applied to verify a (existing) TDA. In some embodiments the method 600 may be applied to a TDA in a development environment (e.g., during development of a videogame, such as in a GDE). In some embodiments the method 600 may be applied to a TDA in a deployment environment (e.g., in a videogame).

In the depicted example the signal may be generated in the step 665 in response to a determination in the decision point 615 that no change occurs. In some embodiments, no signal may be generated in response to no change being detected. For example, the TDA may continue to be active in the DCDE unless a negative signal is received (e.g., in the step 645).

In some embodiments a (provisional) negative signal may be received immediately after determining in the decision point 615 that a change has occurred. For example, the TDA may be (temporarily) deactivated and/or disabled immediately while testing (e.g., in the step 630) is being performed. Such embodiments may advantageously maintain heightened safety.

In some embodiments, the step 650, the decision point 655, and/or the step 660 may be omitted. For example, further review may be unnecessary (e.g., automatically performed, already performed manually in the step 635 and/or in association with the decision point 640). Accordingly, some embodiments may, for example, proceed directly from the decision point 640 to the step 670.

Figure 7:
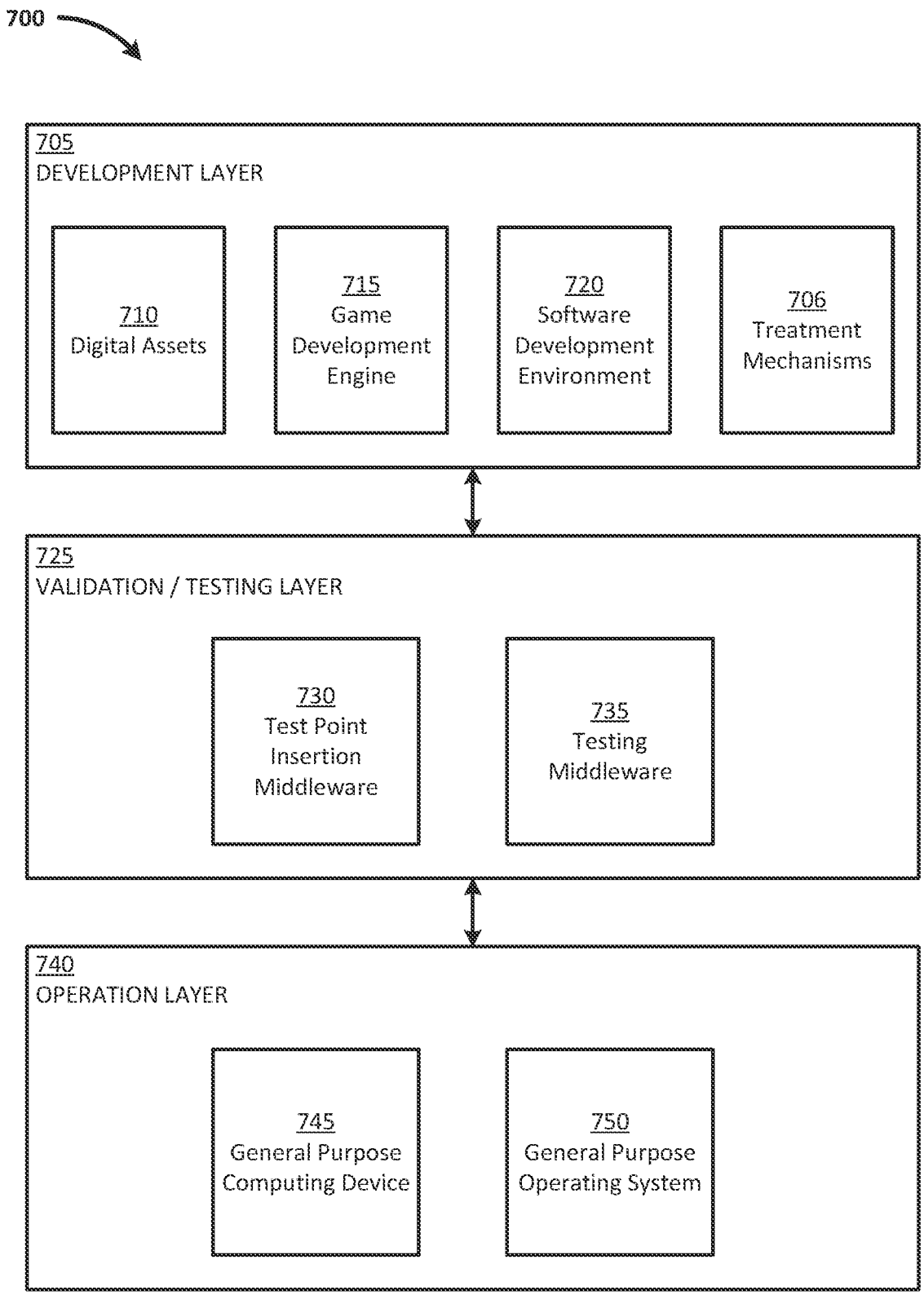
FIG. 7 depicts a block diagram of an exemplary middleware engine in an exemplary use case for validation and testing of code generated in a non-medical development layer for use in a medical operation layer.

FIG. 7 depicts a block diagram of an exemplary middleware engine in an exemplary use case for validation and testing of code generated in a non-medical development layer for use in a medical operation layer. Conventional code is generated in a development layer 705. The conventional code is transformed into verifiable and/or validatable and/or verifiable and/or validatable code and tested in a validation/testing layer 725. Verified and/or validated code is executed in an operation layer 740 on general purpose computing devices (GPCDs) running general purpose operation systems (GPOSs). Various embodiments may, by way of example and not limitation, advantageously automatically manage one or more aspects of transforming conventional code into verifiable and/or validatable code, validating combinations of verified and/or validated code with GPOSs, and (regression) testing of updates to verifiable and/or validatable code or GPOSs, or some combination thereof.

In the depicted exemplary embodiment, development layer 705 includes treatment mechanisms 706, digital assets 710, game development engine (a GDE(s) 715), and software development environment (SDE 720). The treatment mechanisms 706 may include, for example, pre-existing software modules for therapeutic mechanisms. The treatment mechanisms 706 may include predetermined therapy profiles. A developer may, for example, make use of the treatment mechanisms 706 to repurpose the digital assets 710 into a digital asset delivery vehicle (e.g., a video game) for therapeutic and/or enhancement use. In some implementations, the developer may access (predetermined) functions provided by the treatment mechanisms 706 by accessing through an application programming interface (API) of a treatment library and/or system. For example, the treatment mechanisms 706 may be a control mechanism that enable a user to use his/her breathing pattern to control a character in a video game. In some examples, the treatment mechanisms 706 may be developed according to health and medical rules and regulation and may be certified compliant with relevant governing bodies.

In various embodiments treatment mechanisms, treatment mechanism libraries, and/or control systems may, for example, be at least partially implemented as disclosed at least with reference to U.S. Application Ser. No. 63/172,379, titled "DEEPWELL DIGITAL THERAPEUTIC CONCEPT," filed by Ryan J. Douglas, et al., on Apr. 8, 2021; U.S. Application Ser. No. 63/260,128, titled "Patient Compliance-Inducing Digital Therapeutic Game Mechanics," filed by Ryan J. Douglas, et al., on Aug. 10, 2021; U.S. Application Ser. No. 63/202,881, titled "Immersive Digital Therapy," filed by Ryan J. Douglas on Jun. 28, 2021; and/or U.S. Application Ser. No. 63/203,058, titled "Management and Validation of Distributed Implementation of Treatment Modules," filed by Ryan J. Douglas, et al., on Jul. 6, 2021, the entire contents of which applications are incorporated herein by reference.

The digital assets 710 may include, by way of example and not limitation, images, code snippets, modules, audio files, parameter and configuration files, methods, objects, other appropriate assets, or some combination thereof. Code assets and other common modules and outputs may be provided for example, from a source such as the GDE(s) 715. Such sources may, by way of example and not limitation, include common game engines such as Unreal (developed by Epic Games, Inc. of Cary, NC) and/or Unity (developed by Unity Technologies, Inc., headquartered in San Francisco, CA). In one example, a developer may integrate or combine the treatment mechanism 706 and the digital assets 710 to create a treatment asset for medical or training purposes.

In some embodiments the digital assets may, for example, include video files. The digital assets may include images. The digital assets may include text (e.g., novels, histories, biographies, educational texts). The digital assets may include puzzles (e.g., digital puzzles). The digital assets may include audio (e.g., speaking, reading, music). The digital assets may include color schemes. The digital assets may include three-dimensional digital files (e.g., shapes, assemblies, environments).

Validation and testing layer 725 includes test point insertion middleware (TPIM 730) and testing middleware (TM 735). TPIM 730 may, by way of example and not limitation, perform automated processes on code generated or modified in development layer 705. By way of example and not limitation, at least one automated process may include addition of check sums to common modules or other assets, generation of unit tests, and/or other validation-related processes. The TM 735 may, for example, use the automated processes to confirm equivalent functions after release or modification of the code or the coding environment (e.g., in development layer 705), or the GPCD(s) or GPOS(s) from operation layer 740, or some combination thereof.

In some embodiments, testing may include one or more processes configured to verify that digital assets (e.g., therapeutic components) meet (predetermined) requirements. The requirements may, for example, be determined based on (predetermined) risks. The requirements may, for example, be determined based on (predetermined) risk mitigations (e.g., associated with one or more corresponding risks and/or digital asset). In some embodiments testing may, for example, verify that the digital asset conforms the requirement(s).

In some embodiments testing may, for example, validate that the digital asset(s) are therapeutic. For example, the testing may validate that the digital asset(s) achieves a desired therapeutic effect (e.g., target heart rate, target dopamine release, target behavior modification). The testing may, for example, validate that the digital asset(s) operates within a (predetermined) therapeutic range. A predetermined therapeutic range may, for example, include a min and/or max physiological parameter(s). A physiological parameter may, by way of example and not limitation, include heart rate. A physiological parameter may include respiration rate. A physiological parameter may include chemical release (e.g., dopamine, oxytocin, endorphins, serotonin).

In some embodiments, by way of example and not limitation, the testing may include regression testing. Regression testing may, for example, include applying one or more predetermined tests (e.g., associated with one or more risks, corresponding risk mitigations, and/or corresponding digital assets). The regression testing may, for example, validate and/or verify therapeutic components (e.g., therapeutic components, treatment assets).

In various embodiments, for example, one or more data stores (not shown) may be provided for storage and retrieval of test locations and results for future expansion and support of the software in a testable state. In various embodiments, automated processes may identify common modules and outputs from the source (such as common game engines, including but not limited to Unreal and Unity).

Operation layer 740 includes one or more GPCDs 745 running one or more GPOSs 750. Exemplary GPCDs may include, by way of example and not limitation, computers, tablets, smartphones, gaming devices and systems, embedded chip systems, integrated circuit systems, automation devices (e.g., open platforms such as Arduino, Raspberry Pi, or proprietary or closed source systems) other appropriate computing devices, or some combination thereof. Exemplary GPOSs may include, by way of example and not limitation, proprietary operating systems (OSs) (e.g., Microsoft Windows, Apple iOS, or specific hardware or industry-specific general-purpose OSs), open-source OSs (e.g., Unix, Linux, BSD, Arduino, Android), and general-purpose firmware (e.g., for ASICs, FPGAs, general purpose automation platforms, general purpose integrated circuits, and the like), or some combination thereof.

After verification and validation, some treatment assets that are repurposed from conventional digital media assets may be released to the user. These treatment assets may, in some implementations, be monitored to minimize risk and ensure safety for users.

Figure 8:
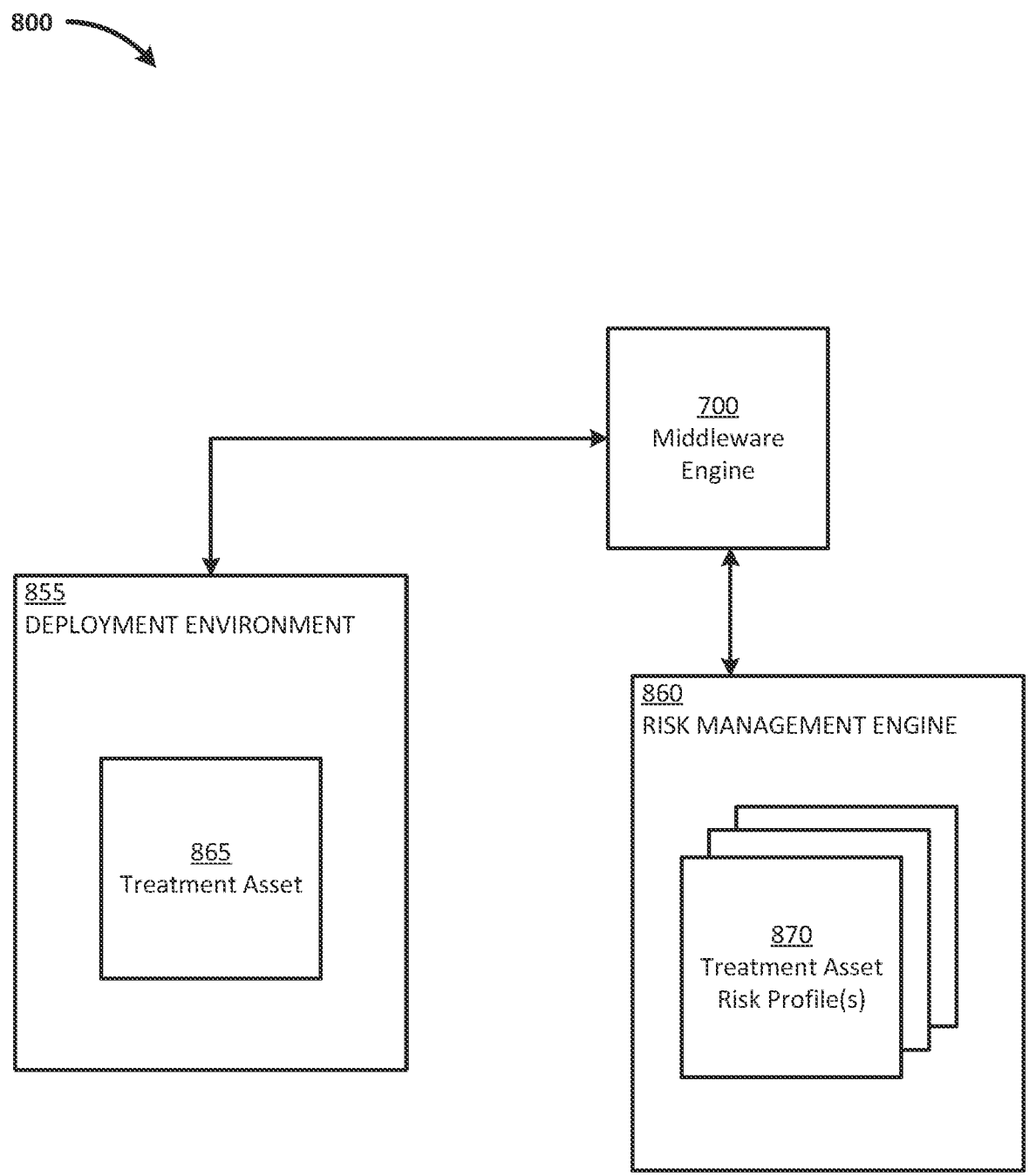
FIG. 8 depicts an exemplary system for monitoring the verification and/or validation of a treatment asset in a deployment environment.

FIG. 8 depicts an exemplary system for monitoring the verification and/or validation of a treatment asset in a deployment environment. In a depicted exemplary system 800, a deployment environment 855 is connected to the middleware engine 700 and a risk management event engine (RME 860).

In various embodiments, different forms of existing digital assets 710 may be used to develop in association with one or more treatment mechanisms 706 to create one or more treatment assets 865. In one example, a treatment asset 865 may be developed by embedding one or more treatment mechanisms 706 in one or more existing music asset (e.g., via a music delivery platform). As a result, for example, a music treatment asset may be verified and/or validated by the middleware engine and may provide therapeutic functions. In one example, the resulting treatment asset may be a dynamic song list that may calm an athlete before competition. For example, the digital asset(s) may be selected as stimulating dopamine and/or serotonin generation in the athlete. The digital asset(s) may be selected as being associated with a target (e.g., resting) heart rate range and/or with a target (e.g., resting) respiration range defined by the treatment mechanism. A delivery system may, for example, control delivery of the dynamic song list according to feedback (e.g., corresponding to physiological signals) received during delivery based on criteria (e.g., physiological parameters) defined in the treatment mechanism.

In another example, some treatment assets may be developed by combining a feature film with one or more treatment assets. As a result, for example, the feature film treatment asset may provide therapeutic functions. In one example, the resulting treatment asset may be an interactive feature film that may train a socially difficult person to interact with other people. The feature film may, for example, be selected as being associated with generation of desired physiological responses (e.g., dopamine oxytocin, endorphins, and/or serotonin generation). The feature film may, for example, be selected as being associated with a specific neurological and/or physical response. The film may, for example, be associated with inducing a neuroplastic state in one or more users. Accordingly, such embodiments may be configured to apply one or more therapeutic modalities embedded in and/or delivered concomitantly with the feature film to induce a shift from a habitual negative behavior to the development of a new positive behavior when presented with substantially similar stimuli or triggering events.

In the depicted example, treatment assets 865 may be provided with metadata defining verified and/or validated implementation parameters, verified and/or validated delivery parameters, and/or some combination thereof. According to these metadata, the RME 860 associated each of the treatment assets 865 with one or more treatment asset risk profiles (TARP 870). In some implementations, these TARP 870 may be generated or updated by the middleware engine during a validation process of the treatment asset. The TARP 870 may include, for example, details of a validation status of the associated treatment asset 865, a last verified and/or validated date, an identifier of the verified and/or validated version of related digital media asset, device in which the treatment asset 865 is verified to be used, or some combination thereof.

In some implementations, the RME 860 may evaluate the TARP 870 in association with a current metadata of the treatment assets 865. For example, the RME 860 may compare a latest updated time of the treatment asset 865 from current metadata, and the last verified and/or validated time as indicated by the TARP 870. If the last updated time is later than the last verified and/or validated time of the treatment asset, the RME 860 may determine that the current metadata does not match the verified and/or validated TARP, for example.

In response to determining the current metadata does not match a verified and/or validated risk profile, the RME 860 may determine, for example, that the implementation and/or current deployment environment of the treatment asset 865 is non-verified and/or validated and/or non-verified. In some examples, the RME 860 may then submit a report to the middleware engine 700 for re-validation and/or re-verification. The middleware engine 700 may generate notification to the system and/or one or more users. The middleware engine 700 may, for example, initiate an automated test state. The middleware engine 700 may deactivate (e.g., temporarily, provisionally) the treatment asset 865, or a combination thereof. Accordingly, the treatment asset 865 may advantageously be monitored for compliance with validation, verification, and/or regulatory requirements.

In various embodiments a risk management engine may generate one or more TARP according to at least one risk matrix. The risk matrix may, for example, associate one or more objects with one or more risks and/or risk mitigations. The risk matrix may, for example, be generated (e.g., automatically) by a risk matrix engine. The risk matrix engine may, for example, be configured to automatically perform a validation and/or verification check in response to detection of a change relative to the treatment asset 865 (e.g., as detected and/or reported by the middleware engine 700). In some embodiments the RME 860 may be at least partially implemented and/or in communication with a risk matrix engine such as disclosed at least with reference to U.S. application Ser. No. 16/423,981, titled "Quality Management Systems," filed by Ryan J. Douglas on May 28, 2019, the entire contents of which are incorporated herein by reference.

In some implementations, by using the middleware engine 700 and the RME 860, a developer may develop US Food and Drug Administration (FDA) compliant treatment assets 865 by using (non-FDA) approved digital media assets and the treatment mechanisms 706. For example, a conventional and/or pre-existing video game may be embedded with an FDA compliant breathing mechanism treatment asset. In one example, the resulting treatment asset may be FDA compliant and suitable for medical use because the treatment mechanism 706 is already regulated and approved by the FDA and/or is actively monitored for verified and/or validated use and/or use environment during deployment. A resulting treatment asset may, for example, include therapeutic reading delivery. A treatment asset may, for example, include therapeutic audio delivery. A treatment asset may, for example, include therapeutic film delivery.

Figure 9:
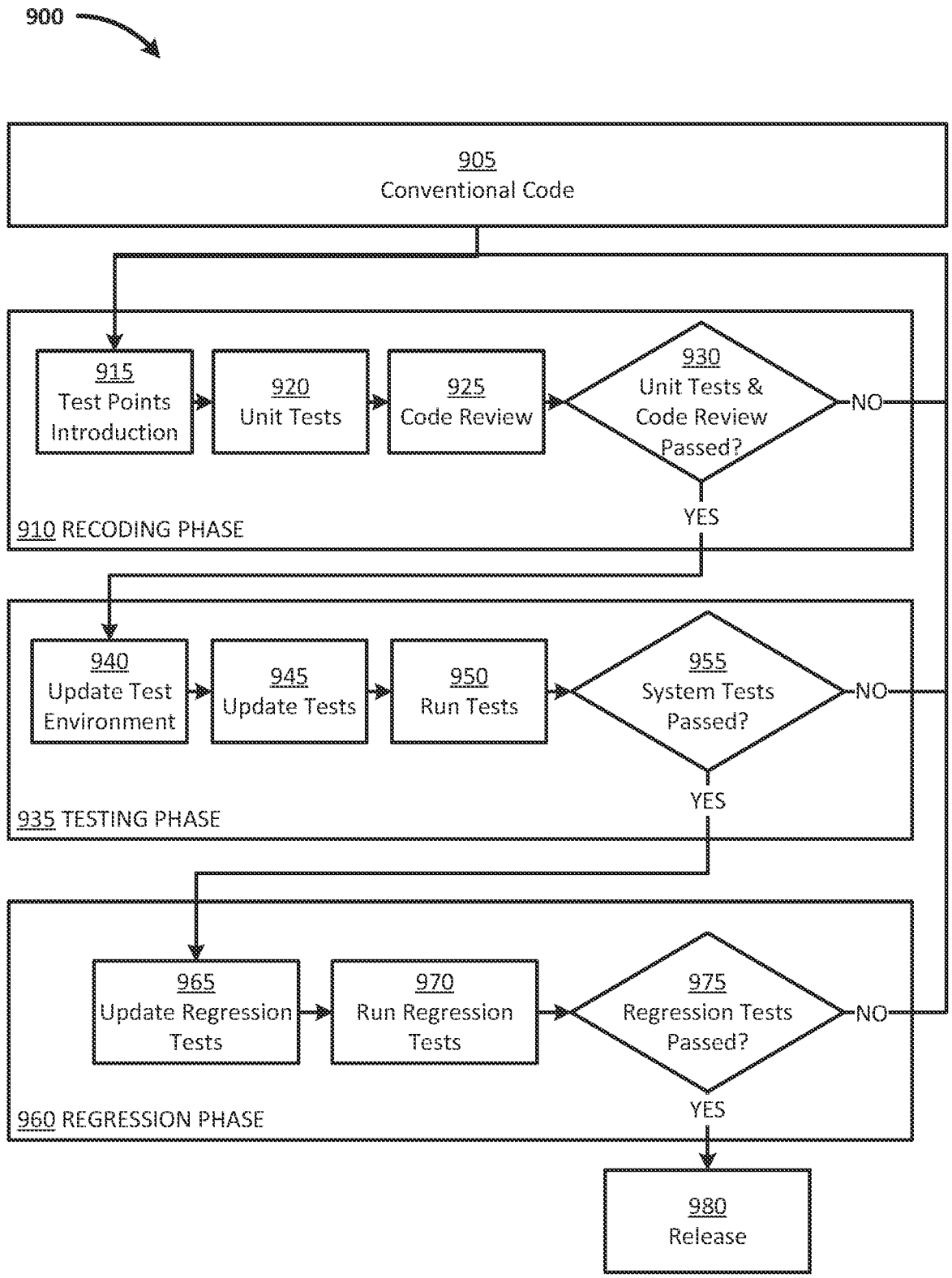
FIG. 9 depicts an exemplary method related to a middleware engine configured to introduce and execute test points and translate non-regression testable code to regression testable code.

FIG. 9 depicts an exemplary method related to a middleware engine configured to introduce and execute test points and translate non-regression testable code to regression testable code. In various embodiments the code may, for example, be a digital asset and/or be related to delivering a digital asset. In a method 900, initial conventional, non-verified and/or validated code 905 is retrieved or otherwise provided to initiate a recoding phase 910. The recoding phase 910 begins with introduction of test points in a step 915. The test points may, for example, be determined manually, automatically, or some combination thereof. The resulting code is tested by performing one or more unit tests in a step 920. The unit tests may, for example, be determined automatically, manually, or some combination thereof. The unit tests may, for example, be performed at one or more test points introduced in the step 915. The code resulting from step 915 is reviewed in a step 925. The code review may, for example, be manually, automatically, or both. The code review may include, for example, reviewing the results of one or more unit tests. If unit tests and code review are passed in a decision point 930, recoding phase 910 is complete. Otherwise, one or more steps of the recoding phase are repeated as necessary.

Once recoding phase 910 is complete, the code is now verifiable and/or validatable (e.g., capable of validation), and enters a testing phase 935. Testing phase 935 begins, in the exemplary method depicted, by updating a test environment in a step 940. The test environment may be updated, by way of example and not limitation, with updated unit tests, system tests, verifiable and/or validatable code, devices, OSs, or some combination thereof. System tests are updated in a step 945 and system tests are run in a step 950. The system steps are reviewed in a decision point 955. System tests may be, for example, determined, updated, and run automatically, manually, or some combination thereof. If system tests are not passed, the code returns to recoding phase 910 for, by way of example and not limitation, review and updating. If system tests are passed, testing phase is complete and the verifiable and/or validatable and tested code enters a regression phase 960.

In the exemplary depicted method, the regression phase 960 begins by updating regression tests in a step 965. Updating the regression tests in the step 965 may, by way of example and not limitation, include receiving updated information regarding GPOS's and GPCD's (e.g., release of a new OS version or implementation of a new device or hardware version), updated verifiable and/or validatable and tested code, or other appropriate information. Updating may be performed, for example, automatically, manually, or some combination thereof. The updated regression tests are then run in a step 970. Running regression tests in the step 970 may, for example, be automatic, manual, or some combination thereof. The results are reviewed in a decision point 975 (e.g., automatically, manually, or some combination thereof). If the regression tests are not passed, the code returns to recoding phase 910 to be, for example, updated. If the regression tests are passed, the code is released in a step 980. The code may be released, for example, for use, for submission to a regulatory authority, or other appropriate release process.

Figure 10:
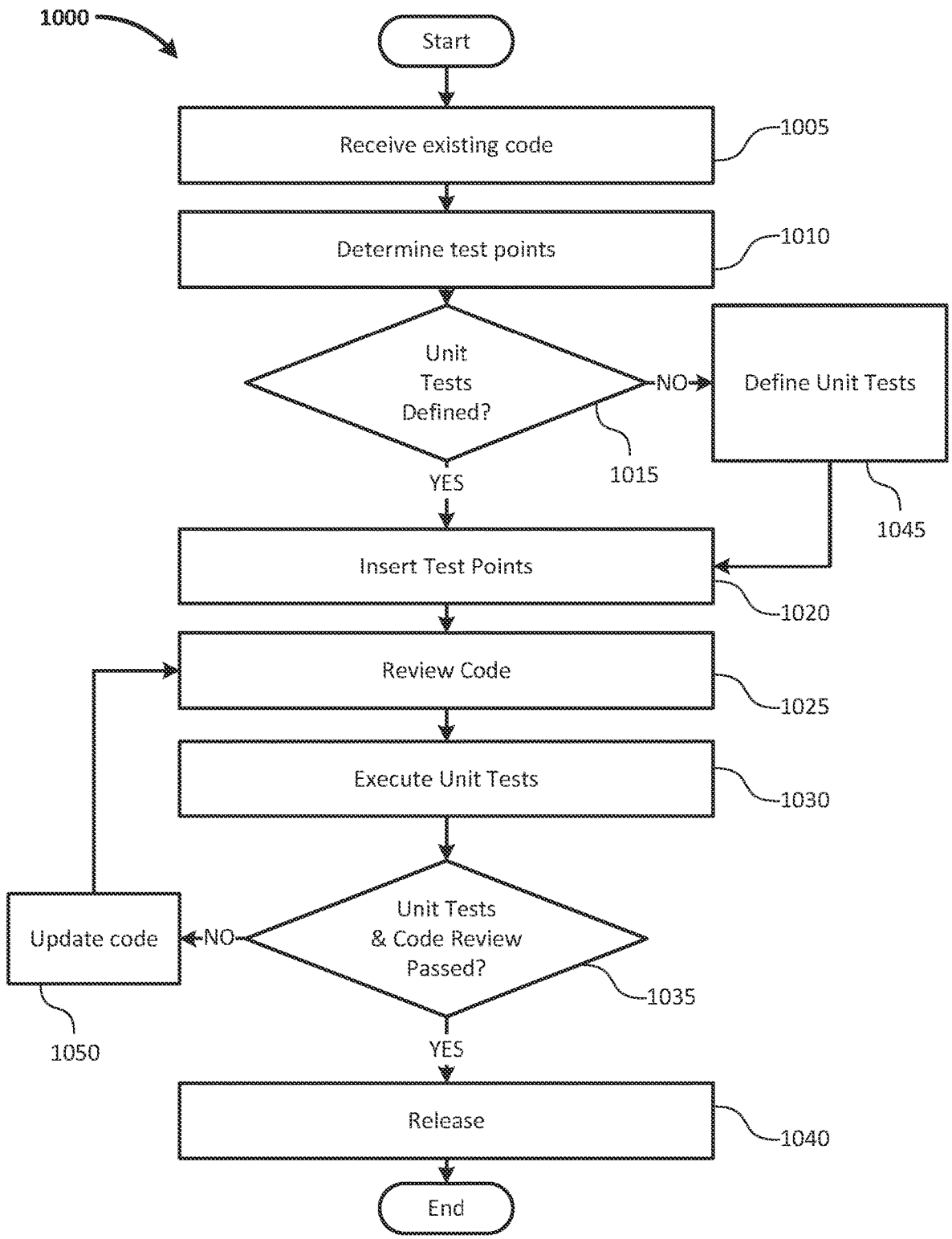
FIG. 10 depicts an exemplary method related to a middleware engine configured to introduce and execute test points for validation of code in a regulated environment.

FIG. 10 depicts an exemplary method related to a middleware engine configured to introduce and execute test points for validation of code in a regulated environment. In a method 1000, existing code is received in a step 1005. Test points are determined in a step 1010 such as, for example, by a test point insertion module (TPIM) of a middleware engine. For each test point, the software determines if at least one unit test is defined at a decision point 1015. If not, unit tests are defined in a step 1045, either manually or automatically. Once unit tests are defined, the test points are inserted in a step 1020.

The resulting verifiable and/or validatable code is reviewed. By way of example and not limitation, code review may be automatic (e.g., according to predetermined syntax rules, functional rules, and other predetermined rules), manual, or some combination thereof. The unit tests are executed in a step 1030, and the results reviewed at a decision point 1035. If the unit tests and code review are passed, the code may enter a release process in a step 1040, and the method subsequently complete. If unit tests or code review are not passed, the code is updated in a step 1050 as necessary, and subsequently reviewed in a step 1025. In various embodiments, the middleware engine may advantageously provide automatic transformation of conventional or otherwise existing code into verifiable and/or validatable, tested code for testing with one or more GPCDs, GPOSs, or some combination thereof.

Figure 11:
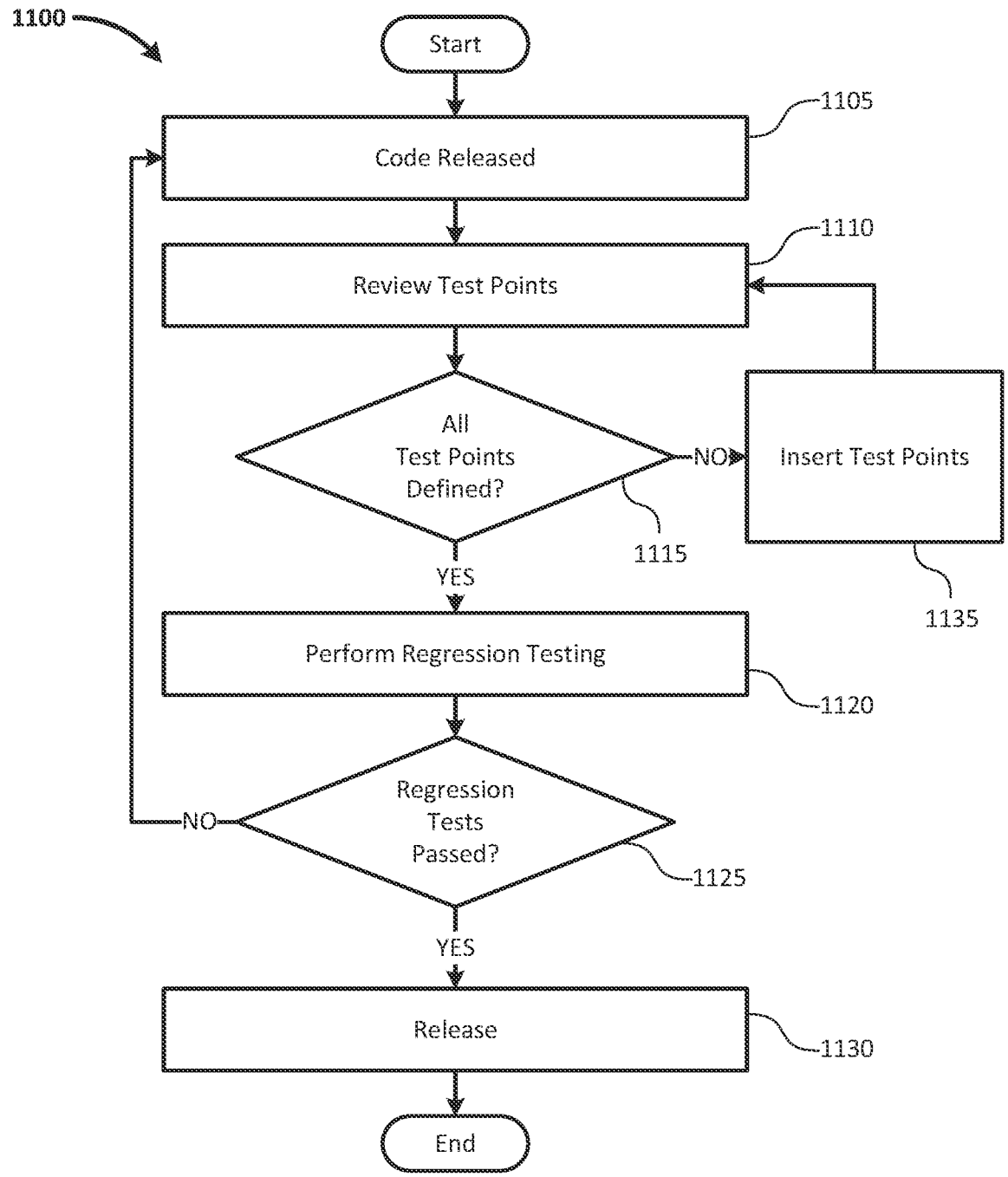
FIG. 11 depicts an exemplary method related to a middleware engine configured to perform regression testing for validation of updated code in a regulated environment.

FIG. 11 depicts an exemplary method related to a middleware engine configured to perform regression testing for validation of updated code in a regulated environment. A process 1100 begins with release of code in a step 1105. Release of code may, for example, include a version update, bug fixes, new software, additional features, other releases, or some combination thereof. The code may be received, for example, after being released from a method such as depicted and described in relation to FIG. 10. The code may be received, for example, by a middleware engine which may include, for example, a TPIM, RTM, or both.

Once code is released, the code is reviewed in a step 1110 to determine if tests points are existing and suitable (e.g., according to predetermined test point location and operation rules). If all required test points are not defined at a decision point 1115 (e.g., one or more test points are not suitable or not present in the code), test points are inserted in a step 1135 and the test points are subsequently reviewed in the step 1110. Test points may be inserted, for example, by a TPIM. Once all test points are defined, regression testing is performed in a step 1120. Regression testing may, for example, be performed by an RTM. The results are reviewed in a step 1125. If the regression tests are not passed, the code is returned to be updated and re-released in a step 1105. Once the regression tests are passed, the code enters a release process as verified and/or validated code in a step 1130. Once the verified and/or validated code is released, the method ends. The process may advantageously, by way of example and not limitation, perform regression testing required to verify and/or validate code for use in a regulated environment (e.g., in a medical environment or use case). The regression testing may, for example, occur when code is updated or newly released, other appropriate event, or some combination thereof.

Figure 12:
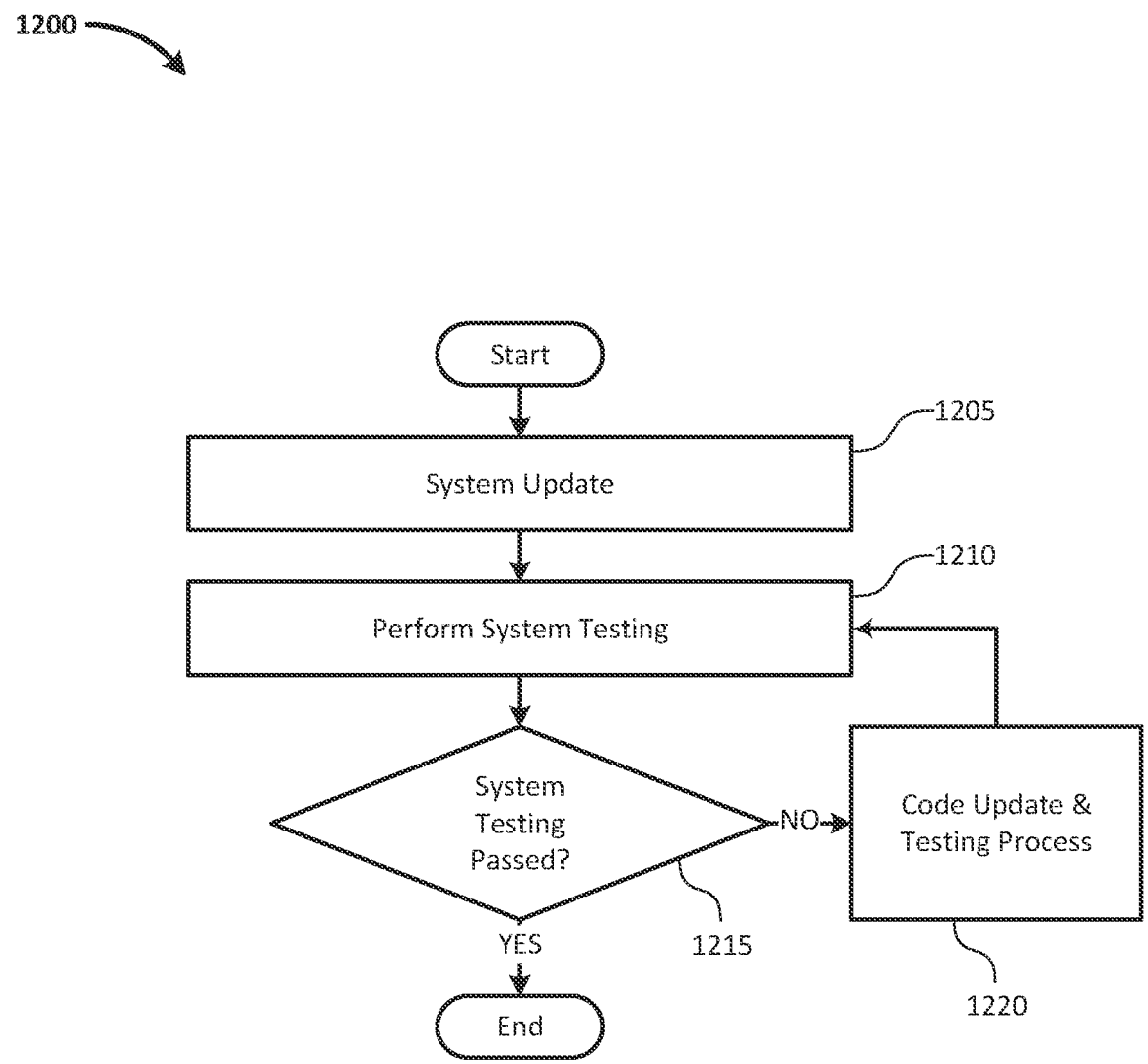
FIG. 12 depicts an exemplary method related to a middleware engine configured to perform regression testing when a general-purpose operating system is updated.

FIG. 12 depicts an exemplary method related to a middleware engine configured to perform regression testing when a general-purpose operating system is updated. A method 1200 begins when a system is updated in a step 1205. System update may occur, by way of example and not limitation, when a GPOS is updated or newly released or requested for use with verifiable and/or validatable code, when a GPCD hardware is changed or a new GPCD configuration is requested for use with verifiable and/or validatable code, other appropriate event, or some combination thereof. The system update in the step 1205 triggers system testing to be performed in a step 1210. System testing may be performed, for example, by an RTM of a middleware engine. System testing may, by way of example and not limitation, include regression testing by running pre-determined unit tests for one or more specific GPCD, GPOS, or combination thereof. The results of the system testing are reviewed in a step 1215. If system testing is not passed, the code is updated and tested in a step 1220. The update and testing process may, by way of example and not limitation, include methods such as are discussed and depicted in relation to FIGS. 10-11. Once all testing has been passed, the system may be verified and/or validated with the relevant code, and the process ends. The method may, for example, advantageously enable verified and/or validated code to be verified and/or validated in a specific system (e.g., with specific GPOS and GPCD combinations) to meet regulatory requirements (e.g., medical environments and use cases).

Figure 13:
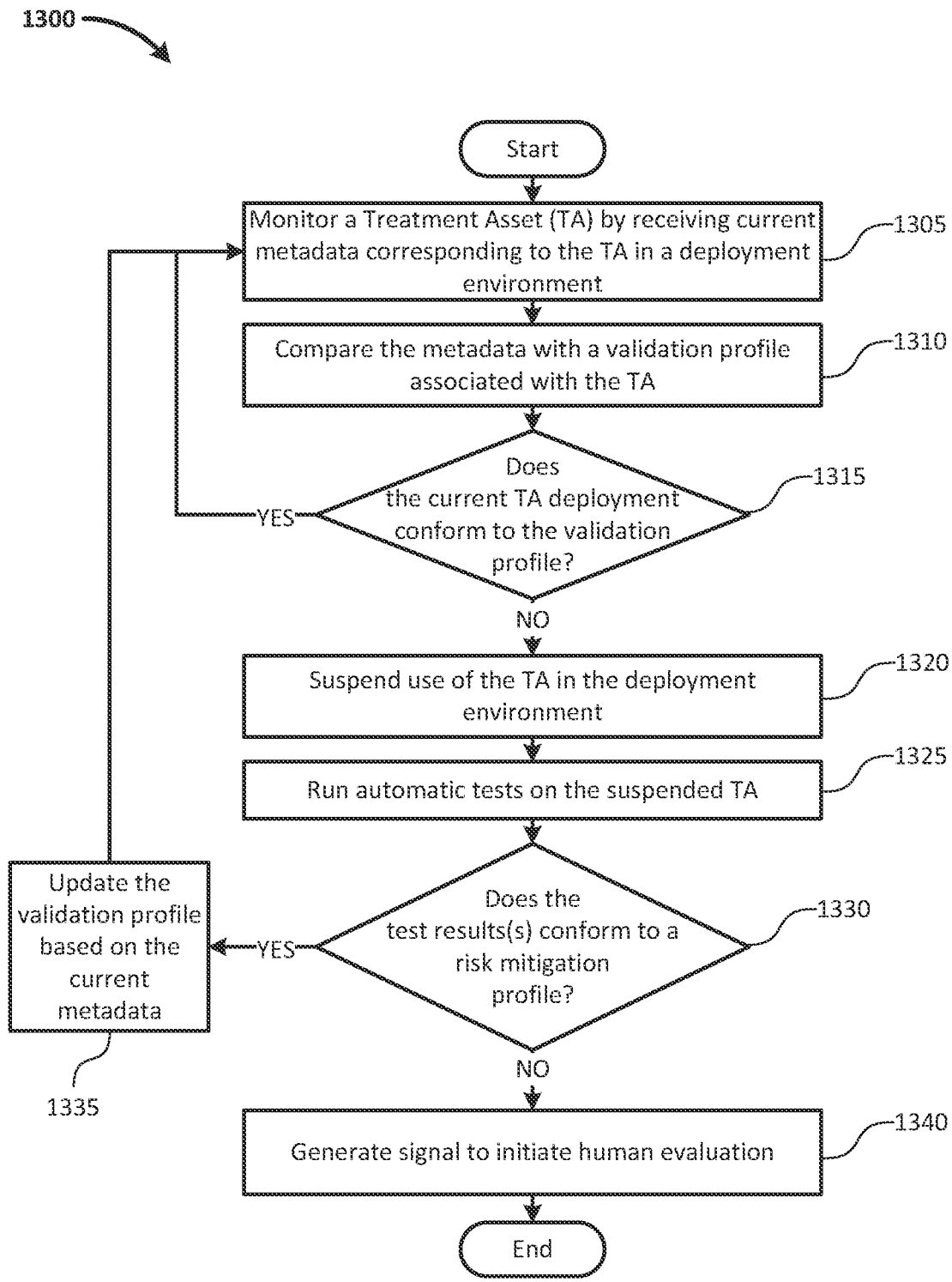
FIG. 13 depicts an exemplary method related to a risk management engine configured to monitor and test one or more treatment assets in a deployment environment.

FIG. 13 depicts an exemplary method related to a risk management engine configured to monitor and test one or more treatment assets in a deployment environment. For example, the risk management engine (RME) may be the RME 860 as described with reference to FIGS. 7-8. A method 1300 begins when the RME receives an instruction to start monitoring a treatment asset (TA) by receiving current metadata of the TA in a deployment environment in a step 1305. Next, the RME compares the metadata with one or more saved validation profiles (e.g., in a therapeutic profile) associated with the TA in a step 1310. For example, the RME may compare a timestamp of the last updated time of the TA in the deployment environment and the last verified and/or validated time stamp of the TA. The RME may, for example, compare a delivery environment version (e.g., game engine version, operating system version) to a profile including verified and/or validated environment versions in a metadata structure. The RME may, for example, compare deployment variables (e.g., user response parameters, environment variables) to verified and/or verified and/or validated deployment variables in a profile in a metadata structure.

After comparing the metadata and the risk profiles in the step 1310, the RME determines whether the TA conforms to the validation profile (e.g., according to at least one criterion defined in the validation profile) in a step 1315. If the TA is determined to be used in a verified and/or validated way according to the validation profile, then the RME continues to monitor the TA as described in the step 1305. If the RME determines that the TA is not used in a verified and/or validated way, then the RME suspends the use of the TA in the deployment environment and/or a development environment in a step 1320. In some implementations, the suspension of the TA may deactivate treatment mechanisms in the TA, but the use of the existing digital media may be allowed (e.g., user can continue to play the video game or listen to the song without therapeutic functions). In step 1325, the RME runs automatic tests on the suspended TA. For example, the tests may evaluate the risk of using the TA based on the current metadata. The tests may, for example, be determined based on a (predetermined) risk matrix, risks, and/or risk mitigations identified as associated with the TA.

Based on the test result from step 1325, the RME determines whether the test result(s) conform to a risk mitigation profile(s) in a step 1330. The risk mitigation profile(s) may, for example, be defined in a therapeutic profile and/or may be retrieved by a risk management engine. For example, the test result may show that the non-validation result determined in the step 1320 is due to an update in the operating system. The test results may further indicate that the change in the operating system does not affect the therapeutic mechanism in the TA (e.g., as defined in a risk mitigation profile and/or in a treatment mechanism associated with the TA) in which the update is verified. In this case, the RME may determine the risk is acceptable. In another example, the test result may show that the update on the operation system is not verified. For example, the operating system change may change an operation of a timing engine. The treatment mechanism associated with the TA may rely on the timing engine. The RME may determine that the risk is not acceptable.

In another example, the test result may show that the change is resulted from a change in the existing digital media asset. For example, there may be a change in a logo of in a video game in the opening credit. In this example, the RME may determine that the change is not affecting the therapeutic mechanism of the TA and the risk is acceptable.

In another example, the test result may show that the change in the game is affecting the therapeutic mechanism of the TA because of a hardware change. Then the RME may determine that the risk is not acceptable.

If the RME determines that the risk is acceptable (e.g., conforms to a risk mitigation profile) in step 1330, then the RME resumes usage of the TA in the deployment environment 1335. If the RME determines that the risk is not acceptable, then the RME generates a signal to initiate human intervention in a step 1340. For example, the human interventions may include human action in the development layer to update the monitored treatment module, re-integrate the digital asset and the treatment asset, change the parameters of the risk profiles, or some combination thereof.

In some embodiments the signal may initiate generation of one or more interfaces. The interfaces may, for example, display the change(s) detected in the step 1315. The interfaces may, for example, display one or more test results. The interfaces may, for example, display risk factors and/or risk mitigations corresponding with the treatment mechanism and/or the treatment asset. Accordingly, a human (e.g., developer, regulatory professional) may advantageously visualize the change, potential risks, and/or appropriate risk mitigations. The human may advantageously be able to quickly determine appropriate steps based on the specific information displayed in the interface(s).

In various embodiments, an immersive medicine platform may be used to deliver various digital content for medical treatment. For example, the immersive medicine platform may deliver digital content as medicinal media. The medicinal media may, for example, be selected and/or delivered according to predetermined therapeutic profiles. The predetermined therapeutic profiles may be (pre-)approved, such as by a regulatory body. The therapeutic profiles may, for example, be approved by the US Food and Drug Administration (FDA) and/or by another (medical) regulatory body. The therapeutic profiles may, for example, be validated and/or verified according to good practice (GxP) and/or good manufacturing practice (GMP).

In some embodiments the therapeutic profiles may, for example, include criteria corresponding to physiological response(s) associated with delivery of medicinal media. As an exemplary illustration, a therapeutic criterion may relate to stimulation of dopamine generation. In an exemplary illustration, a therapeutic criterion may relate to stimulation of serotonin generation. Various embodiments may, for example, be configured to induce one or more hormones. Various embodiments may, for example, be configured to induce generation of one or more neurotransmitters. Accordingly, in various embodiments media may be selected and/or generated according to an (expected) therapeutically related physiological response. For example, various embodiments may include media selection and/or generation and/or immersive therapy environment(s) as disclosed at least with reference to U.S. Application Ser. No. 63/202,881, titled "Immersive Digital Therapy," filed by Ryan J. Douglas on Jun. 28, 2021 and U.S. Application Ser. No. 63/203,058, titled "Management and Validation of Distributed Implementation of Treatment Modules," filed by Ryan J. Douglas, et al., on Jul. 6, 2021, the entire contents of which are incorporated herein by reference.

Figure 14:
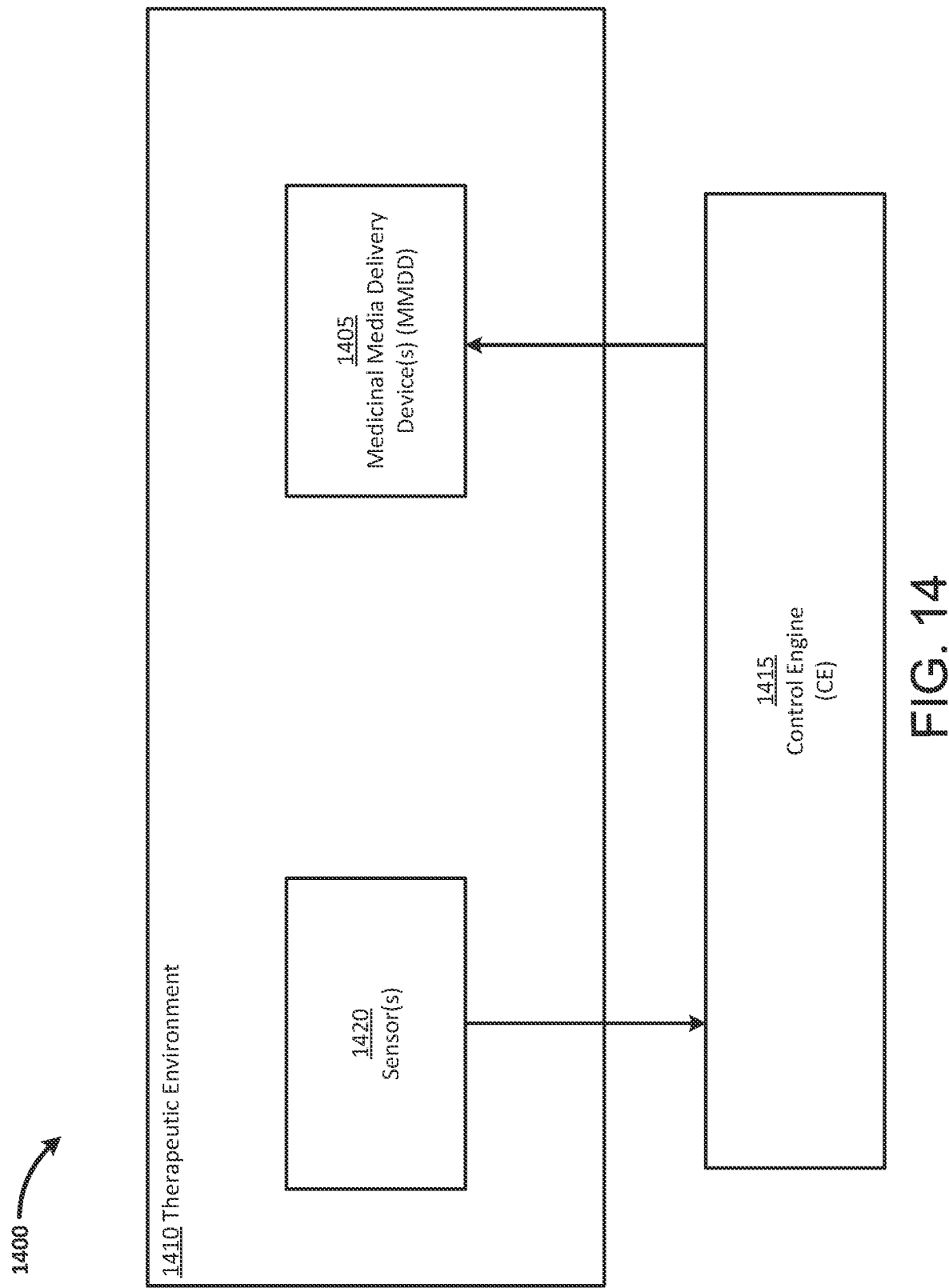
FIG. 14 depicts an exemplary system of an immersive medicine platform.

FIG. 14 depicts an exemplary system of an immersive medicine platform. An exemplary immersive medicine delivery system 1400 includes a medicinal media delivery device (MMDD 1405) deployed within a therapeutic environment 1410. In some implementations, various digital therapeutic content may be delivered via the MMDD 1405.

In one example, the MMDD 1405 may include a music streaming device that can deliver therapeutic music to treat anxiety. In another example, the MMDD 1405 may include an eBook reader that may deliver reading materials or books to, for example, treat speech therapy. In yet another example, the MMDD 1405 may include a video-game console that may deliver gaming content (e.g., a video game) to users in an immersive environment. In another example, the MMDD 1405 may include a general-purpose computing device (e.g., a person computer, a smartphone) that may deliver multiple types of digital medicinal media to the user.

In this exemplary system, the MMDD 1405 is connected to a control engine 1415. The control engine 1415 may be, by example without limitation, a software or an app that can determine a therapeutic content to be delivered to a specific user. In one implementation, the control engine 1415 may determine the therapeutic content based on a therapeutic profile. The therapeutic profile may include at least one criterion corresponding to therapeutic effect and/or delivery of potential medicinal media. In an exemplary implementation, a criterion may include a validation indicator. For example, the control engine 1415 may only select medicinal digital content with a positive validation indicator, meaning that the selected content is cleared for use. For example, in some embodiments a control engine may include and/or be connected to a risk management system such as disclosed at least with reference to U.S. application Ser. No. 16/423,981, titled "Quality Management Systems," filed by Ryan J. Douglas on May 28, 2019, the entire contents of which are incorporated herein by reference.

In some embodiments medicinal media may be pre-cleared for use. For example, the medicinal media may match predetermined safety criterion. The medicinal media may, for example, match predetermined therapeutic criterion (e.g., indication of dopamine, oxytocin, endorphins, and/or serotonin generation). In some embodiments the medicinal media may, for example, be pre-cleared based on historical responses during delivery (e.g., to the user and/or other users).

In some embodiments the medicinal media may be requested by a user and/or suggested based on historical user behavior (e.g., favorite user games, videos, books, songs). Medicinal media may, for example, be selected based on attributes identified in the medicinal media. The attributes may, for example, correspond to attributes in digital media which has historically generated a desired physiological response (e.g., responses associated with serotonin and/or dopamine generation, responses associated with one or more hormones, responses associated with one or more neurotransmitters) in the user. In some embodiments attributes may, for example, correspond a theme of the media. Attributes may correspond to media type. Attributes may correspond to social interaction associated with the media (e.g., a multi-player game). Attributes may correspond to a reward state (e.g., a reward the user historically responds positively to). Attributes may correspond to a challenge state (e.g., a challenge the user is capable of and/or desires to engage). Attributes may correspond to physical suitability (e.g., for the user's physical state, for physical attributes of the therapy).

In this example, the control engine 1415 receives input from one or more sensors 1420. The sensors 1420 may measure user activity before, during, and/or after the user received the content from the MMDD 1405. The sensors may, for example, include light sensors such as disclosed at least with reference to FIG. 15. In other examples, the sensors 1420 may include electrical sensors for measuring physiological responses, including heartrate, respiration pattern, sleep quality, brain activity, and/or other responses before, during, and/or after the user received the content. In other examples, the sensors 1420 may be implemented in a form of a survey to measure emotional responses from the users.

In some implementations, the control engine 1415 may evaluate the delivered therapeutic content based on input from the sensors and/or user activities. For example, the control engine 1415 may compare the sleeping qualities measured after delivering different music and may assign different gradings to the songs based on the measured sleeping qualities. In some implementations, the control engine 1415 may perform assessment of the user based on user responses. For example, the control engine 1415 may determine dopamine generation based on a user frequency for requesting a particular video game for playing. In another example, the control engine 1415 may determine serotonin generation based on a user's feedback (e.g., by requesting a star rating from the user) on their feeling after receiving a therapeutic content. In some embodiments, for example, the control engine 1415 may determine serotonin generation based on a user's social interaction (e.g., messages to other persons) regarding the therapeutic content.

Users of the therapeutic environment 1410 may, in some implementations, generate physiological responses that may, therefore, receive one or more therapeutic treatments. In some examples, the therapeutic environment 1410 may perform medicinal treatments by performing therapy directly. For example, the medical treatment may be light therapy for SAD patients. In another example, the medical treatment may deliver music as a part of music-thanatological treatment for terminally ill patients.

In some implementations, the therapeutic environment 1410 may perform medicinal treatments by training the users to perform certain tasks or to generate preferred physiological responses in response to certain stimuli. For example, the therapeutic environment 1410 may include an immersive environment, such as a virtual reality environment of a video game. For example, the video game may be a fishing game that trains a user with hypertension to breath in a preferred or predetermined pattern. For example, the user may be rewarded with more fishes to catch if the user breathes in a steady and slow manner. In some implementations, these physiological responses may be recorded by the control engine 1415. The control engine 1415 may, for example, then control the progress of the hypertension treatment based on the respiratory responses measured from the sensors in a series of the played games.

In various embodiments the control engine 1415 may, for example, be provided with one or more predetermined therapeutic control profiles (TCPs). A TCP may, for example, be pre-approved. The TCP may be selected from a library of pre-approved TCPs. A TCP may, by way of example and not limitation, define one or more criteria for selection and/or delivery of medicinal media. For example, in the fishing game illustration, the TCP may define acceptable parameters for breathing. The parameters may, for example, correspond to substantially universally safe respirations (e.g., respirations per minute). In some embodiments the parameters may, for example, define dynamic ranges based on a user's monitored physiological parameters (e.g., blood oxygen content, heart rate, brain patterns).

In some embodiments The TCP and/or the therapeutic environment 1410 may be periodically and/or continuously monitored by a remote verification and/or validation system. The remote system may determine whether the TCP is implemented according to approved parameters. For example, if the medicinal media is being delivered according to parameters that violate the approved TCP, the TCP may be disabled. The media may, for example, still be delivered (e.g., the user may still continue to play the fishing game), but the therapeutic components may be disabled (e.g., the breathing control may be disabled).

In some implementations, the therapeutic content may be approved by the medical health regulatory bodies and may be delivered via non-treatment platform. For example, the therapeutic content may be delivered via various online streaming platforms, by example without limitations, for music, video, and/or video games. In some embodiments, these platforms could be advantageously used without seeking approval from medical and health regulatory bodies, such as the US Food and Drug Administration, if the control engine 1415 and the therapeutic content are approved for use by the regulatory bodies.

Figure 15:
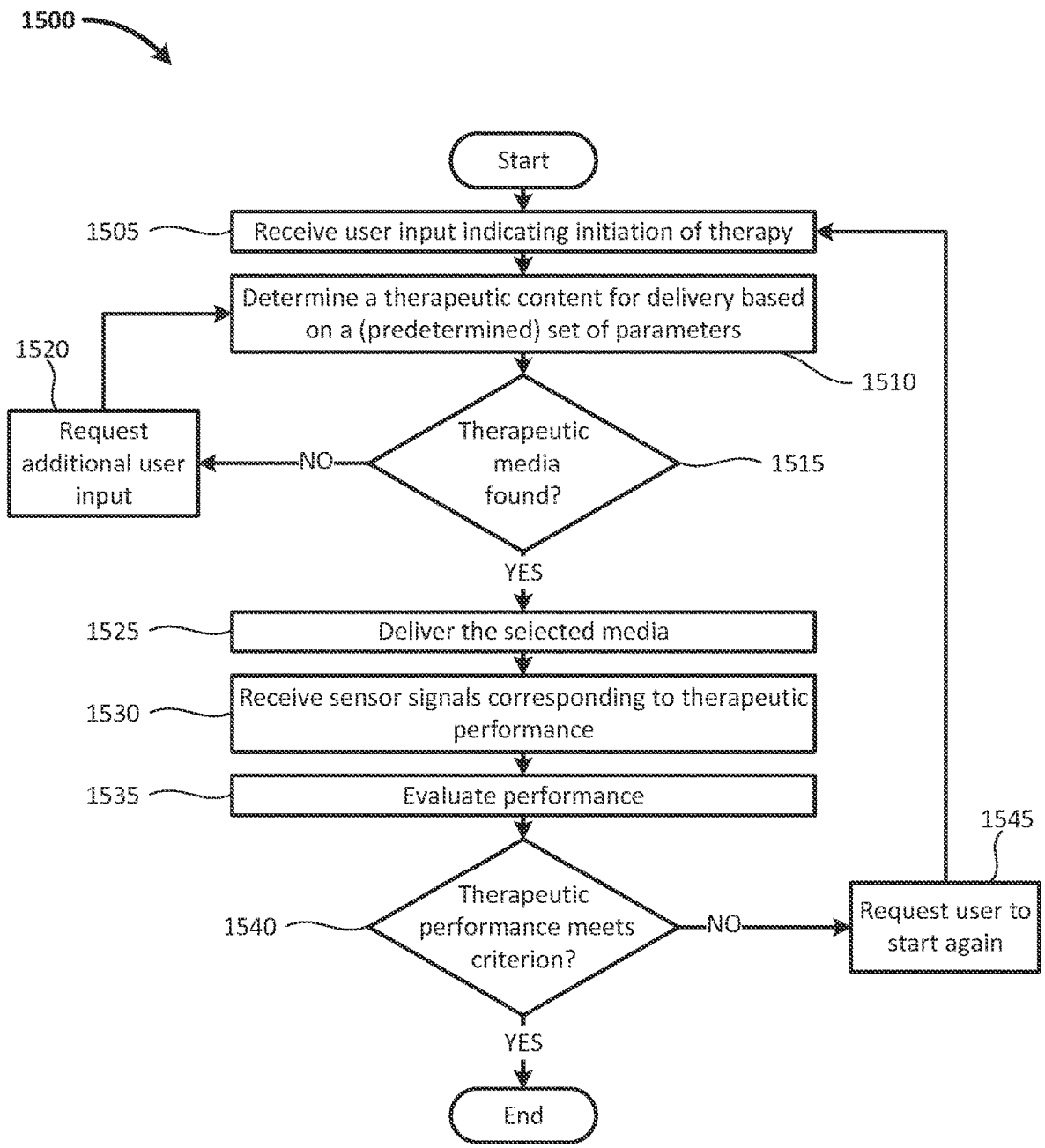
FIG. 15 depicts an exemplary method to deliver medicinal media.

FIG. 15 depicts an exemplary method to deliver medicinal media. For example, the control engine 1415 in FIG. 14 may at least partially implement the method 1500 to deliver medicinal content to a user. The method 1500 begins when the control engine receives a user input to start therapy at a step 1505. For example, a user may initiate a start therapy request by submitting a request via a play button on an app of a smart phone. In another example, medical personnel may submit the user input for a patient to initiate treatment for the patient. In some examples, the user input may include a profile of the user. In some examples, the user input may include a user preferred content type such as music category or game category.

After receiving the request, the control engine determines a therapeutic content for delivery based on a set of parameters. In some implementations, the set of parameters include profiles of user attributes, media attributes, and/or predetermined therapeutic attributes. For example, the user attributes may include the user's age, physiology, medical records, past records of therapy, reasons for therapy, or some combination thereof. The media attributes, for example, may include the type of the media and/or its characteristics. If the media is a video game, the media attributes may include, for example, the type of video game (e.g., first person shooting games, role-playing games), and/or therapeutic mechanism of the game (e.g., hypertension relieving, anxiety calming). In some examples, these therapeutic attributes of the media may be pre-approved by the government regulators.

In some embodiments a therapeutic profile may, for example, be selected from predetermined therapeutic profiles. In some embodiments a therapeutic profile may be provided (e.g., based on a doctor's prescription). Medicinal media may be selected based on the predetermined therapeutic profile.

In step 1515, the control engine determines whether a potential therapeutic media is found. If no media can be found, the control engine requests more input from the user 1520 and returns to the step 1510. For example, if the user requests an electronic dance music (EDM) for treating anxiety, the control engine may request the user to select another category of music because no media in the EDM category can be found to have calming effect.

If a potential therapeutic media is found, the control engine then delivers the selected media to the user 1525. For example, the media can be delivered via a non-medical treatment platform (e.g., MP3 player, smartphone, computer, stereo, gaming system, eBook reader). Next, the control engine receives sensor signals corresponding to therapeutic performance at a step 1530. For example, the control engine 1415 may receive signals indicating the heartbeat, breathing pattern, and/or electroencephalograph (EEG) signals of the user. In some embodiments the control engine 1415 may, for example, receive electronic signals corresponding to analyte concentrations (e.g., blood analysis of the user). In some embodiments the control engine 1415 may, for example, receive electronic signals corresponding to social interactions of the user during and/or after delivery of the media.

Next, the control engine evaluates therapeutic performance of the delivered media in a step 1535. For example, the control engine may evaluate the media based on signals received from the step 1530 and past records in the user's profile.

In step 1540, the control engine determines whether the therapeutic performance is satisfactory. For example, if it is a game for training a user to regulate the user's respiration pattern, a satisfactory result may be obtained when the user respiration pattern is 90% match with the desired pattern. If the therapeutic performance is satisfactory, the method ends. For example, the therapeutic performance may be determined to be satisfactory according to a TCP and/or other therapeutic profile. For example, a physician may prescribe certain therapeutic objectives (e.g., decreased breathing rate). A therapeutic profile may be generated according to the objectives. For example, a predetermined therapeutic profile may be selected and/or modified according to the objectives to generate a custom therapeutic profile. A performance of the therapy may be determined as function of the (custom) therapeutic profile.

If the performance is not satisfactory, the control engine generates a request (e.g., via an interface) to the user to start again in a step 1545 and returns to the step 1505. In some embodiments a profile (e.g., a metadata file structure) associated with the media and/or a profile (e.g., a metadata file structure) associated with the user may be updated according to the performance. Accordingly, various embodiments may advantageously customize medicinal media for the user. Various embodiments may, for example, advantageously determine some pre-existing media to be medicinal media for at least some users.

Figure 16:
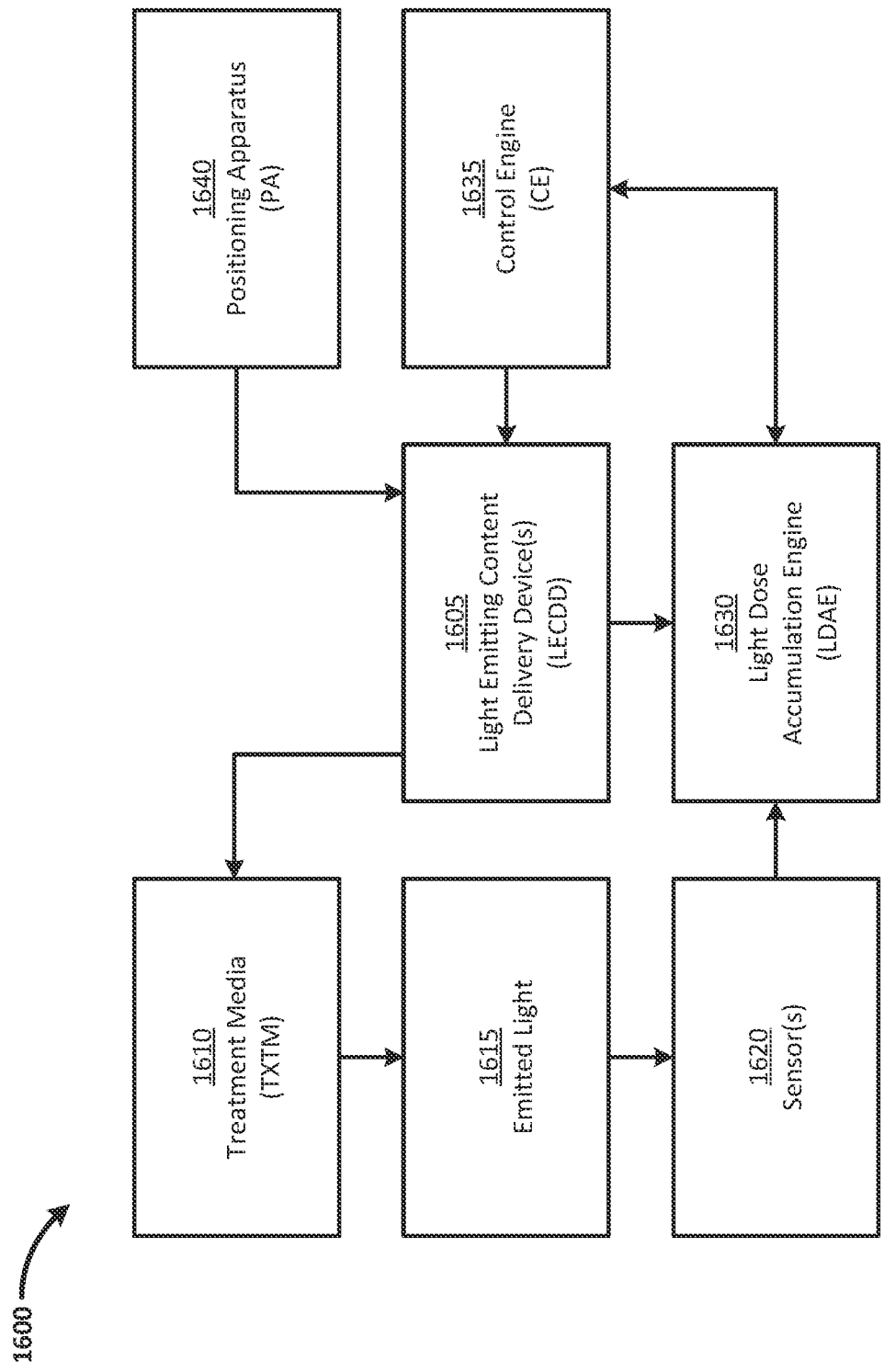
FIG. 16 depicts a block diagram of an exemplary immersive light emitting content delivery system.

FIG. 16 depicts a block diagram of an exemplary immersive light emitting content delivery system. A depicted immersive light emitting content delivery system 1600 includes a light emitting content delivery device (LECDD 1605). The LECDD delivers treatment media 1610 (TXTM) to a patient, thereby producing emitted light 1615. The emitted light 1615 is measured by one or more sensors 1620. The sensors 1620 provide feedback to a light dose accumulation engine (LDAE 1630). The LDAE 1630 provides feedback to a control engine (CE 1635), receives instruction from the CE 1635, and received feedback from the LECDD 1605. The CE 1635 provides commands to the LECDD 1605. The LECDD 1605 is positioned by a positioning apparatus (PA 1640).

In various embodiments, the LDAE 1630 may be provided with one or more sensors 1620 to measure light dosage. In some embodiments, the LDAE 1630 may be equipped to determine light dosage parameters, by way of example and not limitation, intensity, spectral content of the dosage (e.g., light temperature, wavelength ranges), other appropriate parameters, or some combination thereof. In some embodiments, sensors 1620 may be omitted. In some embodiments, the LDAE 1630 may digitally monitor display data to determine color and intensity of light to be sent to display for presentation to a user, before the light is emitted, such as directly from the LECDD 1605.

In various embodiments, the LDAE 1630 may mathematically integrate incremental or continuous dosages (including, for example, specific dosages for specific light properties of interest). The LDAE 1630 may, for example, determine and accumulate dosages over predetermined amounts of time (e.g., per hour, day, week, or other suitable time period). In some embodiments, the LDAE 1630 may, for example, accumulate dosages in predetermined wavelength bins. The accumulated levels in a predetermined time interval may be compared, for example, to a predetermined therapeutic dosage level. The predetermined therapeutic dosage level may be prescribed for the user, for example, by a physician or health care provider.

In various embodiments, a light therapy detector may be provided (e.g., sensors 1620). The light therapy detector may, for example, measure light emitted from a light-emitting device (e.g., the LECDD 1605 of FIG. 16). The light therapy detector apparatus may, for example, be connected to a computing device (e.g., the LDAE 1630 of FIG. 16) that calculates a total light dose the patient has received. In various embodiments, the light-emitting device may include, by way of example and not limitation, a smartphone, a tablet, a VR headset, a monitor, a television, or other suitable device. In various embodiments, the light therapy detector may include, by way of example and not limitation, an integrated light detector (e.g., an integrated camera in a smartphone), an external light detector, a mirror to reflect light to a light detector, or some combination thereof. In some embodiments, for example, a hardware apparatus (e.g., the PA 1640 of FIG. 16) may be provided with a light therapy detector and may be configured to receive, for example, a smartphone as a light-emitting device.

In various embodiments, a light therapy detector, a light emitting device, or both, may be connected to an app (e.g., the CE 1635 of FIG. 16). The app may, for example, be running on a smartphone which, for example, may also be the light emitting device, the light therapy detector, or both. The light emitting device may, for example, deliver a user's selected treatment media or light therapy. Treatment media may include, by way of example and not limitation, video, VR experience, reading materials, games, work documents and interfaces, light therapy (e.g., from an integrated flash emitter or other light output (e.g., infrared light, flashlight, or external light source), or some combination thereof. The light therapy detector may measure the light outputted by the light emitting device while delivering the selected content or light therapy.

Although various embodiments have been described with reference to the figures, other embodiments are possible. Although exemplary systems have been described, implementations may be deployed in educational, industrial, scientific, medical, commercial, and/or residential applications. Although examples of systems have been described with reference to the above figures, other implementations may be deployed in other processing applications, such as portable, desktop, and networked environments.

Exemplary Repurposing of Non-Therapeutic Digital Assets

Various embodiments may include repurposing video game code, digital assets, and/or multimedia for use in immersive medicine. Various embodiments may, for example, include development and/or repurposing of non-verified and verified and/or validated code, as described by ISO 62304, for use in medical devices and soft pharmaceuticals or similar such standards for the specific regulated industry.

Immersive medicine may, for example, bridge a gap between human gaming and medical devices and/or pharmaceuticals by creating a directly interactive and totally immersive diagnostic or treatment environment. This environment may, for example, be configured to stimulate the brain and body in a manner that induces and/or enhances diagnosis, treatment, and/or or rehabilitation of the individual. Various embodiments may, for example, include software tools to help people gather, communicate, and/or express emotional information. Such embodiments may, for example, enable improved management and/or understanding of the ways emotion impacts health, social interaction, learning, memory, and/or behavior of patients and/or providers in an immersive environment.

In some embodiments, middleware may be provided as a software tool to help develop or repurpose digital assets and code for clinical use. In various embodiments, test points may, for example, be introduced into preformulated code to allow current and/or future verification and validation of the code where development or delivery code environments are non-VV and/or are updated on a regular basis.

Interactive games, digital assets, and multimedia may be merged, in various embodiments, with medical applications to provide greater levels of engagement with diagnostic and treatment protocols. In some examples, the media itself may show medicinal properties and direct medical benefit.

Gaming engines have been created to speed the development of video games and multimedia. However, these gaming engines may produce code (e.g., software and digital assets) that lacks the testing and rigor required by medical regulators to test development and sustain release of the games for medical applications. Specifically, such gaming engines may lack adherence to ISO 62304, 14971 and 13485, and other US Food and Drug Administration (FDA) guidance and regulations, as well as similar medical device directives for the UK, EU, and other developed nations.

Once classified as a medical device by a regulatory body, gaming software, digital assets, or media may be required to conduct testing in both development and clinical environments, and to demonstrate consistent operation in a safe and effective manner. The game, digital asset, or media may, for example, be released on common (non-regulatory based) platforms such as, but not limited to, computers, game consoles and cellphones. With each update of the delivery platform (hardware or software), the code may be required to be re-testable in a time and cost-efficient manner to continue to show safety, effectiveness, and substantial equivalence to the cleared or approved device (code). Various embodiments may include a middle layer of software and digital assets, developed around common functional elements of at least one development and operating environment, capable of automating the addition of test points to allow the code to be verified and verified and/or validated to meet regulatory requirement of the FDA (or similar agency) for medical devices and/or pharmaceuticals.

For example, various embodiments may be implemented in a context of non-medical regulated industries. Such implementations may include, for example, software and software-dependent products and services in industries compelled to demonstrate and/or maintain development and/or test records for software they use and produce in making, delivering, or managing products and services. Example such industries may include, by way of example and not limitation, defense, aviation, communications, or some combination thereof. Exemplary products and services may include those that make or repurpose software code, digital assets, data, or some combination thereof. Such embodiments may, for example, include non-verified and verified and/or validated engines, systems, development environments, databases, data sets, or some combination thereof. Various embodiments may, for example, match standard game-related code with custom software, custom hardware devices, or some combination thereof.

In various embodiments, by way of example and not limitation, pre-existing code may be transformed into verifiable and/or validatable code. Verifiable and/or validatable code may be tested and verified and/or validated with one or more GPOS and/or GPCD. Various methods may include steps relating test point insertion, unit test creation and execution, regression testing, system testing, monitoring of changes to codes, devices, OSs, or some combination thereof. Test point insertion, code review, unit testing, regression testing, system testing, other appropriate steps, or some combination thereof, may be initiated, for example, manually and/or automatically. Automatic initiation may be triggered, by way of example and not limitation, by newly released code, updated code (e.g., updates to a GDE, SDE, or other code-related assets), newly added GPCD, GPCD hardware modifications, new GPOS, updated GPOS, other appropriate event, or some combination thereof.

In various embodiments, at least some validation steps and methods may be performed at least partially directly on a GPCD running a GPOS executing verifiable and/or validatable code. The code may, for example, include predetermined test points and unit tests. Unit tests may be triggered for at least some of the test points when, for example, a change is detected in the GPCD or GPOS, and/or other trigger event. Trigger events may include, by way of example and not limitation, a GPOS update, software installed or removed, peripheral device or other accessory connected or disconnected, a network change, other appropriate event, or some combination thereof. Some such embodiments may, for example, advantageously allow code to be reverified and/or validated dynamically, or 'on the fly,' as routine changes happen which may affect operation of the verified and/or validated code on the GPOS/GPCD.

In various embodiments, predetermined rules may be established, for example, associated with one or more test points, with one or more unit tests, associating one or more specific trigger events with one or more test points, or some combination thereof. For example, different groups of trigger events may be associated with specific groups of test points and associated unit tests. Trigger events and test points may be associated, for example, according to associated code portions which may be affected by a specific trigger event. Such embodiments may, for example, advantageously provide for efficient, dynamic regression testing (including system testing) without requiring all test points to be evaluated.

Various embodiments may implement at least one operational data store containing data gathered according to compliance standards. Various embodiments may, for example, implement at least one operational data store containing results of test operations. Various embodiments may, for example, implement one or more ongoing testing points and test operations with predetermined expected results. When changes occur (e.g., a new operating system version), predetermined test operations may be conducted at appropriate predetermined testing points. The results may be evaluated against the appropriate predetermined expected results. If the results match the predetermined results, a validation result may be provided. If the results do not match the predetermined results, appropriate personnel may be notified that further development may be required. Various implementations may advantageously provide for testing and validation such that dynamic platforms outside of developer control may be used in regulatory compliant medical products.

Immersive Therapy

Various embodiments may provide for (remote) management of immersive therapy. Immersive therapy may, for example, manage deliver a therapeutic modality via an interactive digital carrier. An interactive digital carrier may, for example, be at least some portion of digital media, digital assets, source code, video games, virtual reality, augmented reality, or some combination thereof. An interactive digital carrier may, for example, include a virtual environment, game theme, social interactions (e.g., in a virtual environment), (progressive and/or interactive) challenge state (e.g., in the virtual environment), or some combination thereof.

A therapeutic modality may, for example, include a therapeutic mechanic (e.g., motion, autonomic response, voluntary response, mentation). The therapeutic mechanic may, for example, be integrated into one or more interactive digital carriers (e.g., audio, video, video games, augmented reality, virtual reality) to deliver immersive therapy to a user (e.g., patient, athlete). The therapeutic mechanic may, for example, correspond to an interactive mechanic in the interactive digital carrier. For example, a breath-control therapeutic mechanic may correspond to breathing in a game environment. The game may, for example, alter in response to the user's engagement of the therapeutic mechanic (e.g., the player's character may respond, a challenge state may progress, rewards may be achieved, social interaction may be affected).

In various embodiments, a therapeutic mechanic may, for example, be defined by one or more therapeutic mechanic modules (TMMs). A TMM may, for example, include a therapeutic behavior profile, source code, digital media (e.g., audio, video, image, text), interaction sequence (e.g., interaction profile), or some combination thereof. Various embodiments may, for example, include a therapeutic modality, therapeutic mechanic, treatment mechanic, treatment modality, game mechanic, or some combination thereof, such as is described throughout U.S. Application Ser. No. 63/202,881, titled "Immersive Digital Therapy," filed by Ryan J. Douglas on Jun. 28, 2021, the entire contents of which are incorporated herein by reference. For example, at least paragraphs [0017-0026] and [0030-0063] discuss various implementations using therapeutic behavior profiles, game implementation profiles, game attribute profiles, therapeutic mechanics, therapeutic modalities, game mechanics, augmentation and/or adaptation management system, and combinations thereof.

Various embodiments may, for example, include a repository of validated TMMs. Each TMM may, for example, be subject to regulatory oversight such as by the U.S. Food & Drug Administration (FDA). A TMM may, for example, be validated according to (predetermined) current good manufacturing practices (cGMP) protocols. For example, a TMM may be validated using (predetermined) protocols such as, by way of example and not limitation, related to efficacy, risk management, or some combination thereof.

Validation Engine(s)

Various embodiments may, for example, be provided with a validation engine. A validation engine may coordinate and/or manage validation of a TMM. A validation engine may, for example, include association of the TMM with requirements, risks, mitigations, or some combination thereof. In various embodiments, a TMM may be implemented as (at least part of) a product object, such as is described in U.S. application Ser. No. 16/423,981, titled "Quality Management Systems," filed by Ryan J. Douglas on May 28, 2019, the entire contents of which are incorporated herein by reference. In various embodiments a validation engine may incorporate, be incorporated into, and/or communicate with at least one risk trace matrix engine and/or risk processor, such as is described at least with reference to FIGS. 1-4 of application Ser. No. 16/423,981.

Validated TMMs may, for example, be available for implementation in a non-regulated environment. For example, the repository of TMMs may be accessible for implementation in an interactive digital carrier. The interactive digital carrier may, for example, not be subject to (medical) regulatory oversight, and/or may include unregulated assets (e.g., source code, media). Each TMM may, for example, only be available for implementation in a non-regulated environment according to (predetermined) implementation parameters. The implementation parameters may, for example, be defined by one or more implementation profiles (e.g., a game implementation profile (GIP), examples of which are disclosed in U.S. Provisional Application No. 63/202,881).

In some embodiments, an interactive digital carrier may, for example, be a (video) game. The game may employ at least one game engine. The game engine may, for example, provide (unregulated) digital assets (e.g., digital media, source code) for use in the game. Digital assets may include, by way of example and not limitation, physics modules (e.g., light behavior, motion behavior), character modules, theme modules, environment modules, (social) interaction modules, or some combination thereof. The game may include various programs of instructions using the game engine to provide an interactive digital environment.

In some embodiments the game engine may be linked to one or more TMM repositories. For example, the game engine may be used to implement one or more validated TMMs in one or more interactive (video) games. Each TMM may be associated with one or more implementation profiles. Each implementation profile may include, by way of example and not limitation, implementation parameters, re-validation triggers, verification parameters, validation instructions, or some combination thereof. As an illustrative example provided by way of example and not limitation, a TMM may provide a therapeutic breathing mechanism. The TMM may define therapeutic breathing patterns, include breathing feedback, include breathing guidance (e.g., images, audio, text, video), or some combination thereof. The TMM may, for example, be implemented into an interactive digital carrier (e.g., game) in a virtual challenge environment. The game may, by way of example and not limitation, provide decreased visibility to adversaries in the virtual environment when (predetermined) breathing patterns are achieved (in reality) by a user. The validation engine may, for example, limit breathing parameters to predetermined (safe) ranges. For example, a calming and/or anxiety-reducing breathing pattern may be limited to 6-10 breaths per minutes. The predetermined ranges may, for example, be (pre-)validated. For example, the predetermined ranges may ensure that the TMM remains within a (predetermined) risk profile. Accordingly, various embodiments may, for example, advantageously preserve (predetermined) boundary conditions of a therapy corresponding to a TMM.

Verification Engine(s)

Various embodiments may, for example, include a verification engine. The verification engine may monitor implementation of one or more TMM's. The verification engine may, by way of example and not limitation, be operatively coupled to and/or in communication with a validation engine, a game engine, or some combination thereof. The verification engine may, by way of example and not limitation, monitor implementation details of the TMM in the interactive digital carrier; changes to the interactive digital carrier; parameters of the TMM before, during, and/or after delivery to a user (e.g., during run-time of a game program of instructions); or some combination thereof.

For example, a TMM may be provided with metadata defining validated implementation parameters, validated delivery parameters, or some combination thereof. The verification engine may receive, generate, and/or evaluate one or more carrier integration profiles (CIPs). A CIP may, by way of example and not limitation, include details of a validation status of a TMM implemented in an interactive digital carrier; a last validated date of a digital carrier augmented and/or adapted by a TMM; an identifier (e.g., version number, hash code) corresponding to validated versions of the interactive digital carrier, modules, and/or digital assets thereof; or some combination thereof.

For example, a TMM, a digital carrier in which the TMM is implemented, and/or a verification engine may be configured to initiate communication between the digital carrier, the TMM, and/or the verification engine. The verification engine may, for example, evaluate one or more CIP associated with the TMM and/or the carrier. The verification engine may compare the CIP(s) with one or more current metadata parameters of the TMM and/or carrier. Current metadata parameters may, by way of example and not limitation, include current carrier, module, and/or asset identifiers (e.g., version code, hash code); runtime reports from the TMM (e.g., documenting actual use of the TMM), or some combination thereof. The verification engine may compare the received metadata to one or more (previous) CIP(s) (e.g., previously validated by the validation engine).

The verification engine may update the CIP(s), such as with a last verified date. In response to determining the current metadata does not match a validated CIP, the verification engine may determine that the implementation of the TMM into the carrier is non-validated. In various embodiments the verification engine may, for example, submit the current metadata to the validation engine, generate one or more notifications, disable the TMM in the carrier, or some combination thereof. Accordingly, the TMM may advantageously be monitored for compliance with validation requirements. Some embodiments may, for example, advantageously deactivate a regulated TMM in response to a non-validated change in an unregulated digital carrier.

In response to a change in a digital carrier may, the verification engine may submit the current metadata to the validation engine. The validation engine may, for example, evaluate a risk profile of the changes. For example, for the illustrative breathing mechanic, if a non-validated change altered digital media used as a launch screen of the digital carrier, or changed source code related to a chat box, the validation engine may determine that the risk profile relative to the TMM has not changed. For example, the validation engine may compare the changes (e.g., as determined from the received metadata) to (predetermined) requirements, risks, and/or risk mitigations. The validation engine may, by way of example and not limitation, employ a risk trace matrix engine to evaluate the changes. In some embodiments, such evaluation may, for example, be done manually. For example, a reviewer may be prompted to assess risk of a change. The risk may (e.g., manually, automatically) be determined, by way of example and not limitation, to impact or not impact the TMM. The impact status may, for example, be associated with the TMM and/or digital carrier (e.g., saved in metadata, stored in a CIP). If the TMM is determined to be impacted by the change, the TMM may, for example, be updated (e.g., manually, automatically), re-verified and re-validated and made available with updated parameters (e.g., updated digital carrier identification, modified implementation parameters) for ongoing use in the media environment. During update the TMM may, for example, be set to be temporarily unavailable pending review and reverification and revalidation and/or may be updated to shift to non-therapeutic play (e.g., disable therapeutic claims) during this time. Accordingly, during this period of time the media may not be available for use or available without access to the TMM. Various embodiments may, for example, advantageously prevent unverified and/or unvalidated use of the TMM.

On the other hand, if a non-validated change altered an in-game response to breathing, such as a speed in the game environment related to breathing of the player, the validation engine may determine that the risk profile may be affected. In response to determining that the risk profile may be affected, the validation engine may, by way of example and not limitation, generate a notification, prompt a user (e.g., authorized validation reviewer) to review the change and determine a new risk level and/or appropriate mitigation, (automatically) determine a new risk level and/or select an appropriate (predetermined) risk mitigation, or some combination thereof. Accordingly, such embodiments may advantageously permit rapid changes to non-regulated components of an interactive digital carrier not affecting the risk profile of the TMM, while ensuring that the TMM is implemented and/or deployed in the carrier in a validated manner (e.g., maintaining a validated risk profile). Various embodiments may, for example, advantageously maintain perpetual validation of an interactive digital carrier augmented and/or adapted by one or more TMMs, even when the carrier itself is (rapidly) updated.

Integrity Management Module(s)

In various embodiments a TMM may be provided with at least one integrity management (IM) module. An IM module may, by way of example and not limitation, include signals and/or codes configured to ensure the integrity of the TMM is not compromised. The IM module of the TMM may, for example, be configured to ensure that treatment parameters of the TMM are not hacked or otherwise modified in a way that may put the treatment in jeopardy and/or allow it to be used outside of verified and validated parameters. For example, the IM module may include parameters and/or a program(s) of instructions configured to be executed by a processor. In various embodiments the IM module(s) may be configured to be executed independently and/or in cooperation with another engine and/or module such as, by way of example and not limitation, a verification engine, a validation engine, or some combination thereof.

Non-Treatment Based Modification of TMM(s)

In various embodiments a TMM may be provided, for example, with controllable parameters. A controllable parameter may, for example, define one or more portions of a TMM that are permissible to be changed to (better) fit parameters of an interactive digital carrier (e.g., game) without impacting the validated treatment effect. As an illustrative example, if it is determined the color display of a breathing mechanism prompt did not impact the viability and, therefore, the verified and validated portions of the treatment mechanism, those parameters may be allowed to be changed to better suit the game environment. Accordingly, in this illustrative example, an associated TMM may be provided with a controllable parameter of color of a display of a breathing mechanism prompt. In various embodiments, a TMM may, by way of example and not limitation, be associated with a controllable parameter in a file defining a TMM, a TBP, a GIP, a CIP, or some combination thereof.

Interconnectivity of TMM(s)

In various embodiments a TMM may be configured to respond in context of modules (e.g., TMMs) with which it is permitted (e.g., validated, verified) to interact with and/or be implemented together with. For example, a TMM may be provided with parameters (e.g., internal, reference to permission matrix(es)) which define permitted and/or non-permitted modules for association with the TMM. The parameters may, by way of example and not limitation, define modules directly and/or define modules as a function of parameters by which modules which are not explicitly named may be identified as permitted or non-permitted. In some embodiments the TMM may be provided with parameters which identify modules which are permitted under certain parameters (e.g., thresholds, environments, applications). Accordingly, multiple TMA/Is may, for example, advantageously be deployed in a single media carrier to allow for one or more treatment modalities within the single media. Such modular modules may, for example, identify the other TMMs (e.g., suggested, proposed, potential, implemented) they are compatible with, without impeding the validity of an individual TMM's verified and validated treatments.

Counter-Indication Engine(s)

In various embodiments a TMM(s), an implementation environment (e.g., as disclosed at least with reference to an implementation agent, hereafter) in conjunction with one or more TMMs, or some combination thereof may, for example, include an indication for use, a counter indication, or some combination thereof. An indication may, for example, include information for a carrier developer(s) (e.g., game, media), information for end users (e.g., patients), or some combination thereof. An indication (e.g., for use, counter indication) may be provided, by way of example and not limitation, via a file, parameters such as metadata in an existing file, a program of instructions generating a notification, or some combination thereof. A counter indication may, for example, define one or more TMMs which should not be implemented together (e.g., in the same digital carrier, in the same environment of a digital carrier, in the same time space of a digital carrier), define individuals with certain underlying conditions or traits that should not engage with the TMM(s), or some combination thereof. The counter indication may include, for example, a direct definition and/or at least one function by which a counter indication may be determined (e.g., manually, automatically).

Implementation Engine(s)

In some embodiments an implementation engine may, for example, be provided. The implementation engine may interact with the validation engine, the game engine, or some combination thereof. The implementation module may, for example, be operably coupled to one or more game engines. The implementation engine may, for example, include a game engine. The implementation engine may, for example, be implemented as at least one module in a game engine.

In an illustrative example, an implementation engine may be operably coupled to at least one repository of (validated) TMMs. The implementation engine may, for example, be operably coupled (e.g., including, integrated with, communicating with such as through an API) at least one development environment (e.g., a game development environment, integrated development environment). A carrier developer (e.g., game developer) may select TMMs directly from the repository in the development environment. Some embodiments may, for example, include a "drag-and-drop" interface. Some embodiments may include a discovery engine. For example, a discovery engine may determine a suggested TMM(s) for a carrier (e.g., a game) based on attributes of the carrier (e.g., using a GAP). The discovery engine may, for example, generate an interface having a selection of suggested TMM(s). The interface may, for example, include suggested implementation parameters.

In various embodiments the implementation engine may be 'aware' of parameters of the interactive digital carrier's environment (e.g., during design time and/or run time). For example, the implementation engine may be provided with game parameters associated with delivery of the TMM to a user (e.g., player). The carrier parameters may, for example, be dynamic contextual validation parameters (DCVPs). A DCVP may, for example, be a In another breathing mechanic illustration, the corresponding TMM may, for example, be implemented in a game on rails. A game on rails may, for example, (interactively) conduct a player through a progressive virtual reality (e.g., 4-dimensional: space and time). The breathing mechanic may, for example, be implemented in the game environment corresponding to travel through a virtual three-dimensional reality. A player's (monitored) breathing parameters (e.g., depth, duration, frequency, inhale profile, exhale profile) may, for example, be correlated to a speed of travel of the player's character in the virtual environment. The TMM may, for example, have an absolute validated frequency parameter range of 6-10 breaths per minutes (e.g., considered safe in all conditions). The TMM may, for example, have an extended relative validated frequency parameter range when parameters in the context of the carrier environment are within a predetermined range (e.g., DCVPs). As an illustration, the TMM may have an extended validated range as low as 4 breaths per minute. However, the extended validated range may correspond to DCVPs, such as the player's physical speed and/or virtual speed, being below a predetermined speed threshold.

The implementation engine may, for example, monitor (e.g., in run-time) DCVPs beyond the TMM itself. For example, in the illustrative breathing mechanic/speed example, the implementation engine may monitor the real and/or virtual speed of the user (e.g., during game play). The implementation engine may adjust the validated TMM parameter(s) based on the DCVPs, based on predetermined DCVP profiles (e.g., approved correlations of TMM parameter ranges to DVCP ranges). Accordingly, the implementation engine may advantageously enable more dynamic interaction and/or greater parameter ranges while ensuring a safe and/or validated TMM in an environment.

Therapeutic Augmentation

In various embodiments, an existing and/or new game may be enriched with at least one therapeutic behavior defined by at least one therapeutic behavior profile (TBP). A TBP may, by way of example and not limitation, define a desired behavior (e.g., rhythmic breathing, secretion of an enzyme, shift in a thought pattern, triggering of an autonomic function). The TBP may, for example, further define a series and/or continuum of goals, metrics to characterize the user's level of performing the behavior, metrics for determining acquisition of the behavior by the user, thresholds (e.g., minimum, maximum, and/or targeted of various metrics including, for example, frequency, magnitude), or some combination thereof. The TBP may further be provided with and/or accompanied by at least one game integration profile (GIP). The GIP may, for example, define integration of the therapeutic behavior with the game environment. In various embodiments the GIP may, by way of example and not limitation, define game environments, rewards, scenes, music, motions, pre behavior actions, post-behavior actions, pre-behavior thoughts, post-behavior thoughts, or some combination thereof. In various embodiments a single TBP may be applied to multiple games such as, for example, by using at least one GIP specific to each game.

In various embodiments a game may have at least one game attributes profile (GAP). The GAP may, by way of example and not limitation, define types of behaviors natively embedded in the game, types of behaviors able to be embedded in the game, game environment (e.g., aerial, ground-based, role-playing, individual, massively multiplayer), theme (e.g., challenge-based, shooter-style), or some combination thereof. In various embodiments one or more TBPs may further be associated with specific game characteristics. In various embodiments a TBP may, by way of example and not limitation, be associated (e.g., suitable for, contraindicated for) specific game attributes. Accordingly, in various embodiments a game may be selected according to matches between a TBP and GAP. In various embodiments a game may be developed to have a specific GAP.

In various embodiments a GAP and/or TBP may be used to select a game for use for prescription and/or recommendation for a specific user, disorder/malady, or some combination thereof. For example, a user seeking a specific TBP who (also) has hypertension may be recommended games having GAPs excluding aggressive and/or shooter-style games, while recommendations for a user without hypertension may include GAPs inclusive of those attributes. The games may, for example, be associated with the same TBPs. In various embodiments games may be recommended by trained personnel (e.g., medical consultants), automatically (e.g., according to a survey-based input by users), self-recommended by a user, or some combination thereof.

Various embodiments of the system may be applied to a wide variety of treatment modalities. Treatment modalities for therapeutic augmentation may, for example, be selected based on a high correlation (e.g., predicted, experimental) with engaging game mechanics. An example below, based on hypertension, is used to demonstrate the concept.

By combining habit forming gaming mechanics and proven treatment mechanisms, some embodiments of a software as a medical device (SaMD) approach may significantly improve patient compliance. In addition, the "game" mechanics may be tested to be accessed via a cell phone (e.g., via a (regulatorily approved) companion app) and thus available to patients throughout the day when stressful situations occur, leading to greater, cost effective reach to underserved populations and further flexibility of treatment for hypertension.

Various examples of game design and mechanics for biofeedback training for treatment and use of companion treatment application including by way of example and not limitation, a gamified version of the concept may use game action to induce mild anxiety and/or increased physical exertion moments and/or periods while tracking and/or sensing breathing patterns, motion patterns and potentially other biological indicators (such as but not limited to heart rate and blood pressure) of physical and/or emotional stress, distress, (moments of) pleasure, bliss, and/or self-reflection.

In some implementations a biofeedback mechanism may display patient breathing and other biological indicators patterns, for example light, sound, haptics, spatial orientation, animation, movements, or other visual/auditory clues or displays.

Various implementation may use (additional) feedback mechanisms to instruct the player/patient on how to breathe and/or move to reduce the anxiety/stresses and other such physical body reactions to emotional distress (calming mechanisms). For example, various embodiments may overlay lights, new sounds and/or changing tones, additional animations or other visual/auditory guidance showing the patient how to change movements, sounds, thinking or breathing to achieve a desired (e.g., calm) state.

Various embodiments may preserve the play action and therefore the patient compliance aspects of the game (the game's inherent gripping, immersive, characteristics and/or attractiveness being key to the patient to continuing to use the device with much greater frequency than is normally experienced with patient driven therapeutics). The cycle of play may, for example, incorporate the calming mechanisms (e.g., defined by an associated TBP) as a time limited portion of the game that may provide the player with special abilities to excel in the game (like a bonus action or state with improved ability to score and achieve mastery in the game) (e.g., defined by at least one GIP).

By way of example and not limitation, in an embodiment implemented in a shooter style game (e.g., characterized by a GAP), a player/patient may be guided to and monitored through biofeedback to breathe and/or move and/or create sounds and or think/process in a way that may induce stress relief and calming. The more successful the player/patient is at achieving and maintaining the state (e.g., as defined by a TBP) the more game benefit they may receive (e.g., as defined by a GIP).

Post-Immersion Therapy

In various embodiments a companion treatment app or device may deploy (substantially) equivalent and/or identical mechanisms of action (e.g., treatment modalities) outside of a gaming environment. For example, the companion app may be used during actual treatment, rather than in mechanism delivery/training/immersion (e.g., performed in a non-medical game environment). The companion treatment app may, for example, (subconsciously) trigger the brain of the user to access the learned behavior and effortlessly complete a learned behavior (e.g., cognitive, motor, and/or autonomic function) to effectively treat an underlying condition. In various embodiments the companion app may, for example, be loaded with at least some aspects of the TBP(s) recommended for the user. The companion app may, for example, be loaded with at least some aspects of a GAP of the game the user has been using to learn the therapeutic behavior defined by the TPB.

In some implementations, when the patient is seeking treatment for an acute condition but is not going to play the game (e.g., due to time constraints, due to environmental constraints such as work/school, due to emotional behavioral constraints such as unwilling and/or unable to play in a current mental/physical state), they may enter a treatment (e.g., companion) app. The same breath measurement and biofeedback mechanisms as used in the game may be present. Various embodiments may include no game play, having only guided steps to treatment to address the episode. The familiar interface may allow immediate access to the subconsciously trained mind, allowing the patient to access the well-practiced mechanic. Accordingly, the treatment effect may be (greatly) enhanced relative to conscious delivery of treatment and/or training.

In some implementations, the companion treatment app or device may advantageously distinguish a treatment training mechanism in the gaming environment, as a "non-medical device" allowing relaxed regulatory oversite that otherwise may place demands on the game that may reduce its ability to be compelling and immersive. For example, a TBP may simply define physiological behaviors suitable for use in a game that may not be subject to regulatory oversight. The TBP may, for example, be associated with medical therapy which may be formally monitored and/or trained using approved methods (e.g., by an approved companion app/device, in a medical facility, and/or by licensed medical personnel). The user may then select a game having a matching TBP to self-learn the game in a non-medical environment. For example, the game may not formally monitor and/or train the patient, as the purpose of the game, so far as the user is concerned, is to play. Accordingly, the user may learn useful (therapeutic) behaviors using a game (e.g., available at a lower cost due to no or reduced medical regulatory burden), and then implement and/or monitor those behaviors medically using an approved device and/or environment.

Augmentation and/or Adaptation Implementation

Various embodiments may, by way of example and not limitation, be provided with a matrix which defines a confluence point between game theme/story and biologically beneficial game mechanics and treatment regimes. Such embodiments may, for example, create and/or maintain a flow-state, such as, for example, through stimulus of one or more pleasure centers of the brain and/or body, where subconscious entrainment drives neural plasticity to arrive at a fundamental physiological autonomic change in the body the positively impacts function and is broadly applied beyond the base level training mechanism (game).

Various embodiments may implement a confluence of strong storytelling with integrated game mechanics and treatment mechanisms that may, for example, maintain (neural) chemical production (e.g., dopamine oxytocin, endorphins, serotonin) while allowing unconscious learning and ultimately change behavior and/or physiology through neurologic plasticity arriving at entrainment. For example, some implementations may induce subconscious neurological entrainment with a wildly effective positive reinforcement feedback loop. In various embodiments, neurological entrainment may be at least partially achieved using a combination of social and/or intrinsic motivators.

Predetermined augmentation and/or adaptation rules may, for example, be provided. The predetermined augmentation and/or adaptation rules may, by way of example and not limitation, be applied to proposed treatment modalities, proposed interactive digital carriers (e.g., games and/or game modules, movies (including, for example, feature films), songs and other forms of media), or some combination thereof. In various embodiments predetermined augmentation and/or adaptation rules may be applied to augmentation of a specific interactive digital carrier(s) with a specific treatment modality(ies). In some embodiments, the rules may, for example, be applied dynamically (e.g., during augmentation), post facto (e.g., after submission of a proposed augmentation), pre-augmentation (e.g., pre-evaluation before augmentation is begun) or some combination thereof. Various embodiments may, for example, implement rules in one or more GIP, TBP, and/or GAP.

In various embodiments, at least one predetermined rule may be applied to determine if an augmentation/adaptation is plausible. Some embodiments may, by way of example and not limitation, apply a high(est) level of weighting to at least one such rule. For example, a treatment mechanism may be required to have positive correlation with an attractive game mechanic. The positive correlation may, for example, be determined by clinical trials. In some embodiments, for example, a predetermined therapy module may be provided. The therapy module may, for example, include at least one digital asset (e.g., source code; digital media such as image files, audio files, parameter value files, video files; TBP file). In some embodiments the therapy module may be pre-loaded into a library of available therapies. At least one therapy module may be selected (e.g., by a therapy professional, game designer, game augmenter/adapter) as a function of predetermined attributes (e.g., defined by a TBP) of the therapy module which may have a positive correlation with attributes of a game (e.g., as defined by a GAP).

Positive correlation rule(s) may, for example, define appropriate game mechanic(s) for a specific therapeutic modality. For example, a game mechanic requiring high activity (e.g., jumping, running, cardio-type activity) may have a negative correlation with a therapeutic modality of slow, deep breathing. Implementation of slow, deep breathing in such a game mechanic may induce a player to practice slow, deep breathing during increased exertion. Accordingly, a game user may experience negative physiological effects (e.g., hypoxia) and/or frustration (unable to maintain the slow, deep breathing during increased exertion).

Various embodiments may, for example, automatically suggest appropriate therapeutic modalities. For example, in the previous example, an augmentation engine (which may, for example, be configured in various embodiments for augmentation and/or adaptation of a digital carrier) may determine that the selected therapeutic modality (slow, deep breathing) is inappropriate (e.g., has a negative correlation with the game mechanic). The augmentation engine may, for example, suggest a (related) therapeutic modality having a positive correlation with the game mechanic. For example, the augmentation engine may suggest a therapeutic modality including a breathing technique (e.g., a related therapy focused on a physiological system(s)) suitable for increased exertion (positive correlation with game mechanic). Various embodiments may, by way of example and not limitation, select therapeutic modalities based on the game mechanic, suggest game mechanics based on a therapeutic modality, or some combination thereof. Some embodiments may, by way of example and not limitation, suggest a game mechanic and/or therapeutic modality based on a physiological system (e.g., respiratory, cardiac), physiological result (e.g., dopamine, oxytocin, endorphins, serotonin generation, adrenaline generation, decreased heart rate, decreased blood pressure, increased sympathetic muscle stimulation), mechanics (e.g., jumping, running, bending, sitting, eye motion), or some combination thereof.

In various embodiments at least one predetermined rule may be applied to determine if a level (e.g., quantity, intensity) of a target mechanic is suitable for therapy and/or an interactive digital carrier. Some embodiments may, by way of example and not limitation, apply a second level of weighting to at least one such rule. For example, a particular mechanic (e.g., breathing, motion, mental concentration) used in a game may be required to be capable of reaching a minimum quantity and/or intensity in order to be suitable for therapy. An eye motion mechanic which only occurs once in a game may, for example, not be therapeutic. For example, even though the game mechanic (a specific eye motion) may appear identical to a therapeutic modality (the same specific eye motion), the intensity and/or quantity in the game mechanic may be insufficient.

In some embodiments the interactive digital carrier may be evaluated to determine if the quantity and/or intensity of the mechanic may be increased to a therapeutic level. For example, a game theme may be repurposed and/or created that utilizes the game mechanic in a high enough quantity to eventually reach a therapeutic value while preserving or increasing playability of the game. In some embodiments a required therapeutic level may interfere with the playability of the game (e.g., requiring too frequent and/or exaggerated eye motion which may interrupt the theme and/or environment of the game). Interference with the playability may, for example, cause reduction or cessation of a therapeutic delivery mechanism (such as dopamine production). In some embodiments a modification of the augmentation and/or adaptation of the game (e.g., increased level of the mechanic) may be suggested. The suggestion may be evaluated (e.g., automatically according to predetermined thresholds, manually) for impact on the efficacy of the digital carrier (e.g., playability of a game). If a level profile of a therapeutic modality and/or game mechanic are incompatible, at least one potentially suitable modality and/or mechanic may be suggested.

In various embodiments at least one predetermined rule may be applied to determine if an augmentation and/or adaptation of an interactive digital carrier challenge with a therapeutic modality is suitable to maintain a challenge state. Some embodiments may, by way of example and not limitation, apply a third level of weighting to at least one such rule. For example, the proposed augmentation and/or adaptation may be evaluated to determine if a progressive challenge state may be created that maintains a balance of ease of accessibility to learn the game mechanic and increasing difficulty remaining in and enhancing the game theme. The rule(s) may, for example, measure whether a player may be able to progressively learn a skill (the therapeutic modality) while maintaining immersion (e.g., avoiding boredom and/or frustration). For example, maintain immersion may be achieved by maintaining an engaging state of being, to facilitate ongoing stimulus of the body's pleasure center(s). For example, a complicated therapeutic modality which requires concentration to physically master may overshadow a lighthearted theme. Accordingly, the therapeutic modality may be suggested (e.g., automatically) to be applied to the theme inducing intense concentration. For example, in such a treatment state, if the suspension of disbelief and/or the production of neural stimuli cannot be maintained, the patient may fail to enter or remain in a suggestive state and the therapeutic delivery mechanism may fail, and the therapy will fail. Accordingly, various embodiments may be configured to maintain the treatment state.

In some embodiments the therapeutic modality may be suggested for augmentation in a different portion of a game theme, play, and/or environment (e.g., introduction of a relative complex breathing pattern later in game play when the user is more captivated by the game play, such as when intent on reaching a longer-sought reward). In various embodiments a therapy modality and/or augmentation and/or adaptation parameters of a selected therapeutic modality more conducive to progressive introduction may be suggested. For example, at least one breathing modality may be suggested which may be introduced requiring little thought from a user (e.g., extending one breath by 2 seconds every minute). The breathing modality may progress (e.g., extending the breath longer and/or more frequently) as the game play progresses (e.g., associated with 'levelling up' and/or other rewards). For example, a breathing modality conducive to gradual introduction may be suitable for earlier introduction and/or less intensive game themes and/or mechanics than a complex physical motion.

In various embodiments at least one predetermined rule may be applied to determine if a therapeutic modality may be implemented as a challenge which utilizes a game mechanic "in canon." Some embodiments may apply, by way of example and not limitation, a fourth level of rating to at least one such rule. For example, the challenge may be required to preserve and/or enhance a game theme and/or environment. The rule(s) may, for example, require that the game provide opportunities and/or rewards to use the skill of the therapeutic modality reflexively. Accordingly, the augmentation may be required to create and maintain flow-state style play at each of multiple milestones towards mastery of the therapeutic modality. Various embodiments may suggest therapeutic modalities conducive to a particular game canon and/or games having a canon suitable for augmentation by a particular therapeutic modality.

In various embodiments one or more parameters may be customized based on a current state. In some embodiments, by way of example and not limitation, a challenge condition may be dynamically adjusted in response to input during delivery of therapy and/or training by an (interactive) digital carrier. For example, an adjustment engine (e.g., implement artificial intelligence and/or machine learning algorithms) may adjust a challenge condition in response to signals indicating whether a patient/player remains engaged with a therapeutic modality during gaming. For example, if the challenge state is too easy, a max score and/or other indicators of too high performance (e.g., physiological indications of user inattention and/or boredom such as eye motion away from an interface) may be detected. Accordingly, an adjustment engine may (automatically) increase the challenge state in response. The adjustment may, for example, be according to a predetermined profile (e.g., a TBP, GIP) and/or within a predetermined adjustment range. Again, if a challenge state is too hard for a player, failure to achieve a minimum score threshold (e.g., in a certain time period and/or at a certain stage of interaction) and/or or perform biological and/or mental functions, the adjustment engine may, for example, (automatically) reduce the challenge state until a satisfactory level of progress can be made.

Various embodiments may, for example, determine if a patient player remains engaged as a function of, by way of example and not limitation, amount of playing time, social interactions, and/or general rating of game satisfaction. In various embodiments a monitoring engine may, for example, monitor input from the user (e.g., textual, audio, video) to determine a satisfaction level. The monitoring engine may, for example, apply natural language processing to user input (e.g., in a chat room, on a review site, in user interaction in and/or out of the game environment) to determine if the user is expressing negative sentiment and/or dissatisfaction regarding the game. In response to the monitoring engine detecting a (predetermined) minimum level of satisfaction and/or not detecting a (predetermined) minimum level of satisfaction, the adjustment engine may adjust one or more parameters of the digital carrier (e.g., a challenge state, a rewards level, social interaction, intensity level). Various embodiments may, by way of example and not limitation, apply artificial intelligence (AI) and/or machine learning (ML) algorithms to measure, adjust, and/or conclude that a digital carrier is effectively delivering a challenge state, effecting reprogramming, and/or inducing a desired bodily function(s). Various embodiments may, for example, apply the AI and/or ML to determine whether a stimulus required to remain in and/or effect an unconscious learning state is being provided. For example, some embodiments may monitor whether stimuli provided are causing a user to continue to produce dopamine effective to induce a state of perceptual learning.

In various embodiments at least one predetermined rule may be applied to determine if an augmentation applies a challenge progression which progressively increases the need for reflexive use of a game mechanic/treatment mechanism. Some embodiments may apply, by way of example and not limitation, a fifth level of rating to at least one such rule. For example, minimum requirements for progressively increasing (e.g., monotonically, increasing minimum level thresholds) level of a therapeutic modality in the course of a game may be implemented. The progress may, for example, be provided as a (predetermined) level progression profile. Implementation of a level progression profile for a particular modality may, for example, advantageously induce subconscious adoption of the motor, sensory or autonomic functioning such that the modality becomes reflexive to a user. Accordingly, various embodiments may advantageously provide unconscious (re)programming of the treatment mechanism for the user. Various embodiments may, by way of example and not limitation, suggest at least one digital carrier having a positive (predicted) correlation to a level progression profile for a specific therapeutic modality, at least one therapeutic modality having a level progression with profile with a positive (predicted) correlation to a game (e.g., defined by a GAP), a (modified) level progression profile suitable for augmentation and/or adaptation of a particular game with a particular therapeutic modality, or some combination thereof.

In various embodiments at least one predetermined rule may be applied to determine if an augmentation and/or adaptation is supported by at least one social aspect of the interactive digital carrier. Some embodiments may, by way of example and not limitation, apply the fifth level of weighting to at least one such rule. For example, a rule(s) may determine if one or more social aspects within a game support a therapeutic game mechanic/treatment mechanism. Social support may, for example, determine if mastery of the therapeutic modality is rewarded socially. Social reward may include, by way of example and not limitation, recognizable stature and/or increased ability within a community (e.g., fellow game players). Various embodiments may, by way of example and not limitation, suggest a social support mechanic and/or profile for a proposed augmentation and/or adaptation, suggest a game having social aspects (predicted to be) supportive of a specific therapeutic modality, suggest a therapeutic modality (predicted to be) supported by at least one social aspect of a game, or some combination thereof.

In various embodiments at least one predetermined rule may be applied to determine if a socially supported mechanic (e.g., therapeutic modality, game mechanic) correlates to at least one physiological improvement outside of the digital carrier environment and/or social network. Some embodiments may, by way of example and not limitation, apply a sixth level of weighting to at least one such rule. For example, a (therapeutic) game mechanic may be required to correlate to functional physiological improvements outside the game state. Such mechanics may, for example, achieve a high(est) level of social support by social support in and out of the digital carrier. In various embodiments physiological improvement may include, by way of example and not limitation, increased physical ability (e.g., strength, calmness, mental control when facing stressors, blood pressure) and/or appearance. Various embodiments may, by way of example and not limitation, suggest game mechanics (predicted to be) correlated to translatable (out of the game environment/network) improvements, suggest therapeutic modalities which may be implemented in a game environment to induce translatable improvements, suggest GIP, TBP, and/or GAP parameter values (predicted to be) correlated to translatable improvements, or some combination thereof.

Augmentation and/or Adaptation (Augmentation) System

Various embodiments may, for example, provide an augmentation management system (AMS) (e.g., configured to manage adaptation and/or augmentation of an (interactive) digital carrier(s)). The augmentation management system may, by way of example and not limitation, monitor an interactive digital carrier, monitor a (predetermined) therapeutic modality implementation, monitor an implemented augmentation and/or adaptation, suggest a therapeutic modality for augmentation and/or adaptation, suggest an interactive digital carrier for augmentation and/or adaptation, or some combination thereof.

In an exemplary embodiment, an augmentation management system (AMS) may manage regulated therapeutic assets (TAs) in one or more unregulated non-medical environments (e.g., interactive digital carriers). In the exemplary system depicted below, the AMS includes a Treatment Asset Manager (TAM). The TAM may serve as a regulatory compliance engine (e.g., FDA Compliance Engine). Treatment Assets (TAs) may include, by way of example and not limitation, treatment and/or therapeutic modalities which may be included in an interactive digital carrier and/or in a therapeutic environment (e.g., a companion therapy app).

In various embodiments the treatment assets may be at least partially defined, by way of example and not limitation, by one or more TBP and/or GIP. Treatment assets may include, by way of example and not limitation, source code, digital media (e.g., audio, video, text, images), parameters and/or profiles (e.g., environment, behavior parameters, frequency profiles, intensity profiles, motion sequences, behavior sequences, media sequences, reward profiles), or some combination thereof. In various embodiments a profile may, for example, define one or more parameters as a function of time, input from a user, or some combination thereof.

Treatment assets may be processed through a regulatory (e.g., FDA) verification and validation system and/or process. For example, a verification and/or validation system may determine if a treatment asset complies with predetermined regulatory approved parameters. A verification and/or validation engine may, for example, monitor the treatment assets for changes relative to a predetermined regulatorily approved profile. Approved treatment assets a be stored in one or more repositories. The repositories may, for example, be compliant with one or more regulatory bodies (e.g., FDA).

The TAM may receive (proposed) treatment assets from a digital assets repository (DAR). The DAR may, for example, be uncontrolled (e.g., relative to a medical regulatory body). The digital assets repository may include, for example, digital assets which may include assets that may be therapeutically useful. The assets may include, for example, will assets which may correspond to physiological engagement with one or more users (e.g., motion, mechanics, mentation). In various embodiments the assets may include profiles defining attributes of physiological engagement such as, for example, GAPs.

An interactive digital carrier engine (IDCE) (e.g., a game engine) interact with the (uncontrolled) DAR to integrate various digital assets from the repository into one or more interactive digital carriers (e.g., games). The IDCE may, for example, be configured (e.g., by one or more predetermined asset integration profiles) to load one or more digital assets from the DAR for deployment by the IDCE to create an interactive digital carrier (e.g., game).

The IDCE may be managed using a project management, software management, and/or (software) 'bug' tracking tool, such as a game development environment (GDE). The GDE may, for example, not be overseen and/or approved by a regulatory agency (e.g., FDA). The GDE may interact with the IDCE to integrate digital assets, including uncontrolled digital assets and/or treatment assets (e.g., from the TAM). In some embodiments and uncontrolled digital asset may, for example, be integrated into an interactive digital carrier and a treatment asset profile (e.g., TBP, GIP) may be applied such that the uncontrolled digital asset may operate as a (regulated) treatment asset.

The TAM may further be operatively coupled to at least one regulatory management tool (e.g., FDA compliance risk assessment, regulatory requirements, project management, and/or compliance good management practices (cGMP) toolkit). Treatment assets of the TAM may, for example, be designed, reviewed, and/or monitored for (health) risk and/or regulatory oversight issues and/or events using the regulatory management tool. Accordingly, the treatment assets may be subjected to cGMP processes.

The ASM further includes a deployment layer. The deployment layer integrates the interactive digital carrier developed using the GDE with the treatment assets from the compliant repository into a single interactive digital carrier (e.g., videogame). The IDCE may, for example, the uncontrolled and/or unregulated by (medical) regulatory bodies. The treatment assets may, for example, be regulated and/or approved by at least one (medical) regulatory body. Accordingly, the interactive digital carrier may advantageously deliver regulated and/or approved therapeutic digital assets using an uncontrolled interactive digital carrier. Various embodiments may advantageously permit rapid development and/or modification of an interactive digital carrier without undue regulatory burden. Accordingly, various embodiments may advantageously permit therapeutic assets to be delivered using cutting-edge, constantly improving, and/or user-engaging interactive digital carriers.

For example, in various embodiments the TAM may evaluate some or all digital assets from an (uncontrolled) DAR, an IDCE, or some combination thereof. The TAM may, for example, (manually and/or automatically) assign a risk score and/or risk profile to each digital asset. The TAM may, for example, determine that a digital asset over a (predetermined) risk threshold and/or matching a (predetermined) risk profile is a (controlled) treatment asset. The TAM may, for example, determined that the digital asset below a (predetermined) risk threshold and/or not matching a (predetermined) risk profile is an uncontrolled and/or non-treatment asset. Accordingly, various embodiments may permit existing and/or new uncontrolled digital assets configured to induce dopamine generation in users in a non-therapeutic environment to be integrated into an IDCE which may advantageously deliver (controlled) treatment assets in a form which advantageously increases patient compliance and/or achieves neural plasticity.

For example, in various embodiments an interactive digital carrier (e.g., a 3D engine, game environment(s), social interactions, game rewards structures, game imagery, game audio) may be non-therapeutic. A treatment mechanism may, for example, be provided by a treatment asset(s) (e.g., defined by at least one TBP). The treatment mechanism may, for example, be correlated to at least one (uncontrolled) interactive digital mechanism (e.g., game mechanic). The treatment mechanism may, for example, exist in the interactive digital carrier only when a specific parameter profile (e.g., frequency, speed, intensity) is achieved. In some embodiments the treatment mechanism may not exist in the interactive digital carrier. For example, a non-therapeutic game mechanism (e.g., breathing mechanics, eye-motion mechanics, body motion mechanics, mentation mechanics) may be delivered in an interactive digital carrier. The nontherapeutic mechanism may, for example, be learned by a subject using the interactive digital carrier. A correlated treatment mechanism may, for example, be deployed in a therapeutic environment and/or carrier (e.g., using a companion app) to employ the (previously learned) mechanic in a therapeutic modality (e.g., control of blood-pressure, hyperventilation, anxiety, physical weakness). Accordingly, the interactive digital carrier may be nontherapeutic because it does not define a final outcome of a therapy.

In various embodiments the ASM may correlate uncontrolled digital assets and treatment assets. In various embodiments the ASM may monitor an interactive digital carrier and/or integration of treatment assets into an interactive digital carrier to prevent unapproved implementation of treatment assets into the interactive digital carrier. For example, the ASM may prevent may mechanics from exceeding predetermined TBPs. As an exemplary illustration, a treatment asset may define a breathing mechanic (e.g., deep, calming breathing). The treatment asset may be integrated into an interactive digital carrier such that a player in the gaming environment is guided to and/or rewarded for implementing the breathing mechanic. The ASM may monitor implementation of the treatment mechanic to prevent unapproved implementation. For example, the ASM may block implementation of the mechanic during other motion (e.g., increased physical exertion), when not associated with predetermined behavior (e.g., sitting still), parameters outside of predetermined ranges (e.g., minimum breaths per minute, maximum durations and/or intervals of each breath, minimum oxygenation as determined by at least one sensor monitoring a player), or some common thereof.

Treatment States

Various embodiments (e.g., using an AMS) may classify treatment assets and/or treatment modalities that induce a desired state and apply them to enter the first treatment state and/or the second treatment state. For example, modalities may be classified for general use (e.g., widely applicable) and/or individual use (e.g., custom treatment modalities). In various embodiments treatment modalities may be identified and/or classified using imaging. Imaging may, for example, include (functional) magnetic resonance imaging (MM). For example, some embodiments may deliver proposed medicinal media (e.g., at least part of a treatment asset) to one or more users while monitoring at least one portion of the user's brain using (f) MRI to determine an area(s) of the brain stimulated by the media. The results may, for example, be correlated to a desired area of brain stimulation and/or to stimulation patterns associated with a desired effect (e.g., physiological behavior, pattern, motion, mentation). In various embodiments at least one AI and/or ML algorithm may be applied to (automatically) detect correlations between digital carriers and/or treatment modalities, and desired effects (e.g., a desired learning and/or treatment state).

In some embodiments, results of proposed media may be analyzed using machine learning and/or artificial intelligence to generate a model of therapeutic effect. In various embodiments classification may, for example, be performed at least partially by prompting for and/or recording and analyzing user responses (e.g., externally observable behaviors, monitored physiological responses, responses to questions about feeling/emotion/behavior/mood) before and/or after exposure to a proposed therapeutic modality. Various embodiments may be configured to adjust medicinal media in response to classification results in order to stimulate at least one brain area (e.g., ventral tegmental area) to achieve at least one desired physiological effect (e.g., dopamine production).

Accordingly, various embodiments may provide methods for (automatic) induction of neural plasticity and perceptual learning. Some embodiments may, for example, provide a system for auto-inducing perceptual therapeutic learning. For example, in some such embodiments, audio, visual, tactile, motor, and/or social stimuli may be provided to a user to induce the user's ventral-tegmental area to generate dopamine. As an illustrative example, a (predetermined) stimulus profile may be delivered (e.g., in an interactive digital carrier) to treat a speech disorder by inducing a state (e.g., the second treatment state) to induce chemical compound generation that causes the patient to reduce stuttering (e.g., by positive feedback). Accordingly, the patient may be receptive to therapy and/or perceptive training. Various embodiments may, by way of example and not limitation, be configured to treat autism by inducing neural plasticity (e.g., by stimulating endogenous dopamine production) before delivering a physiological and/or psychological training (e.g., behavior training, interaction training) via perceptive (e.g., sub-conscious) training.

Exemplary Immersive Digital Therapy

For example, in various embodiments user behavior (e.g., during immersion such as game play, during treatment such as by a companion app) may, for example, be monitored by a smartphone (e.g., microphone, accelerometer, GPS, camera, touch sensors, gyroscope, force sensors, pressure sensors). In various embodiments user behavior may, for example, be monitored using a game center. For example, various embodiments may employ a joystick, game wand (e.g., having accelerometer, gyroscope, audio sensor, and/or camera), steering apparatus (e.g., steering wheel), touch input (e.g., for hands, feet), trackball, wearables (e.g., wrist, head, other appendages, trunk, mouth), eye tracker, or some combination thereof. Feedback to the patient may, by way of example and not limitation, include haptic (e.g., vibratory, tapping, pressure/force feedback such as in a joystick or steering apparatus), audible (e.g., in a speaker, headset, helmet), visual (e.g., on a phone, computer, and/or wearable display, virtual reality display), or some combination thereof.

In an exemplary embodiment, a virtual reality (VR) based ski racing game (e.g., defined by a GAP) may be integrated (e.g., with at least one GIP) with a TBP associated with use of abs and quads to support body. The game may, for example, encourage the user to reposition the body in the race position to achieve the mechanics and/or motions defined by the TBP(s). The game theme may, for example, place the player in a positive challenge mode. A player's speed and score may, for example, be greatly increased by holding proper positioning (e.g., as defined by at least one of a TBP and GIP). The theme, visuals, audio, haptics, sensory and social aspects of the game (e.g., defined by a GAP, GIP, TBP, or some combination thereof) encourage and reward the strengthening and repositioning of the body for better ergonomics while distracting the player with the theme, challenge, interactivity, and social aspects of the game (the "immersion" such as, for example, defined by the GAP). The participant may do this readily, attracted to the game play and unaware to the remapping the brain is doing. Accordingly, the user playing the game may change fundamental physiological mechanisms (e.g., posture, musculature).

Over time, a patient player may, by way of example and not limitation, find that it is (1) easier to walk up hills, (2) they have less lower-back pain, and/or (3) they have more endurance. These advantages may be discovered, for example, outside the game environment. The patient may, for example, never fully recognize the consistent reprogramming received during the gaming.

In various embodiments what actually happened may include that, while playing the game the player was encouraged and distracted (e.g., in an altered state of reality—an "immersive state") to increase muscle tone and change how the body autonomically used muscles to align the back and support the body's structure. Accordingly, physiological function may be improved outside of the game environment.

Various embodiments may, by way of example and not limitation, augment video game(s), virtual reality, and/or augmented reality as an interactive digital carrier. A matrix (e.g., of predetermined rules) may be applied (e.g., manually and/or automatically) to determine a confluence point between at least one game theme/story and at least one biologically beneficial game mechanic implemented in a treatment regime. Various such embodiments may, for example, create a flow-state where subconscious entrainment drives neural plasticity to arrive at a fundamental physiological autonomic change in the body. The change may, for example, positively impact physiological function. The change may, for example, be (be capable of being) broadly applied beyond the base level training mechanism (e.g., the game).

In various embodiments, social support may, by way of example and not limitation, include acclamation of and/or request for guidance in attaining a specific skill. For example, a specific game mechanic (e.g., a virtual attack sequence) successfully implemented may be requested for 'tips' by other users and/or recorded, shared, and receive admiration. Accordingly, a user may be encouraged to acquire further prowess in the mechanic(s), thereby reinforcing the associated therapeutic modality.

For example, attack planning and placement in a game may be cross engineered with elements with cognitive rehabilitation and/or fine motor skills training. The association may, for example, be clinically documented. Various such embodiments may, for example, be provided to treat traumatic brain injury, COVID long haulers with mental processing issues, or some combination thereof.

Exemplary Therapy Delivery States

In various embodiments an interactive digital carrier may, by way of example and not limitation, be configured to be in one of two delivery states: no therapy, or positive therapy. An interactive digital carrier may, for example, be configured as a subconscious treatment mechanism. Various embodiments may advantageously enable advantages features of a digital carrier (e.g., a video game) to remain intact. Various embodiments may advantageously avoid breaking neural-plasticity-inducing features of a digital carrier by applying only some features of the carrier (e.g., by attempting to make a game out of a treatment instead of delivering a treatment modality via a game as a carrier). Various embodiments may advantageously enable games to effectively be used as a carrier to treat physiological disorders. Various embodiments may, for example, provide at least one process and/or system for identifying an existing modality in an interactive digital carrier, the existing modality being capable of inducing a desired (physiological) state. Such embodiments may apply the induction mechanism (e.g., dopamine oxytocin, endorphins, and/or serotonin generation, neural plasticity induction, suspension of disbelief) to deliver a therapeutic modality.

Exemplary Dynamic Therapy

In some embodiments, a method of dynamically altering treatment methods may be performed by a computer system. For example, a (treatment and/or training) delivery device (e.g., a medical device, a non-medical device) may communicate with a cloud-based server. In some embodiments, the cloud-based server may act as a SAAS (software as a service) model and/or interface with remote servers in a license/seat model. A decision engine may operate remotely in some embodiments. In an exemplary embodiment a decision engine may operate locally (e.g., a decision engine may be included in the medical device). A neural network or other machine learning algorithm may be accessible to the decision engine.

In some embodiments, a delivery device may communicate with the cloud via a wireless interface. In some embodiments, an app for a mobile device may interface with a cloud-based server. In an exemplary embodiment the app may communicate with the delivery device. In this way, the app could serve as an intermediary between the cloud-based server and the delivery device. In an exemplary embodiment, an app template may be provided to delivery device manufacturers and/or interactive digital carrier developers to facilitate dynamic treatment behaviors for delivery devices and/or interactive digital carriers that these manufacturers develop.

Exemplary Immersive Digital Therapy and/or Carrier

In various embodiments, a mechanism of action and substantial equivalence may include, for example, a therapeutic modality including directed physical stimuli leading to exertion, guided breath, movement, and/or sounds. The physical stimuli may be configured to induce self-soothing and/or calming. The physical stimuli and associated results may, for example, be provided in an acute treatment environment. The physical stimuli and associated results may, for example, be provided in a prolonged treatment approach. For example, in some embodiments the therapeutic modality may be implement such that a patient reaches entrainment where a learned technique is substantially preventative for some duration of time.

Various embodiments may use game action to induce mild anxiety and/or increased physical exertion events (e.g., moments, periods). Breathing patterns, motion patterns, other biological indicators (e.g., heart rate, blood pressure) of physical and/or emotional stress and/or distress, or some combination thereof, may be monitored (e.g., measured, recorded, tracked).

Various embodiments may display patient breathing as a biofeedback mechanism. In some embodiments additional biological indicators and/or patterns may be included in the (displayed) biofeedback mechanism. Examples of such indicators and/or patterns may include, but are not limited to, light, sound, haptics, spatial orientation, animation, movements, other visual and/or auditory clues and/or displays, or some combination thereof.

Various embodiments may provide additional feedback mechanisms configured to instruct the player (e.g., patient) how to breathe and/or move to reduce anxiety and/or stresses. For example, in some embodiments the feedback mechanisms may be in response to physical body reactions corresponding to emotional distress. In some embodiments the feedback mechanisms may be configured to induce the patient to perform physical body reactions corresponding to reduced and/or eliminated emotional distress (e.g., calming mechanisms).

Exemplary embodiments may include, taken singly or in various combinations, overlaying lights, new sounds, changing tones, additional animations, other visual/auditory guidance showing the patient how to change movements, sounds, thinking, and/or breathing, or some combination thereof. In various embodiments the feedback may be operated to guide the patient to achieve a calm state.

Various embodiments may be configured to preserve a play action such that patient compliance aspects of a game. For example, the game's inherent gripping, immersive, characteristics and/or attractiveness may be key to a patient continuing to use the device with much greater frequency than is normally experienced with traditional patient driven therapeutics. A cycle of play may, for example, incorporate calming mechanisms as a time limited portion of the game that may provide the player with special abilities to excel in the game (e.g., a bonus action, a state with improved ability to score and/or achieve mastery in the game).

In an illustrative example, in a shooter style game, a player may be guided, while monitored through biofeedback, to breathe, move, create sounds, and/or think/process in a way configured to induce stress relief and calming. The more successful the player/patient is at achieving and maintaining the state, the more game benefit they may be awarded. This state may, for example, be implemented in bullet time in a game. For example, in such embodiments, the 'enhanced' game mode may, for example, require the player to demonstrate an ability to transition from an anxiety state to a calmer state. Such modes may be referred to, by way of example, by exemplary titles such as Zen mode, flow state, matrix like environment, or some combination thereof. In such embodiments, the patient (player) may advantageously be taught self-soothing techniques such that they learn how to consciously and/or unconsciously reduce stress during an anxiety and/or depressive disorder.

Various embodiments may, for example, provide a game/treatment device with a treatment mode that is only a calming mode. The treatment mode may implement at least one biofeedback mechanism to assist/treat patients (using the same learned behavior and guided biofeedback mechanism) during a non-game induced (real world) event. The event may, by way of example and not limitation, include a 'real-world' manic, depressive, anxiety, and/or or panic-based event.

An illustrative example of such embodiments may, for example, include a shooter style game, without violence (e.g., using non-violent mechanisms to induce movement in the style of beat saber or pistol whip). During "rev up" times game action may, for example, be used to create and/or increase intensity.

Player/patient (PP) monitoring may, for example, follow breath and, in response, display breathing patterns as light, sound, and/or haptics. In some embodiments, when the monitoring detects the PP is in a heightened state and the game play supports the transformation, the PP may be guided to enter a calming state where they are coached to take control of their breathing to calm down. The biofeedback mechanism may, for example, demonstrate where breathing patterns should be. In some embodiments, the closer the PP can match the calming mechanisms (e.g., guided by the biofeedback), the longer they may remain in the calming mode. The calming mode may, for example, provide (significant) bonus game benefits. Such benefits may, in various embodiments, include, by way of example and not limitation: enhanced scoring ability (e.g., moving in a slow-motion matrix like state); buff state, score multipliers, and/or combos; captivating visuals; a visual feel becomes beautiful, enhanced, and/or very appealing (e.g., a dream state); coaching/calming voices and/or soothing sounds; ability to defeat certain boss-like opponents and/or attain certain levels (e.g., otherwise unattainable); (enhanced) ability to defeat other players and/or overtake their abilities (e.g., in a multiplayer environment).

In some embodiments, PP tracking (e.g., duration, frequency, successful usage) may be configured to factor into an overall leaderboard score and/or into capabilities of the player. Various embodiments may be configured to track PP moods and reflections (e.g., over a session, across multiple sessions) such as, by way of example and not limitation, overall sense of well-being. Such embodiments may, for example, provide trending tools for caretakers (e.g., physicians) and/or for the PP to find paths back to a calmer and/or healthy living conditions when undesirable events (e.g., anxiety episode, depression episode, related disorders) (re-)emerge as trends in the PP's life.

In some embodiments a treatment mode may be provided. For example, if a PP is having a real life need for biofeedback-led treatment (e.g., a panic attack, sustained anxiety, or depression) the PP can enter the treatment mode and use the now familiar mechanism to achieve calming, self-soothing, and/or a rebalance of emotions.

In various embodiments, the game may include one or more TDAs. The TDAs may, for example, demonstrate safety and effectiveness. In some embodiments, only the treatment mode and/or associated TDAs may be VV as a medical device. Accordingly, various embodiments may limit a portion of the game/code that may require ongoing management per regulatory requirements.

In various embodiments, devices may advantageously leverage a fun and/or compelling nature of a game, and augment the game with at least one Calm mode, while maintaining the game's integrity. Various embodiments may thereby achieve patient compliance at a much greater rate than normally achieved by traditional medical devices and/or therapies. In embodiments with a treatment only mode, the game and Calm mode may, for example, only be a training tool. The Calm mode and associated game play may, for example, not be therapeutic in some embodiments. In various embodiments, the game play can be a priority in the game (teaching mode). Such embodiments may advantageously preserve the integrity of the game and/or reduce regulatory burden.

Exemplary Calming Mode Embodiments

Some embodiments may include a "Zen Mode" or "Bullet Mode." Exemplary traits of such modes may include, for example, spectacular visuals, soothing sounds, and/or (unexpected) use of motion. In some embodiments this aspect of a game may beneficially emphasize breathing. which should both play into how Calm Mode is reached, and how it is presented. Calm mode may be constructed into the game in various implementations. Some examples may, for example, reach "Calm Mode," which may be configured to affect/change gameplay.

For example, visual, auditory, and/or motion-based changes may occur when Calm Mode is activated. Some implementations may advantageously incorporate one or more senses into the main mechanic of breathing.

Normal (e.g., conventional) gameplay may create an environment replicating, for example, anxiety. As gameplay goes on, the speed and difficulty may increase. This, in tandem, may cause a heart and/or respiration rate of the player to increase.

In accordance with various exemplary embodiments, when the player reaches a certain point of respiration rate, Calm Mode may activate automatically. In some embodiments a Bullet Mode may, for example, be activated in tandem with Calm Mode. In some embodiments Bullet Mode may not require Calm Mode to be activated. In some embodiments, if the player gets their score to a high enough threshold, they may, for example, manually activate Calm Mode if they begin to feel overwhelmed and/or if they want to increase their score further. Such embodiments may, for example, encourage prolonged play, which may advantageously increase effectiveness.

When in Calm Mode, gameplay may, for example, slow down dramatically. The player may, for example, be instructed to mimic a visual in order to calm their breathing. Every completed breath cycle may, for example, not only add to the player's score, but may also guarantee that they receive buffs that carry on until a next round of Bullet Mode.

In some embodiments an environment may shift. Colors and/or shading may, for example, shift into warmer hues. Music accompanying gameplay may, for example, be replaced with tracks that rhythmically follow a breathing pattern that has been initiated and/or induced. A use of visual and/or auditory stimulation may, for example, help combat ADD. Brainwaves may, for example, synchronize with the beat of music. A player's mind may, for example, associate slower rhythms with meditative, calming states, and/or faster rhythms with productivity and/or alert states.

In some embodiments movement may be incorporated into a Bullet Mode function (e.g., in a Calm Mode). Some such embodiments may, for example, correspond to Tai Chi-related methods. Tai Chi type motions, may, for example, be healthy if done for prolonged periods. Such motions may, for example, improves a patient's mood and/or help with stress and/or anxiety.

Auditory, visual, and movement-based aspects of Calm Mode may, for example, be configured to coordinate with the main focus of breathing to help teach the player methods of stress reduction. The music may, for example, be deployed as both a beat to help the player's brain adapt to the rhythm of breathing and help them tune into their environment. Whereas the movement may function as a way to keep gameplay interesting and/or may advantageously help show the player method(s) of reducing anxiety and stress (e.g., the main premise of Bullet Mode). In some embodiments the movement may, for example, advantageously serve as a method of stress release on its own.

The movement may, for example, be configured to feed into gameplay. For example, it may be configured to be a primary way of blocking and/or dodging incoming attacks while in Calm Mode. Calm Mode may, for example, be only a temporary stage outside of "Treatment Mode." When it ends, the player may be granted benefits based on their breathing. In various embodiments, such (game) benefits may, for example, include drastic offensive capability. Such benefits may, for example, give the player an opportunity to get their score to drastic new heights. Such benefits may, for example, be configured to be necessary for the player to achieve other stages of play. Accordingly, such embodiments may be configured to create a positive feedback loop which would ensure the player wouldn't pass over Bullet Mode (e.g., Calm Mode) altogether in favor of normal gameplay.

In various embodiments, symbols (e.g., sigils) may be associated with achieving certain effects in game play (e.g., imaginary world effects). Sigils may, for example, be drawn using VR hand-controllers during gameplay. Normal sigils (e.g., less complicated symbols requiring less strokes and/or less time to draw) may, for example, be deployed in a faster-paced section of the game. Such normal sigils may, for example, be designed to be minimalist. For example, normal sigils may be configured to be easily drawn with one hand within 3 seconds.

Slow-mode sigils (e.g., Slomo-sigils) may only be active in a game during a Calm mode, during which the game's time may, for example, slow to a creep. The slowed timing may, for example, grant the player an opportunity to do breathing exercises while drawing more intricate symbols with the hand-controllers. These more complicated Slomo-sigils may, for example, activate major effects in the gameplay. Such effects may, for example, eliminate a large portion of hostile non-player characters (NPCs) and/or give a large boost to the player's health points (HP). In some embodiments, such complex symbols may, for example, be configured to give an engaging activity to the player that doesn't overwhelm them.

In some embodiments, a (secondary) mechanic may be implemented in which symbols (e.g., runes) are configured with multiple variants having increasing levels of complexity. Increased complexity symbols may, for example, grant a player increased benefits (e.g., a progressively larger buff depending on the level of complexity).

For example, if a player is trying to initiate an imaginary-world attack effect, the player may choose from two variants. A first variant may, for example, take less time to draw then a second variant. However, the second variant may result in more damage to opponents. This tradeoff decision may, for example, add a dimension of strategy to gameplay. Such embodiments may, for example, increase a player's enjoyment of the experience.

Exemplary Digital Light Treatment

Various embodiments disclosed herein may advantageously provide light therapy via delivery of media types including, by way of example and not limitation, virtual reality (VR), near VR (e.g., smartphone-based VR-like platforms, methods, apps, systems such as Google Cardboard), various other media types, or some combination thereof.

Delivering light therapy using traditional systems and/or methods may often include issues of patient compliance due, for example, to the following concerns:

(1) Lightboxes may be big and bulky and may require the patient to remain in the treatment area for 30 or more minutes.
(2) Smaller light boxes or glasses may be very intense, may cause headaches, and may not allow the patient to do other activities while receiving therapy.
(3) Traditional treatment devices (such as described above) may be conspicuous, and so may identify the patient as someone with a particular condition.
(4) It may be difficult to do other work or focused work during treatment, the therapy may be seen as boring, or the patient may simply not have time for the treatment in the day, so a patient may skip treatments. Skipped treatments may greatly reduce the effectiveness of the treatment and ultimately may cause relapse of the treated condition.
(5) It may be difficult to track and definitively quantify how much light a patient has received each day and, therefore, determine what "dose" the patient has received.

Accordingly, various embodiments may advantageously deliver light therapy via treatment media which is, for example, convenient, entertaining, productive, or otherwise desirable to a patient. Treatment media may, for example, be predetermined (e.g., prescribed by a doctor, therapist, or wellness coach). Treatment media may be patient-selected from predetermined media (e.g., from at least one predetermined library). Treatment media may be completely user determined.

In various embodiments media may include video content such as, by way of example and not limitation, movies, feature films, crowd-sourced video, short films, documentaries, news, training videos, humor, motivational videos, recorded sermons, or some combination thereof. Media may, for example, include digital reading material, such as, by way of example and not limitation, ebooks, online reading, streaming content, internet browsing, or some combination thereof. Media may include, for example, (interactive) environments. For example, media may include games (e.g., video games). For example, media may include video games including one or more (responsive) therapeutic modalities. The therapeutic modalities may, for example, be selected according to a TCP. The therapeutic modalities may, for example, be monitored by a (remote) validation and/or verification system. In some embodiments media may, for example, include direct light output.

Predetermined treatment media or media types may, for example, be quantified as producing predetermined therapeutic dose(s) of light, wavelength(s) of light, or some combination thereof. Predetermined treatment media or media types may, for example, be selected to fulfill one or more prescribed treatment parameters. Treatment parameters may, for example, include duration, intensity, wavelength, or some combination thereof.

Exemplary hardware apparatus for receiving a light emitting device may, for example, be configured as glasses with a structure for receiving a smartphone or other suitable portable media delivery device suitable for delivering treatment media. The hardware apparatus is provided with at least one light sensor for each eye and with a phone interface. The light sensors may be configured to detect dosage-related properties of light (e.g., duration, intensity, or wavelength). The output from the light sensors, may, for example, be transmitted via the phone interface to an app running on the smartphone.

In an exemplary hardware apparatus for receiving a light emitting device, a smartphone may be disposed in a hardware apparatus. The hardware apparatus may, for example, include a cardboard box or other suitable construction for positioning the smartphone to emit light on a desired portion of the user's body. The hardware apparatus may, for example, advantageously position the smartphone to display light to a user's eyes at a predetermined distance.

The smartphone may, for example, be running an app delivering treatment media. The smartphone may, for example, be running an app determining dosage delivered to the patient by the treatment media. In various embodiments, the apps may be different apps, may be a single app, or some combination thereof. In some embodiments, some function(s) of the apps may be performed on a server.

In an exemplary embodiment, a hardware apparatus may receive or be attached to a light emitting content delivery device (LECDD) such as, for example, a smartphone or VR headset. The hardware apparatus may measure the light emitted by the LECDD. The LECDD may be operated, for example, to deliver certain therapeutic doses of light via an app configured to deliver light therapy via predetermined media. The app may, for example, receive data from the hardware apparatus and calculate therefrom a light dose the patient has received. The app may, for example, then solicit the patient to receive feedback on how they are feeling. The app may then use that feedback to determine at least one optimal dose of light to treat the patient.

In various embodiments, specific treatment media may be pre-calibrated by measuring the light emitted when the treatment media is delivered. The pre-calibration may be performed, for example, in a testing location, by a user, or some combination thereof. The pre-calibration may, for example, be specific to a predetermined LECDD, to a viewing configuration (e.g., viewing distance, positioning apparatus such as viewing goggles and/or headset), or some combination thereof. The pre-calibration may measure ambient light to determine only the light emitted by the LECDD.

In some embodiments, the pre-calibration may be multi-part. For example, predetermined treatment media may be profiled on a reference LECDD and assigned a light-emission profile (e.g., score, value, or parameters). A specific configuration (e.g., specific LECDD, a delivery configuration, or some combination thereof) may be profiled using at least one reference treatment media, and a configuration light-emission modification profile (e.g., value or values) be applied. An app may then, for example, determine the dose provided to a user as a function of the treatment media's light-emission score and the specific configuration light-emission modification value. Such embodiments may advantageously allow treatment media to be pre-calibrated, while retaining accuracy across multiple devices (e.g., different devices shine brighter, produce different wavelengths when delivering the same treatment media, or other variables), while also minimizing inconvenience and expense in pre-determining every treatment media and configuration combination.

In various embodiments, light therapy may be dynamically determined. For example, the hardware apparatus may repeatedly (e.g., at predetermined intervals or continuously) measure light emitted by the LECDD as treatment media is delivered to a patient. The app may, for example, determine light therapy dose as a function of duration and light intensity per unit time. The app may then, for example, display the dose of light therapy received and may, for example, compare the dose received to the prescribed dose or predetermined dose. In some embodiments, a self-calibrating system may be provided wherein a LECDD, treatment media, or both is calibrated during use by a patient. For example, a light measurement device may measure light emitted during delivery of treatment media by an LECDD. Either the treatment media or LECDD may, for example, be pre-calibrated, and while the patient is receiving the treatment media the un-calibrated component may be calibrated. Later, the patient may use the calibrated combination, or an equivalent combination (e.g., reading e-books with a pre-calibrated ratio of text to white space), without the light measurement device. Various embodiments provided with calibration may advantageously permit compliance with guidelines and regulations promulgated and enforced by medical and health regulatory bodies such as the US Food and Drug Administration.

In various embodiments, the hardware apparatus may, for example, continuously (e.g., by 'spot' measuring at predetermined time intervals, or measuring constantly) measure all use of a LECDD (e.g., a smartphone). The resulting data may, for example, be processed (e.g., by a server running software instructions, by a mobile computing device running an app, or other suitable computing system) to calculate one or more light exposure metrics. Such metrics may include, by way of example and not limitation, total light exposure, light exposure over one or more specific time periods, light exposure per unit time (e.g., hour, day, week, or other unit), or some combination thereof. In various embodiments, hardware apparatus may include one or more light detection sensors configured to measure all light received by a user (e.g., ambient light, light emitted by one or more devices, light emitted by treatment media, other light, or some combination thereof) on at least one portion of the body (e.g., eyes, face, limbs, trunk, or other target body portion). In various embodiments, metrics may be calculated without directly measuring light by a light detection sensor. Such embodiments may, for example, be calculated by monitoring device usage and using precalibrated or estimated light output values to calculate light emitted.

In various embodiments, treatment media may be themed. Themed treatment media may, for example, advantageously further enhance the intended treatment. As an example, beach scenes delivering an average 10,000 Lux of light for a minimum of 30 minutes could be used to treat Seasonal Affective Disorder (SAD), simultaneously entertaining and calming the patient. Accordingly, the patient may be treated for the clinical disorder while also being provided wellness-based support for the concomitant high anxiety which may be experienced by many SAD patients.

VR headsets may be prohibitively expensive for various users. VR headsets may not currently have a strong market overlap with SAD sufferers or other users of light therapy. In various embodiments, patients not wishing to purchase a VR headset, may advantageously be provided with accessories to convert a smartphone or any handheld computer-based device that is capable of delivering treatment media. The accessories may, for example, position the phone at a predetermined distance from the face to deliver the treatment media safely and effectively.

Various embodiments may be implemented in the context of various medical uses, therapeutic uses, wellness uses, sports uses, or some combination thereof. Some embodiments, for example, may be implemented in the context of biorhythm or circadian rhythm-based functions. Such functions may include, by way of example and not limitation, analysis, adjustment, or resetting of sleep patterns; optimization of digestion; optimization of metabolism of pharmaceuticals, nutraceuticals, or other compounds; or some combination thereof. For example, measurement of light received by a user may be used as a metric to determine a current rhythm, and may be used, for example, in diagnosis of a condition, in identification of potential avenues for health and wellness optimization, in guiding a user to adjust rhythms (e.g., indoor/outdoor exposure patterns, device usage patterns, sleep patterns), other appropriate uses, or some combination thereof. Various embodiments may be implemented in the context of non-medical uses. Such implementations may include, for example, health and wellness, emotional wellness, other appropriate uses, or some combination thereof.

Exemplary Hypertension Therapy Modality(ies) and/or Mechanic(s)

Various embodiments may involve a biofeedback mechanism that uses a wearable audio microphone. Software programming in the mechanism may, for example, interpret the breath sound to determine respiratory rate of a user. In some exemplary systems, the breath rate may be displayed back to the user via visual display and/or auditory sounds and/or haptics sensations. Various embodiments may specifically address patient compliance issues through the gamification of proven treatment modalities for chronic diseases.

The global prevalence of hypertension is high, and among nonpregnant adults in the United States, treatment of hypertension is the most common reason for office visits and for the use of chronic prescription medications. However, roughly one-half of hypertensive individuals may not have adequate blood pressure control. Suboptimal adherence with prescribed antihypertensive medication and lifestyle changes may contribute to the burden of uncontrolled hypertension.

In some embodiments, the "game" mechanics may be accessed via a portable computing device. Accordingly, the therapy (SaMD) may be advantageously accessible to patients throughout the day when stressful situations occur. Such embodiments may, for example, advantageously provide greater, cost-effective reach to underserved populations and/or further flexibility of treatment for hypertension.

Various implementations may benefit from an overlap between habit forming gaming mechanics and proven treatment mechanisms to solve for patient compliance issues. An overlap of certain gaming and therapeutic mechanisms may provide tremendous benefit overcoming compliance issues.

Various embodiments may provide confluence between gaming controls and effective hypertension treatment mechanisms, including, by way of example and not limitation, guided abdominal breathing, gross and fine motor movement, and exercise forms. In gaming, breathing has been studied for its ability to act as a compelling game mechanism, and has been found to be an excellent, but often untapped, game control mechanic. A study conducted in 2011 at the University of Nottingham found breathing, though in principle a one-dimensional interface medium, may actually be a subtle and viable control mechanism that can be used either as a control mechanism in itself, or to enhance a more traditional game interface, ultimately leading to a satisfying and immersive game experience.

Some studies suggest that guided breath through biofeedback can very successfully be taught; however, the ability to apply the skill to receive ongoing clinical benefit has not easily been achieved in time intervals tested. A 2019 NIH study concluded that biofeedback appears to be a useful tool in teaching specific abdominal breathing patterns, but additional training may be required to provide sustained clinical benefit.

Various embodiments may provide intrinsically captivating game play and overlap between movement and game control. These mechanisms may be transferrable to standard console, computer, and/or mobile gaming platforms. Accordingly, various embodiments may greatly expand ability to reach untreated patient populations.

Some embodiments may seamlessly integrate such behaviors into compelling game play. Further, in some examples, specific desired rewards within a gaming environment may be provided. Accordingly, such embodiments may advantageously encourage much more prolonged training. Participants may not even be aware of a level of conditioning they are receiving, such as when using treatment modes utilizing familiar actions and behaviors during self-guided therapy to address acute episodes of stress, anxiety, and depression.

Various embodiments may sense breathing with VR systems. Such embodiments may, for example, advantageously permit therapeutic systems to be implemented without the use of additional hardware. Breathing may be implemented as a critical portion of a game mechanic. Learning to use the control may provide significant reward to a player. Some embodiments may advantageously provide hours of breathing exercise over a course of use of the game and may improve an associated breathing technique over time. Various such embodiments may, for example, achieve such extended breathing exercise and/or training while advantageously avoiding arriving at fatigue level with the training prior to attaining clinical benefit.

In some embodiments a biofeedback mechanism may include earphones and a microphone. The earphones and/or microphone may allow the treatment mechanism to be deployed across multiple mobile platforms. Such embodiments may, for example, greatly increase accessibility and/or usability of the treatment. Such embodiments may, for example, advantageously drastically reduce a cost of the device.

In some embodiments implementing the breathing game-therapy, a user may advantageously gain the ability to induce stress in a controlled setting, emulating real word situations, from dealing with multiple stimuli to operating under extreme time pressure. The game environment may, for example, allow "real-time" to be slowed, so the patient may learn and practice (e.g., through biofeedback) visualized self-guided abdominal breathing mechanisms. Difficulty may, for example, gradually, over multiple game play sessions, be increased until the patient is able to deploy the techniques in real or near real time stressful situations.

In some implementations, a biofeedback mechanism may be validated based on microphone detection and/or algorithmic interpretation. Such embodiments may, for example, advantageously provide detection and/or interpretation substantially equivalent to accelerometer based breathing monitoring systems. In some examples, controlled breath may be employed as a game mechanic and/or as a training tool while maintaining or increasing a compelling nature of the game play.

Various examples may promote improved compliance with current lifestyle treatments for hypertension. Some embodiments may allow for improved blood pressure control in hypertensive patients. Some embodiments may apply an addictive nature of gaming to achieve positive behavioral modifications. Some embodiments may ultimately enable benefits for treatment of anxiety, stress, post-traumatic stress disorder, suicide prevention, or some combination thereof.

Various embodiments may advantageously enhance access to low cost, reliable mobile treatment. Some embodiments may directly impact a military's ability to address treatment under a diversity of treatment conditions. Anxiety and depression may, for example, be common in patients with uncontrolled hypertension and may confound blood pressure control. A study conducted by the National Institute of Health in 2013 found a significant correlation between systolic ($r=0.713$) and diastolic ($r=0.52$) blood pressure values and depression. In some implementations, improving blood pressure, anxiety, and/or depression management may advantageously lead to improved health outcomes for warfighters, their families, and/or the civilian population.

Exemplary Digital Light Treatment

Various embodiments disclosed herein may advantageously provide light therapy via delivery of media types including, by way of example and not limitation, virtual reality (VR), near VR (e.g., smartphone-based VR-like platforms, methods, apps, systems such as Google Cardboard), various other media types, or some combination thereof.

Delivering light therapy using traditional systems and/or methods may often include issues of patient compliance due, for example, to the following concerns:
(1) Lightboxes may be big and bulky and may require the patient to remain in the treatment area for 30 or more minutes.
(2) Smaller light boxes or glasses may be very intense, may cause headaches, and may not allow the patient to do other activities while receiving therapy.
(3) Traditional treatment devices (such as described above) may be conspicuous, and so may identify the patient as someone with a particular condition.
(4) It may be difficult to do other work or focused work during treatment, the therapy may be seen as boring, or the patient may simply not have time for the treatment in the day, so a patient may skip treatments. Skipped treatments may greatly reduce the effectiveness of the treatment and ultimately may cause relapse of the treated condition.
(5) It may be difficult to track and definitively quantify how much light a patient has received each day and, therefore, determine what "dose" the patient has received.

Accordingly, various embodiments may advantageously deliver light therapy via treatment media which is, for example, convenient, entertaining, productive, or otherwise desirable to a patient. Treatment media may, for example, be predetermined (e.g., prescribed by a doctor, therapist, or wellness coach). Treatment media may be patient-selected from predetermined media (e.g., from at least one predetermined library). Treatment media may be completely user determined.

In various embodiments media may include video content such as, by way of example and not limitation, movies, feature films, crowd-sourced video, short films, documentaries, news, training videos, humor, motivational videos, recorded sermons, or some combination thereof. Media may, for example, include digital reading material, such as, by way of example and not limitation, ebooks, online reading, streaming content, internet browsing, or some combination thereof. Media may include, for example, (interactive) environments. For example, media may include games (e.g., video games). For example, media may include video games including one or more (responsive) therapeutic modalities. The therapeutic modalities may, for example, be selected according to a TCP. The therapeutic modalities may, for example, be monitored by a (remote) validation and/or verification system. In some embodiments media may, for example, include direct light output.

Predetermined treatment media or media types may, for example, be quantified as producing predetermined therapeutic dose(s) of light, wavelength(s) of light, or some combination thereof. Predetermined treatment media or media types may, for example, be selected to fulfill one or more prescribed treatment parameters. Treatment parameters may, for example, include duration, intensity, wavelength, or some combination thereof.

Exemplary hardware apparatus for receiving a light emitting device may, for example, be configured as glasses with a structure for receiving a smartphone or other suitable portable media delivery device suitable for delivering treatment media. The hardware apparatus is provided with at least one light sensor for each eye and with a phone interface. The light sensors may be configured to detect dosage-related properties of light (e.g., duration, intensity, or wavelength). The output from the light sensors, may, for example, be transmitted via the phone interface to an app running on the smartphone.

In an exemplary hardware apparatus for receiving a light emitting device, a smartphone may be disposed in a hardware apparatus. The hardware apparatus may, for example, include a cardboard box or other suitable construction for positioning the smartphone to emit light on a desired portion of the user's body. The hardware apparatus may, for example, advantageously position the smartphone to display light to a user's eyes at a predetermined distance.

The smartphone may, for example, be running an app delivering treatment media. The smartphone may, for example, be running an app determining dosage delivered to the patient by the treatment media. In various embodiments, the apps may be different apps, may be a single app, or some combination thereof. In some embodiments, some function(s) of the apps may be performed on a server.

In an exemplary embodiment, a hardware apparatus may receive or be attached to a light emitting content delivery device (LECDD) such as, for example, a smartphone or VR headset. The hardware apparatus may measure the light emitted by the LECDD. The LECDD may be operated, for example, to deliver certain therapeutic doses of light via an app configured to deliver light therapy via predetermined media. The app may, for example, receive data from the hardware apparatus and calculate therefrom a light dose the patient has received. The app may, for example, then solicit the patient to receive feedback on how they are feeling. The app may then use that feedback to determine at least one optimal dose of light to treat the patient.

In various embodiments, specific treatment media may be pre-calibrated by measuring the light emitted when the treatment media is delivered. The pre-calibration may be performed, for example, in a testing location, by a user, or some combination thereof. The pre-calibration may, for example, be specific to a predetermined LECDD, to a viewing configuration (e.g., viewing distance, positioning apparatus such as viewing goggles or headset). The pre-calibration may measure ambient light to determine only the light emitted by the LECDD.

In some embodiments, the pre-calibration may be multi-part. For example, predetermined treatment media may be profiled on a reference LECDD and assigned a light-emission profile (e.g., score, value, or parameters). A specific configuration (e.g., specific LECDD, a delivery configuration, or some combination thereof) may be profiled using at least one reference treatment media, and a configuration light-emission modification profile (e.g., value or values) be applied. An app may then, for example, determine the dose provided to a user as a function of the treatment media's light-emission score and the specific configuration light-emission modification value. Such embodiments may advantageously allow treatment media to be pre-calibrated, while retaining accuracy across multiple devices (e.g., different devices shine brighter, produce different wavelengths when delivering the same treatment media, or other variables), while also minimizing inconvenience and expense in pre-determining every treatment media and configuration combination.

In various embodiments, light therapy may be dynamically determined. For example, the hardware apparatus may repeatedly (e.g., at predetermined intervals or continuously) measure light emitted by the LECDD as treatment media is delivered to a patient. The app may, for example, determine light therapy dose as a function of duration and light intensity per unit time. The app may then, for example, display the dose of light therapy received and may, for example, compare the dose received to the prescribed dose or predetermined dose. In some embodiments, a self-calibrating system may be provided wherein a LECDD, treatment media, or both is calibrated during use by a patient. For example, a light measurement device may measure light emitted during delivery of treatment media by an LECDD. Either the treatment media or LECDD may, for example, be pre-calibrated, and while the patient is receiving the treatment media the un-calibrated component may be calibrated. Later, the patient may use the calibrated combination, or an equivalent combination (e.g., reading e-books with a pre-calibrated ratio of text to white space), without the light measurement device. Various embodiments provided with calibration may advantageously permit compliance with guidelines and regulations promulgated and enforced by medical and health regulatory bodies such as the US Food and Drug Administration.

In various embodiments, the hardware apparatus may, for example, continuously (e.g., by 'spot' measuring at predetermined time intervals, or measuring constantly) measure all use of a LECDD (e.g., a smartphone). The resulting data may, for example, be processed (e.g., by a server running software instructions, by a mobile computing device running an app, or other suitable computing system) to calculate one or more light exposure metrics. Such metrics may include, by way of example and not limitation, total light exposure, light exposure over one or more specific time periods, light exposure per unit time (e.g., hour, day, week, or other unit), or some combination thereof. In various embodiments, hardware apparatus may include one or more light detection sensors configured to measure all light received by a user (e.g., ambient light, light emitted by one or more devices, light emitted by treatment media, other light, or some combination thereof) on at least one portion of the body (e.g., eyes, face, limbs, trunk, or other target body portion). In various embodiments, metrics may be calculated without directly measuring light by a light detection sensor. Such embodiments may, for example, be calculated by monitoring device usage and using precalibrated or estimated light output values to calculate light emitted.

In various embodiments, treatment media may be themed. Themed treatment media may, for example, advantageously further enhance the intended treatment. As an example, beach scenes delivering an average 10,000 Lux of light for a minimum of 30 minutes could be used to treat Seasonal Affective Disorder (SAD), simultaneously entertaining and calming the patient. Accordingly, the patient may be treated for the clinical disorder while also being provided wellness-based support for the concomitant high anxiety which may be experienced by many SAD patients.

VR headsets may be prohibitively expensive for various users. VR headsets may not currently have a strong market overlap with SAD sufferers or other users of light therapy. In various embodiments, patients not wishing to purchase a VR headset, may advantageously be provided with accessories to convert a smartphone or any handheld computer-based device that is capable of delivering treatment media. The accessories may, for example, position the phone at a predetermined distance from the face to deliver the treatment media safely and effectively.

Various embodiments may be implemented in the context of various medical uses, therapeutic uses, wellness uses, sports uses, or some combination thereof. Some embodiments, for example, may be implemented in the context of biorhythm or circadian rhythm-based functions. Such functions may include, by way of example and not limitation, analysis, adjustment, or resetting of sleep patterns; optimization of digestion; optimization of metabolism of pharmaceuticals, nutraceuticals, or other compounds; or some combination thereof. For example, measurement of light received by a user may be used as a metric to determine a current rhythm, and may be used, for example, in diagnosis of a condition, in identification of potential avenues for health and wellness optimization, in guiding a user to adjust rhythms (e.g., indoor/outdoor exposure patterns, device usage patterns, sleep patterns), other appropriate uses, or some combination thereof. Various embodiments may be implemented in the context of non-medical uses. Such implementations may include, for example, health and wellness, emotional wellness, other appropriate uses, or some combination thereof.

Exemplary Augmentation of Medical Devices and/or Pharmaceuticals

Various embodiments may, for example, be configured to augment and/or enhance existing medical devices and/or pharmacological therapies. For example, a medical device may be configured to be applied in a predetermined manner (e.g., location, duration, frequency, intensity). The medical device may, for example, require patient compliance to achieve a target therapeutical effect. In some embodiments, digital media delivery may be configured to augment the medical device. For example, in some embodiments a device that delivers compression therapy to limbs for wound care may require a relatively long period of time (e.g., 15 min., 30 min, 1 hour). A digital carrier may be configured to induce relaxation and/or entertainment during the therapy. Accordingly, the digital carrier may be configured, for example, to make the patient feel like the therapy time is shorter than it really is.

In some embodiments the digital carrier may be provided with one or more TDAs. The TDAs may be configured to be delivered such that the patient is guided through a therapy using the medical device being augmented. For example, a videogame may be paced such that the patient is induced to move at times corresponding to movement required by the therapy. In some embodiments the patient may be induced to perform a therapeutic mechanic required by the medical device (e.g., breathing, mental concentration, movement, exercise). In some embodiments the digital carrier may include guided media. In some embodiments the digital carrier may include passive media (e.g., including a set of instructions). In various embodiments the digital carrier (e.g., the TDAs) may be configured to generate a dopamine response or a matched serotonin, oxytocin, endorphins response. Accordingly, various embodiments may advantageously improve patient compliance. Some embodiments may advantageously augment the therapeutic mechanic(s) provided by the medical device therapy.

A pharmaceutical therapy may, for example, require conditions to be met before, during, and/or after a therapy event (e.g., taking a medication). The therapy may, for example, require physiological conditions (e.g., exercise level). The therapy may require predetermined mental and/or emotional conditions (e.g., calm). The therapy may, for example, require predetermined timing conditions (e.g., repeated on a schedule, timing after exercise). Various embodiments may provide a digital carrier(s) configured to augment a pharmacological therapy.

For example, in some embodiments a digital carrier (e.g., videogame, video, audio, digital book, app) may be configured to induce a patient to take a medication in a timely manner and/or in according to one or more predetermined conditions. A digital carrier may, for example, guide a patient in being calm and/or immobile for a predetermined period of time before, during, and/or after receiving the medication. A digital carrier may, for example, guide a patient in achieving a certain level of exercise before, during, and/or after taking the medication. The digital carrier may, for example, be configured with one or more TDAs configured to induce predetermined physiological response(s) before, during, and/or after a pharmacological therapy event such that the pharmacological therapy is augmented.

Some embodiments may, for example, be configured to provide stimuli during a pharmaceutical therapy event. For example, some embodiments may be configured to augment a neural treatment (e.g., psychedelic medications) by guiding a patient to a target therapeutic outcome. A digital carrier may, for example, be configured with TDAs configured to provide appropriate stimuli (e.g., suggestions) during treatment.

In some embodiments a digital carrier may, for example, be configured to augment a medical therapy by reducing a perceived time. For example, treatment events such as chemo, therapy and/or renal dialysis may be augmented by providing a digital carrier configured to generate a dopamine oxytocin, endorphins, and/or serotonin response such that patient compliance is increased. In some embodiments the digital carrier may be provided with TDAs configured to induce calming therapeutic modalities. In some embodiments a digital carrier may be provided with one or more TDAs configured to generate targeted visualization to augment a therapy. For example, chemotherapy treatment may be augmented by a digital carrier provided with TDAs to guide the user in targeted visualization of a desired result. The digital carrier may, for example, guide the user in visualizing the tumor and a corresponding reduction in size. The digital carrier may, for example, guide the user through gameplay (e.g., attacking cancer cells, rebuilding healthy tissue) configured to induce a desired physiological response (e.g., calmness, release of neurochemicals) and/or increase patient compliance.

Exemplary Electronic Embodiments

In various embodiments, some bypass circuits implementations may be controlled in response to signals from analog or digital components, which may be discrete, integrated, or a combination of each. Some embodiments may include programmed, programmable devices, or some combination thereof (e.g., PLAs, PLDs, ASICs, microcontroller, microprocessor), and may include one or more data stores (e.g., cell, register, block, page) that provide single or multi-level digital data storage capability, and which may be volatile, non-volatile, or some combination thereof. Some control functions may be implemented in hardware, software, firmware, or a combination of any of them.

Computer program products may contain a set of instructions that, when executed by a processor device, cause the processor to perform prescribed functions. These functions may be performed in conjunction with controlled devices in operable communication with the processor. Computer program products, which may include software, may be stored in a data store tangibly embedded on a storage medium, such as an electronic, magnetic, or rotating storage device, and may be fixed or removable (e.g., hard disk, floppy disk, thumb drive, CD, DVD).

Although an example of a system, which may be portable, has been described with reference to the above figures, other implementations may be deployed in other processing applications, such as desktop and networked environments.

Temporary auxiliary energy inputs may be received, for example, from chargeable or single use batteries, which may enable use in portable or remote applications. Some embodiments may operate with other DC voltage sources, such as a battery, for example. Alternating current (AC) inputs, which may be provided, for example from a 50/60 Hz power port, or from a portable electric generator, may be received via a rectifier and appropriate scaling. Provision for AC (e.g., sine wave, square wave, triangular wave) inputs may include a line frequency transformer to provide voltage step-up, voltage step-down, and/or isolation.

Although particular features of an architecture have been described, other features may be incorporated to improve performance. For example, caching (e.g., L1, L2, . . . ) techniques may be used. Random access memory may be included, for example, to provide scratch pad memory and or to load executable code or parameter information stored for use during runtime operations. Other hardware and software may be provided to perform operations, such as network or other communications using one or more protocols, wireless (e.g., infrared) communications, stored operational energy and power supplies (e.g., batteries), switching and/or linear power supply circuits, software maintenance (e.g., self-test, upgrades), and the like. One or more communication interfaces may be provided in support of data storage and related operations.

Some systems may be implemented as a computer system that can be used with various implementations. For example, various implementations may include digital circuitry, analog circuitry, computer hardware, firmware, software, or combinations thereof. Apparatus can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Various embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and CD-ROM and DVD-ROM disks. The processor and the memory can be supplemented by, or incorporated in, ASICs (application-specific integrated circuits).

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. Various embodiments may be implemented in a computer system that includes a graphical user interface and/or an Internet browser. To provide for interaction with a user, some implementations may be implemented on a computer having a display device, such as a CRT (cathode ray tube) or LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, the computers and networks forming the Internet, or some combination thereof. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, multiplexing techniques based on frequency, time, or code division, or some combination thereof. Some implementations may optionally incorporate features such as error checking and correction (ECC) for data integrity, or security measures, such as encryption (e.g., WEP) and password protection.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

Various examples of modules may be implemented using circuitry, including various electronic hardware. By way of example and not limitation, the hardware may include transistors, resistors, capacitors, switches, integrated circuits, other modules, or some combination thereof. In various examples, the modules may include analog logic, digital logic, discrete components, traces and/or memory circuits fabricated on a silicon substrate including various integrated circuits (e.g., FPGAs, ASICs), or some combination thereof. In some embodiments, the module(s) may involve execution of preprogrammed instructions, software executed by a processor, or some combination thereof. For example, various modules may involve both hardware and software.

In an exemplary aspect, a computer-implemented method may be performed by at least one processor to cause quality management operations to be performed to manage therapeutic digital assets in a non-medical environment. The operations may include receive multiple non-medical digital assets (NMDAs). The operations may include receive, for at least one of the NMDAs. The first signal may correspond to a therapeutic modality. The at least one of the NMDAs may include a therapeutic digital asset (TDA). The operations may include generate, in response to the first signal, a first metadata structure (MDS) associating the therapeutic modality with the TDA. The operations may include store the first MDS in a first data store. The operations may include receive a second signal corresponding to a risk mitigation. The risk mitigation may correspond to the therapeutic modality. The operations may include generate, in response to the second signal, a second MDS associating the risk mitigation with the TDA. The operations may include store the second MDS in a second data store. The operations may include receive a third signal corresponding to a test profile. The test profile may be based on the risk mitigation, the TDA, and the therapeutic modality. The test profile may include a test input, a test operation to be applied to the TDA based on the test input, and an approved test result corresponding to the test operation. The operations may include generate, in response to the third signal, a third MDS associating the test profile with the TDA and the risk mitigation. The operations may include store the third MDS in a third data store. The operations may include receive a fourth signal corresponding to an acceptable test result generated in response to application of the test operation to the TDA. The operations may include generate, in response to the fourth signal, a fourth MDS associating the acceptable test result with the TDA. The operations may include generate and transmit, in response to the fourth signal, a fifth signal configured to induce incorporation of the TDA, together with the first MDS, with the NMDAs.

Generate the second MDS may include generating an updated first MDS. Generate the third MDS may include generating at least one of: an updated second MDS and an updated first MDS. Generate the fourth MDS may include generating at least one of: an updated first MDS, an updated second MDS, and an updated third MDS.

The operations may further include generate the first signal corresponding to the therapeutic modality. Generate the first signal may include a set of operations including apply a machine learning model to the NMDAs to generate, based on multiple predetermined therapeutic modalities and a set of predetermined associations between the predetermined therapeutic modalities and corresponding digital assets, at least one suggested association between at least one of the NMDAs and at least one of the predetermined therapeutic modalities.

The operations may further include generate the second signal corresponding to the risk mitigation. Generate the second signal may include a set of operations including apply a machine learning model to the TDA and the therapeutic modality to determine, based on (a) a set of predetermined TDAs corresponding to the therapeutic modality and (b) a corresponding set of risk mitigations, at least one suggested risk mitigation corresponding to the TDA.

The operations may further include generate the third signal corresponding to the test profile. Generate the third signal may include a set of operations including apply a machine learning model to the TDA and the corresponding risk mitigation to generate, based on (a) multiple predetermined TDAs and corresponding risk mitigations and (b) a set of corresponding test profiles, at least one suggested test profile corresponding to the TDA and the risk mitigation.

The operations may further include generate, in response to a request for a suggested TDA corresponding to the therapeutic modality, at least one signal corresponding to a suggestion of the TDA. The request for a suggested TDA may include at least one attribute of a corresponding digital content delivery environment (DCDE). The operations may further include determine, based on the test profile and the at least one attribute of the corresponding DCDE, whether the TDA is suitable for delivery via the DCDE. The operations may further include, in response to determining that the TDA is suitable, then generate the at least one signal corresponding to the suggestion of the TDA.

The TDA may be configured to induce dopamine generation. The TDA may be configured to induce serotonin generation. The TDA may be configured to induce a state of perceptual learning.

The TDA may include a videogame component. The TDA may include a digital text component. The TDA may include a movie. The TDA may include music. The TDA may include software code. The TDA may include digital media.

At least one of the NMDAs may be pre-existing. At least one of the NMDAs may be submitted to be considered as a medical digital asset.

In an exemplary aspect, a computer-implemented method may be performed by at least one processor to cause quality management operations to be performed to manage therapeutic digital assets in a non-medical environment. The operations may include receive a first signal corresponding to a change in a non-medical digital content delivery environment (DCDE) comprising a therapeutic digital asset (TDA). The operations may include retrieve, from a first data store and in response to the first signal, a first metadata structure corresponding to the TDA and comprising an association between the TDA and a test profile. The test profile may include a test input, a test operation to be applied to the TDA based on the test input, and an approved test result corresponding to the test operation. The operations may include apply the test profile to the TDA based on the change in the non-medical DCDE to generate a test result corresponding to an outcome of application of the test operation to the TDA after the change. The operations may include generate, in response to determining that the generated test result does not correspond to the approved test result, a third signal configured to induce deactivation of the TDA in the non-medical DCDE.

The operations may further include generate, in response to determining that the generated test result does not correspond to the approved test result, a display. The display may include an indication of the TDA. The display may include an indication of the change in the non-medical DCDE. The display may include an indication of the approved test result. The display may include an indication of the generated test result. The display may be configured to prompt a user for input corresponding to an approval state of the TDA with respect to the change. The operations may further include, in response to determining that the input from the user corresponds to approval of the TDA with respect to the change, then generate a fourth signal configured to induce activation of the TDA in the non-medical DCDE.

The operations may further include retrieve a second metadata structure associating the TDA with at least one risk mitigation. The operations may further include generate, based on the at least one risk mitigation and the change in the non-medical DCDE, an updated TDA. The operations may further include generate a third metadata structure associating the TDA with updated risk mitigation information.

The operations may further include generate the first signal in response to detecting the change in the non-medical (DCDE). The first signal may be generated in response to receiving, from the non-medical DCDE, a status metadata structure including at least one attribute corresponding to the DCDE and associated with a therapeutic modality of the TDA.

The operations may further include apply a machine learning model the TDA, the test profile, and the generated test result, to generate an updated TDA configured to satisfy the test profile in the DCDE corresponding to the change. The machine learning model may be configured to generate the TDA based at least on historical changes to DCDEs and corresponding updates applied to corresponding TDAs. Generate the updated TDA may be performed by a set of operations including apply the machine learning model to generate a first set of suggested updates to the TDA and corresponding confidence intervals; determine a second set of suggested updates to the TDA, selected from the first set of suggested updates based on a predetermined range of confidence intervals; and, generate a display including the second set of suggested updates to the TDA, indication of corresponding confidence intervals, and the change to the non-medical DCDE. The display may be configured to prompt a user to input a selection of one of the second set of suggested updates.

The TDA may be configured to induce dopamine generation. The TDA may be configured to induce serotonin generation. The TDA may be configured to induce a state of perceptual learning.

The non-medical DCDE may include a videogame. The non-medical DCDE may include digital text delivery. The non-medical DCDE may include a movie. The non-medical DCDE may include music.

The TDA may include software code. The TDA may include digital media.

In an exemplary aspect, a computer-implemented method may be performed by at least one processor to cause content delivery operations to be performed to deliver therapeutic digital assets upon demand. The operations may include receive a signal from a user corresponding to a request for application of a therapeutic modality. The user may have been previously introduced to the therapeutic modality in a non-medical digital content delivery environment (DCDE). The operations may include retrieve, in response to the signal and from a first data store, a first metadata structure (MDS) corresponding to the therapeutic modality and the non-medical DCDE. The first MDS may associate the therapeutic modality and the non-medical DCDE with at least one therapeutic digital asset (TDA). The operations may include generate, based on the first MDS, a dynamic interface including the at least one TDA such that, when the user interacts with the dynamic interface, the user is prompted to perform at least one therapeutic physiological response associated with the therapeutic modality and previously learned by the user through the non-medical DCDE.

The at least one TDA may be configured to induce dopamine generation. The at least one TDA may be configured to induce serotonin generation.

The therapeutic modality may include a breathing mechanic. The therapeutic modality may include a mental concentration mechanic. The therapeutic modality may include a calming mechanic.

The non-medical DCDE may include a videogame. The non-medical DCDE may include digital text delivery. The non-medical DCDE may include a movie. The non-medical DCDE may include music.

The at least one TDA may include software code. The at least one TDA may include digital media. The at least one TDA may include at least one image. The at least one TDA may include music. The at least one TDA may include a sequence of images and audio.

Generate the dynamic interface may performed by a set of operations including apply a machine learning model to the TDA and the signal to generate the dynamic interface based on a set of predetermined TDAs, a set of corresponding predetermined requests, and a set of interface components corresponding to the set of predetermined TDAs and the set of corresponding predetermined requests. The set of predetermined requests and the set of interface components may include historical requests and corresponding interface components of the user.

The dynamic interface may include digital media. The dynamic interface may include at least one image. The dynamic interface may include music. The dynamic interface may include a sequence of images and audio. The dynamic interface may include text.

The dynamic interface may be configured to be delivered to the user by a portable computing device. The dynamic interface may be configured to prompt the user for input. The dynamic interface may be generated at least partially in response to feedback from the user. The feedback may include at least one physiological metric.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:

1. An immersive medicine generation system comprising:
 a communication module;
 a deployment layer operably coupled to an uncontrolled digital asset deployment environment (DADE) operably coupled to at least one user device through the communication module, the deployment layer comprising a plurality of therapeutic digital assets (TDAs);
 a data store operably coupled to the communication module, comprising a program of instructions and a therapeutic modality comprising at least one therapeutic induction mechanism;
 a therapeutic digital asset management engine (TDAME) configured to cause quality management operations to be performed; and,
 a processor operably coupled to the data store and the TDAME such that, when the processor executes the program of instructions, the processor causes operations to be performed to cause the quality management operations to be performed while generating immersive medicine using a non-medical digital asset (NMDA) comprising a videogame, the operations comprising:
  receive the NMDA at the communication module, wherein the NMDA is submitted from a game developer using the at least one user device to be considered as a medical digital asset;
  generate a first metadata structure (MDS) based on an evaluation between the NMDA and the therapeutic modality;
  generate a TDA based on the first MDS, wherein the first MDS comprising an association between the TDA and the therapeutic modality;
  receive a risk analysis signal corresponding to the therapeutic modality;
  generate, in response to the risk analysis signal, a second MDS comprising a risk mitigation associated with the TDA;
  generate, based on the second MDS, a third MDS, wherein the third MDS comprises a test profile comprising a test input, a test operation to be applied to the TDA based on the test input and an approved test result corresponding to the test operation;
  upon receiving a result signal corresponding to an acceptable test result generated in response to application of the test operation to the TDA, generate, in response to the result signal, a fourth MDS associating the acceptable test result with the TDA;
  generate, based on the fourth MDS, an incorporation signal to induce incorporation of the TDA with the first MDS to the deployment layer, such that the plurality of TDAs generated from NMDAs and incorporated in the deployment layer are verified based on the test profile;
  transmit an activation signal such that the plurality of TDAs are operated into an accessible state in the uncontrolled DADE such that at least one implementation device communicably coupled to the uncontrolled DADE is provided access to the plurality of TDAs;
  upon receiving a first signal corresponding to a change in a non-medical digital content of the TDA;
  retrieve, from a first data store and in response to the first signal, the third MDS corresponding to the TDA;
  apply the test profile to the TDA based on the change in the non-medical digital content to generate a test result corresponding to an outcome of application of the test operation to the TDA after the change; and,
  automatically generate, in response to determining that the generated test result does not correspond to the approved test result, a second signal configured to automatically induce deactivation of the TDA in the deployment layer such that the TDA is suspended from the accessible state in the uncontrolled DADE.

2. The immersive medicine generation system of claim 1, wherein the change in a non-medical digital content of the TDA comprises an update of an operating system running the NMDA.

3. The immersive medicine generation system of claim 1, wherein the change in a non-medical digital content of the TDA comprises an update in an opening logo of the NMDA.

4. The immersive medicine generation system of claim 1, wherein the deployment layer is operably coupled to the processor and is configured to control an activation state of the plurality of TDAs.

5. The immersive medicine generation system of claim 1, further comprising a risk assessment engine comprising a machine learning model, wherein the operations further comprise:
generate the risk mitigation in a set of operations comprising:
apply a machine learning model to the TDA and the therapeutic modality to determine, based on (a) a set of predetermined TDAs corresponding to the therapeutic modality and (b) a corresponding set of risk mitigations, at least one suggested risk mitigation corresponding to the TDA.

6. The immersive medicine generation system of claim 1, wherein the TDA is configured to induce a state of perceptual learning.

7. The immersive medicine generation system of claim 1, wherein the TDA comprises a digital text component.

8. The immersive medicine generation system of claim 1, wherein the data store further comprises an asset integration profile (AIP) associated with the therapeutic modality, wherein the AIP comprises parameters, criteria and instructions for delivering the therapeutic modality via an interactive digital carrier (IDC), wherein the IDC comprises a TDA incorporated in the deployment layer, such that, in response of user's engagement of the therapeutic modality, the IDC is configured to alter the TDA in runtime based on the AIP.

9. Immersive medicine generation system of claim 1, wherein the at least one user device is independent from the at least one implementation device.

10. An immersive medicine generation system comprising:
a communication module;
a deployment layer operably coupled to an uncontrolled digital asset deployment environment (DADE) operably coupled to at least one user device through the communication module, the deployment layer comprises a plurality of therapeutic digital assets (TDAs);
a data store operably coupled to the communication module, comprising a program of instructions and a therapeutic modality comprising at least one therapeutic induction mechanism; and,
a processor operably coupled to the data store such that, when the processor executes the program of instructions, the processor causes quality management operations to be performed while generating immersive medicine using a non-medical digital asset (NMDA), the operations comprising:
receive a NMDA at the communication module;
generate a first metadata structure (MDS) based on an evaluation between the NMDA and the therapeutic modality;
generate a TDA based on the first MDS, wherein the first MDS comprising an association between the TDA and the therapeutic modality;
receive a risk analysis signal corresponding to the therapeutic modality;
generate, in response to the risk analysis signal, a second MDS comprising a risk mitigation associated with the TDA;
generate, based on the second MDS, a third MDS, wherein the third MDS comprises a test profile comprising a test input, a test operation to be applied to the TDA based on the test input and an approved test result corresponding to the test operation;
upon receiving a result signal corresponding to an acceptable test result generated in response to application of the test operation to the TDA, generate, in response to the result signal, a fourth MDS associating the acceptable test result with the TDA; and,
generate and transmit, based on the fourth MDS, an incorporation signal to induce incorporation of the TDA with the first MDS to the deployment layer, such that the plurality of TDAs generated from NMDAs and incorporated in the deployment layer are verified based on the test profile and are operated from an inaccessible state into an accessible state in the uncontrolled DADE such that at least one implementation device communicably coupled to the uncontrolled DADE is provided access to the plurality of TDAs.

11. The immersive medicine generation system of claim 10, further comprising a therapeutic digital asset management engine (TDAME) operably coupled to the processor, wherein the TDAME is configured to perform operations to interrupt delivery of immersive medicine, the operations comprising:
receive a first signal corresponding to a change in a non-medical digital content of a TDA incorporated in the deployment layer;
retrieve, from a first data store and in response to the first signal, a third MDS corresponding to the TDA and comprising an association between the TDA and a test profile corresponding to the TDA;
apply the test profile to the TDA based on the change in the non-medical digital content to generate a test result corresponding to an outcome of application of the test operation to the TDA after the change; and,
automatically generate, in response to determining that the generated test result does not correspond to the approved test result, a third signal configured to automatically induce deactivation of the TDA in the deployment layer such that the TDA is suspended to be accessible from the uncontrolled DADE.

12. The immersive medicine generation system of claim 11, wherein the change in the non-medical digital content of the TDA comprises an update of an operating system running the NMDA.

13. The immersive medicine generation system of claim 11, wherein the change in the non-medical digital content of the TDA comprises an update in an opening logo of the NMDA.

14. The immersive medicine generation system of claim 10, wherein the deployment layer is operably coupled to the processor and is configured to control an activation state of the plurality of TDAs.

15. The immersive medicine generation system of claim 10, further comprising a risk assessment engine comprising a machine learning model, wherein the operations further comprise:
generate the risk mitigation in a set of operations comprising:
apply a machine learning model to the TDA and the therapeutic modality to determine, based on (a) a set of predetermined TDAs corresponding to the therapeutic modality and (b) a corresponding set of risk mitigations, at least one suggested risk mitigation corresponding to the TDA.

16. The immersive medicine generation system of claim 10, wherein the TDA is configured to induce a state of perceptual learning.

17. The immersive medicine generation system of claim 10, wherein the TDA comprises a videogame component.

18. The immersive medicine generation system of claim 10, wherein the TDA comprises a digital text component.

19. The immersive medicine generation system of claim 10, wherein the TDA comprises music.

20. The immersive medicine generation system of claim 10, wherein the NMDA is received as a submission to be considered as a medical digital asset.

21. The immersive medicine generation system of claim 10, wherein the data store further comprises an asset integration profile (AIP) associated with the therapeutic modality, wherein the AIP comprises parameters, criteria and instructions for delivering the therapeutic modality via an interactive digital carrier (IDC), wherein the IDC comprises a TDA incorporated in the deployment layer, such that, in response of user's engagement of the therapeutic modality in the TDA, the IDC is configured to alter the TDA in runtime based on the AIP.

22. Immersive medicine generation system of claim 10, wherein the at least one user device is independent from the at least one implementation device.

* * * * *